US011484576B2

(12) United States Patent
Sanes et al.

(10) Patent No.: US 11,484,576 B2
(45) Date of Patent: Nov. 1, 2022

(54) METHODS OF PROMOTING CORTICOSPINAL NEURONAL OUTGROWTH IN NEURONAL LESIONS USING A PRO-REGENERATIVE HUMAN OSTEOPONTIN FRAGMENT

(71) Applicants: THE CHILDREN'S MEDICAL CENTER CORPORATION, Boston, MA (US); PRESIDENT AND FELLOWS OF HARVARD COLLEGE, Cambridge, MA (US)

(72) Inventors: Joshua R. Sanes, Cambridge, MA (US); Xin Duan, Somerville, MA (US); Mu Qiao, Cambridge, MA (US); Zhigang He, Wellesley, MA (US); Fengfeng Bei, Chestnut Hill, MA (US); Yuanyuan Liu, Boston, MA (US)

(73) Assignees: THE CHILDREN'S MEDICAL CENTER CORPORATION, Boston, MA (US); PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

(21) Appl. No.: 16/639,232

(22) PCT Filed: Aug. 13, 2018

(86) PCT No.: PCT/US2018/046436
§ 371 (c)(1),
(2) Date: Feb. 14, 2020

(87) PCT Pub. No.: WO2019/036331
PCT Pub. Date: Feb. 21, 2019

(65) Prior Publication Data
US 2020/0237868 A1  Jul. 30, 2020

Related U.S. Application Data

(60) Provisional application No. 62/545,772, filed on Aug. 15, 2017.

(51) Int. Cl.
| *A61K 38/18* | (2006.01) |
| *A61K 38/00* | (2006.01) |
| *C07K 14/475* | (2006.01) |
| *C07K 14/48* | (2006.01) |
| *A61K 38/17* | (2006.01) |
| *C07K 14/47* | (2006.01) |
| *C07K 14/00* | (2006.01) |
| *A61K 38/19* | (2006.01) |
| *A61P 25/28* | (2006.01) |
| *A61K 31/4409* | (2006.01) |
| *A61K 38/30* | (2006.01) |

(52) U.S. Cl.
CPC .......... *A61K 38/19* (2013.01); *A61K 31/4409* (2013.01); *A61K 38/185* (2013.01); *A61K 38/30* (2013.01); *A61P 25/28* (2018.01)

(58) Field of Classification Search
CPC ...... A61K 28/00; A61K 38/16; A61K 38/185; A61K 38/30; A61K 38/18; A61P 25/28; A61P 25/00
See application file for complete search history.

(56) References Cited

U.S. PATENT DOCUMENTS

| 7,197,099 | B2* | 3/2007 | Dosaka | H03L 7/0812 |
| | | | | 327/158 |
| 7,217,587 | B2* | 5/2007 | Fu | G02B 26/0841 |
| | | | | 257/E25.03 |
| 7,217,687 | B2* | 5/2007 | Boschert | A61P 19/10 |
| | | | | 514/17.7 |
| 7,297,099 | B2* | 11/2007 | Boschert | A61P 9/10 |
| | | | | 424/85.4 |
| 8,367,352 | B2* | 2/2013 | He | A61P 27/02 |
| | | | | 435/7.21 |
| 8,728,756 | B2* | 5/2014 | He | A61P 43/00 |
| | | | | 435/29 |
| 9,511,036 | B2* | 12/2016 | He | A61P 25/00 |
| 10,117,866 | B2* | 11/2018 | He | A61P 25/00 |
| 10,195,247 | B2* | 2/2019 | He | A61K 31/444 |
| 10,918,697 | B2* | 2/2021 | He | A61K 45/06 |
| 2004/0235720 | A1 | 11/2004 | Boschert et al. | |
| 2014/0179741 | A1 | 6/2014 | Benowitz et al. | |
| 2014/0256795 | A1* | 9/2014 | He | A61K 31/555 |
| | | | | 514/44 A |

(Continued)

FOREIGN PATENT DOCUMENTS

| WO | WO2008/086449 | * | 7/2008 |
| WO | WO2017/077539 | * | 5/2017 |

OTHER PUBLICATIONS

The factsheet of Osteopontin from MeSH at NCBI website: www.ncbi.nlm.nih.gov/mesh/68053495 retrieved on Feb. 8, 2021.*

(Continued)

*Primary Examiner* — Chang-Yu Wang
(74) *Attorney, Agent, or Firm* — Nixon Peabody LLP; David S. Resnick; Shayne Y. Huff

(57) ABSTRACT

Disclosed herein are methods for promoting neuronal outgrowth in a subject with a neuronal lesion in their CNS by administering effective amounts of a pro-regenerative OPN fragment, optionally with IGF1 and/or BDNF. A voltage gated potassium channel blocker can also be administered. Pharmaceutical compositions, devices for administration, and kits are also disclosed.

11 Claims, 41 Drawing Sheets

Specification includes a Sequence Listing.

(56) References Cited

U.S. PATENT DOCUMENTS

2018/0303974 A1* 10/2018 Baranes .............. A61L 27/3616

OTHER PUBLICATIONS

The factsheet of SSP1/Osteopontin from MeSH at NCBI website: www.ncbi.nlm.nih.gov/mesh/67506895 retrieved on Feb. 8, 2021.*
https://pubchem.ncbi.nlm.nih.gov/compound/4-aminopyridine.*
Duan et al., Neuron, Mar. 8, 2015; 85:1244-1256.*
Purves D, Augustine GJ, Fitzpatrick D, et al., editors. Neuroscience. 2nd edition. Sunderland (MA): Sinauer Associates; 2001. The Retina. Available from: https://www.ncbi.nlm.nih.gov/books/NBK10885/.*
Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Falkenburger et al., J. Neural. Transm, 2006; 70:261-268.*
Tayebati, Mech. Ageing Dev. 2006. 127: 100-8.*
Sarter, Neurosci. and Biobehav. Rev. 2004. 28: 645-650.*
Henstridge et al. Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Broom et al. Exp. Neurol. 2015; 263:1-7.*
Gao et al. Macromol. Biosci. 2015; 15:1070-1080.*
Bei et al., "Restoration of visual function by enhancing conduction in regenerated axons." Cell 164(1-2):219-232 (2016).
Watson et al. "Induction of reproducible brain infarction by photochemically initiated thrombosis." Annals of Neurology: Official Journal of the American Neurological Association and the Child Neurology Society 17(5): 497-504 (1985).
Weidner et al. "Spontaneous corticospinal axonal plasticity and functional recovery after adult central nervous system injury." Proceedings of the National Academy of Sciences 98(6): 3513-3518 (2001).
Zukor et al. "Short hairpin RNA against PTEN enhances regenerative growth of corticospinal tract, axons after spinal cord injury." Journal of Neuroscience 33(39): 15350-15361 (2013).
Alilain et al. "Functional regeneration of respiratory pathways after spinal cord injury." Nature 475(7355): 196-200 (2011).
Ballermann et al. "Spontaneous locomotor recovery in spinal cord injured rats is accompanied by anatomical plasticity of reticulospinal fibers." European Journal of Neuroscience 23(8): 1988-1996 (2006).
Bareyre et al. "The injured spinal cord spontaneously forms a new intraspinal circuit in adult rats." Nature Neuroscience 7(3): 269-277 (2004).
Bareyre et al. "Transgenic labeling of the corticospinal tract for monitoring axonal responses to spinal cord injury." Nature Medicine 11(12): 1355-1360 (2005).
Blackmore et al. "Krüppel-like Factor 7 engineered for transcriptional activation promotes axon regeneration in the adult corticospinal tract." Proceedings of the National Academy of Sciences 109(19): 7517-7522 (2012).
Blight et al. "The effects of 4-aminopyridine on neurological deficits in chronic cases of traumatic spinal cord injury in dogs: a phase I clinical trial." Journal of Neurotrauma 8(2): 103-119 (1991).
Bostock et al. "The effects of 4-aminopyridine and tetraethylammonium ions on normal and demyelinated mammalian nerve fibres." The Journal of Physiology 313(1): 301-315 (1981).
Carmel et al. "Chronic electrical stimulation of the intact corticospinal system after unilateral injury restores skilled locomotor control and promotes spinal axon outgrowth." Journal of Neuroscience 30(32): 10918-10926 (2010).
Carmel et al. "Electrical stimulation of motor cortex in the uninjured hemisphere after chronic unilateral injury promotes recovery of skilled locomotion through ipsilateral control." Journal of Neuroscience 34(2): 462-466 (2014).
Courtine et al. "Recovery of supraspinal control of stepping via indirect propriospinal relay connections after spinal cord injury." Nature Medicine 14(1): 69-74 (2008).
Courtine et al. "Transformation of nonfunctional spinal circuits into functional states after the loss of brain input." Nature Neuroscience 12(10): 1333-1342 (2009).
Danilov et al. "Conditional genetic deletion of PTEN after a spinal cord injury enhances regenerative growth of CST axons and motor function recovery in mice." Experimental Neurology 266: 147-160 (2015).
Donovan et al. "Intravenous infusion of 4-AP in chronic spinal cord injured subjects." Spinal Cord 38(1): 7-15 (2000).
Drew. "Motor cortical activity during voluntary gait modifications in the cat. I. Cells related to the forelimbs." Journal of Neurophysiology 70(1): 179-199 (1993).
Du et al. "Pten deletion promotes regrowth of corticospinal tract axons 1 year after spinal cord injury." Journal of Neuroscience 35(26): 9754-9763 (2015).
Fong et al. "Spinal cord-transected mice learn to step in response to quipazine treatment and robotic training." Journal of Neuroscience 25(50): 11738-11747 (2005).
Fouad et al. "Cervical sprouting of corticospinal fibers after thoracic spinal cord injury accompanies shifts in evoked motor responses." Current Biology 11(22): 1766-1770 (2001).
Garcia-Alias et al. "Plasticity of subcortical pathways promote recovery of skilled hand function in rats after corticospinal and rubrospinal tract injuries." Experimental Neurology 266: 112-119 (2015).
Geoffroy et al. "Effects of PTEN and Nogo codeletion on corticospinal axon sprouting and regeneration in mice." Journal of Neuroscience 35(16): 6413-6428 (2015).
Georgopoulos et al. "Visuomotor coordination in reaching and locomotion." Science 245(4923): 1209-1210 (1989).
Giehl et al. "BDNF and NT-3, but not NGF, prevent axotomy-induced death of rat corticospinal neurons in vivo." European Journal of Neuroscience 8(6): 1167-1175 (1996).
Hernandez-Sanchez et al. "The role of the tyrosine kinase domain of the insulin-like growth factor-I receptor in intracellular signaling, cellular proliferation, and tumorigenesis." Journal of Biological Chemistry 270(49): 29176-29181 (1995).
Jin et al. "Restoration of skilled locomotion by sprouting corticospinal axons induced by co-deletion of PTEN and SOCS3." Nature Communications 6(1): 8074 pp. 1-12 (2015).
Kahles et al. "Osteopontin: A novel regulator at the cross roads of inflammation, obesity and diabetes." Molecular Metabolism 3(4): 384-393 (2014).
Kazanecki et al. "Control of osteopontin signaling and function by post-translational phosphorylation and protein folding." Journal of Cellular Biochemistry 102(4): 912-924 (2007).
Lang et al. "STAT3 promotes corticospinal remodelling and functional recovery after spinal cord injury." EMBO Reports 14(10): 931-937 (2013).
Lewandowski et al. "AAVshRNA-mediated suppression of PTEN in adult rats in combination with salmon fibrin administration enables regenerative growth of corticospinal axons and enhances recovery of voluntary motor function after cervical spinal cord injury." Journal of Neuroscience 34(30): 9951-9962 (2014).
Li et al. "An age-related sprouting transcriptome provides molecular control of axonal sprouting after stroke." Nature Neuroscience 13(12): 1496-1504 (2010).
Li et al. "GDF10 is a signal for axonal sprouting and functional recovery after stroke." Nature Neuroscience 18(12): 1737-1745 (2015).
Liddell et al. "Pyramidal section in the cat." Brain 67(1): 1-9 (1944).
Liu et al. "PTEN deletion enhances the regenerative ability of adult corticospinal neurons." Nature Neuroscience 13(9): 1075-1081 (2010).
Lu et al. "Neurotrophism without neurotropism: BDNF promotes survival but not growth of lesioned corticospinal neurons." Journal of Comparative Neurology 436(4): 456-470 (2001).
Maier et al., "Constraint-induced movement therapy in the adult rat after unilateral corticospinal tract injury." Journal of Neuroscience 28(38): 9386-9403 (2008).

(56) References Cited

OTHER PUBLICATIONS

Murray et al. "Recovery of motoneuron and locomotor function after spinal cord injury depends on constitutive activity in 5-HT 2C receptors." Nature Medicine 16(6): 694-700 (2010).

Musienko et al. "Controlling specific locomotor behaviors through multidimensional monoaminergic modulation of spinal circuitries," Journal of Neuroscience 31(25): 9264-9278 (2011).

O'Leary. "Development of connectional diversity and specificity in the mammalian brain by the pruning of collateral projections." Current Opinion in Neurobiology 2(1): 70-77 (1992).

O'Leary et al. "Development of projection neuron types, axon pathways, and patterned connections of the mammalian cortex." Neuron 10(6): 991-1006 (1993).

Özdinler et al. "IGF-I specifically enhances axon outgrowth of corticospinal motor neurons." Nature Neuroscience 9(11): 1371-1381 (2006).

Pollak. "Insulin and insulin-like growth factor signalling in neoplasia." Nature Reviews Cancer 8(12): 915-928 (2008).

Raineteau et al. "Plasticity of motor systems after incomplete spinal cord injury." Nature Reviews Neuroscience 2(4): 263-273 (2001).

Ruschel et al. "Systemic administration of epothilone B promotes axon regeneration after spinal cord injury." Science 348(6232): 347-352 (2015).

Siddle. "Molecular basis of signaling specificity of insulin and IGF receptors: neglected corners and recent advances." Frontiers in Endocrinology 3: 34 pp. 1-24 (2012).

Sun et al. "Novel potassium channel blocker, 4-AP-3-MeOH, inhibits fast potassium channels and restores axonal conduction in injured guinea pig spinal cord white matter." Journal of Neurophysiology 103: 469-478 (2010).

Takeoka et al. "Muscle spindle feedback directs locomotor recovery and circuit reorganization after spinal cord injury." Cell 159(7): 1626-1639 (2014).

Tetzlaff et al. "Response of rubrospinal and corticospinal neurons to injury and neurotrophins." Progress in Brain Research 103: 271-286 (1994).

Thoenen et al. "Neurotrophins: from enthusiastic expectations through sobering experiences to rational therapeutic approaches." Nature Neuroscience 5(11): 1046-1050 (2002).

Van Den Brand et al. "Restoring voluntary control of locomotion after paralyzing spinal cord injury." Science 336(6085): 1182-1185 (2012).

Wahl et al. "Asynchronous therapy restores motor control by rewiring of the rat corticospinal tract after stroke." Science 344(6189): 1250-1255 (2014).

Wang et al. "Osteopontin: role in immune regulation and stress responses." Cytokine & Growth Factor Reviews 19(5-6): 333-345 (2008).

Wang et al. "Overexpression of Sox11 promotes corticospinal tract regeneration after spinal injury while interfering with functional recovery." Journal of Neuroscience 35(7): 3139-3145 (2015).

\* cited by examiner

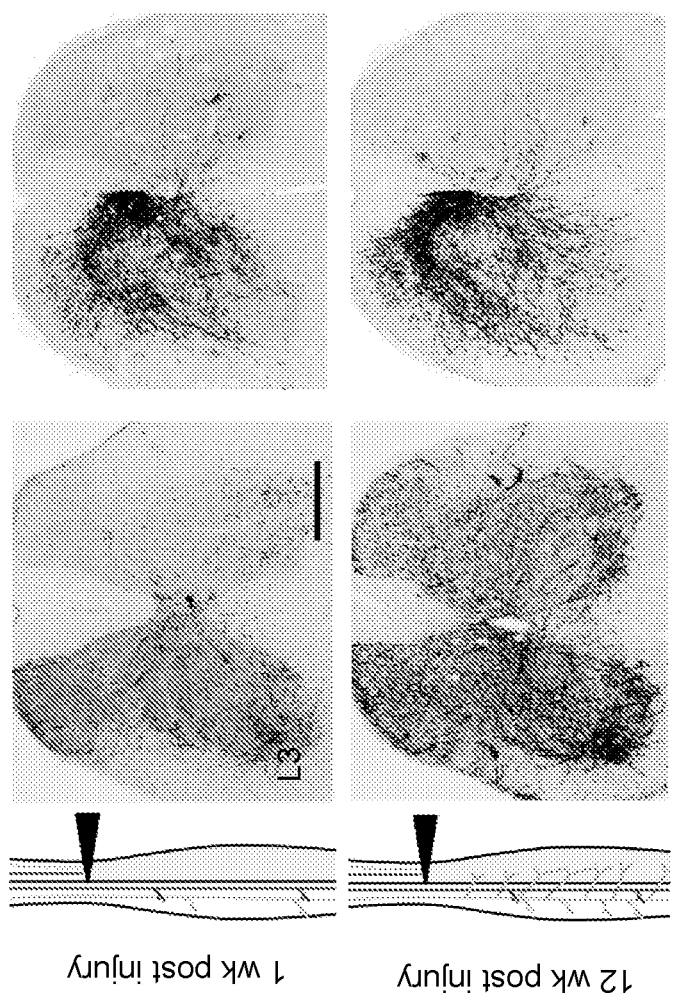
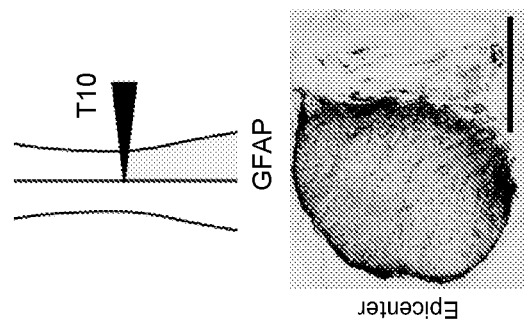
FIG 1A
FIG 1B

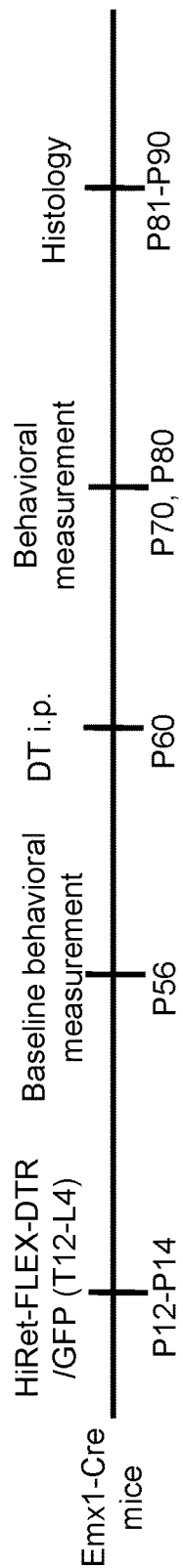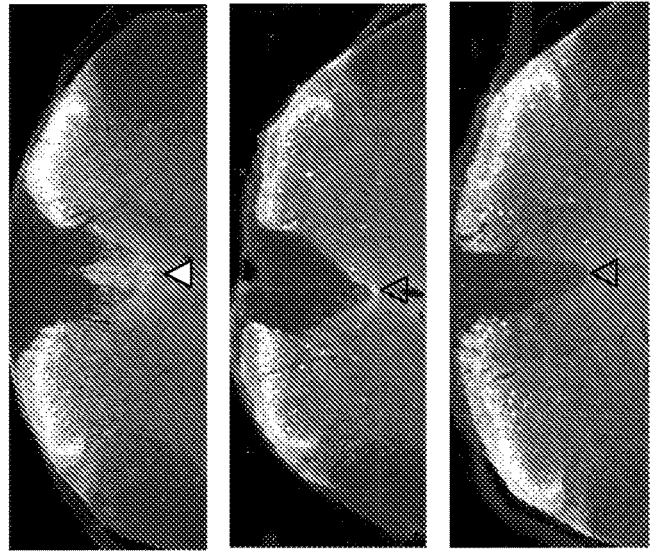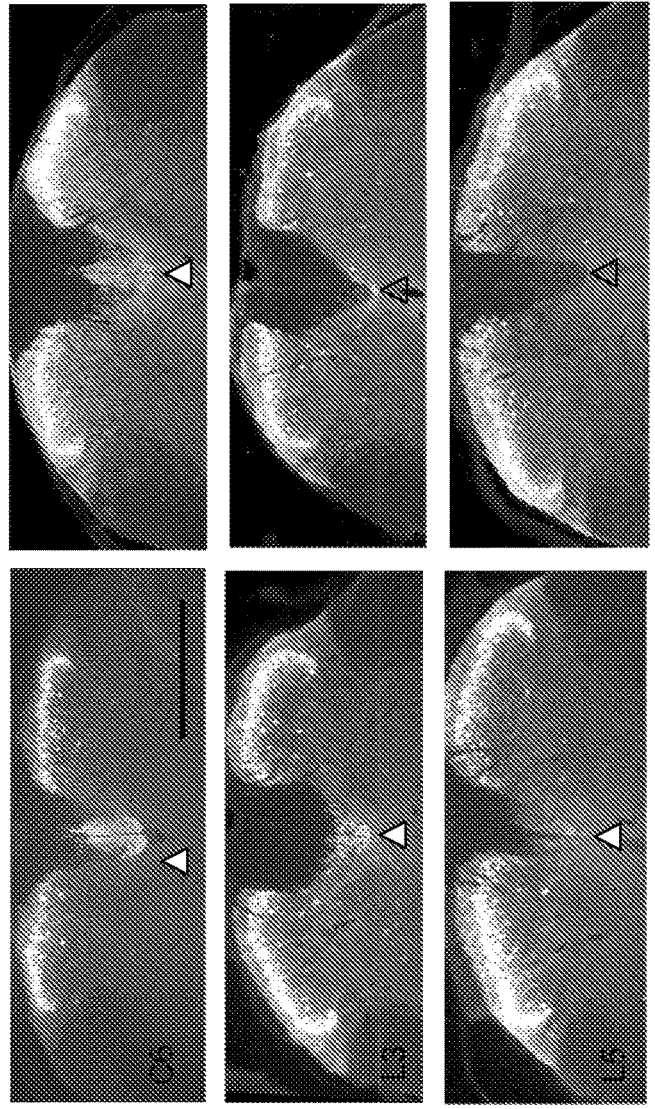
*FIG 1F*
*FIG 1G*

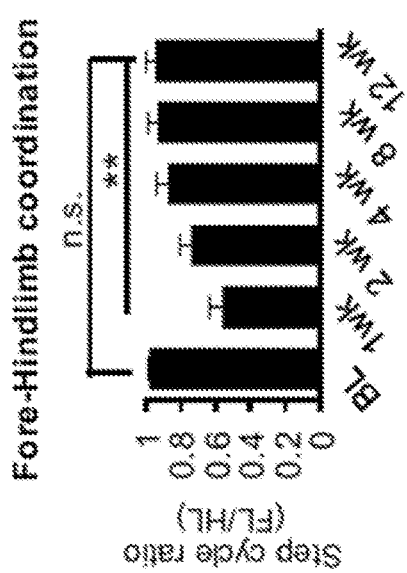
FIG 2G
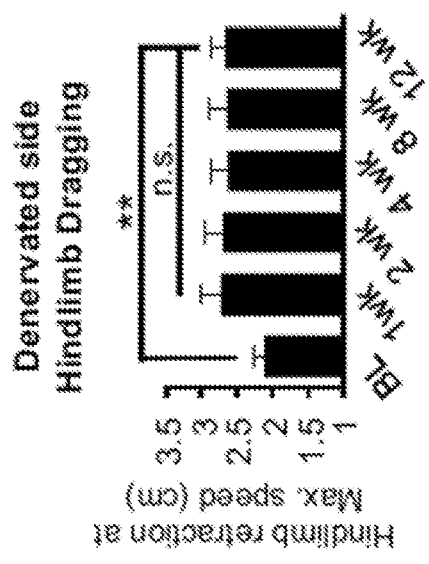
FIG 2J
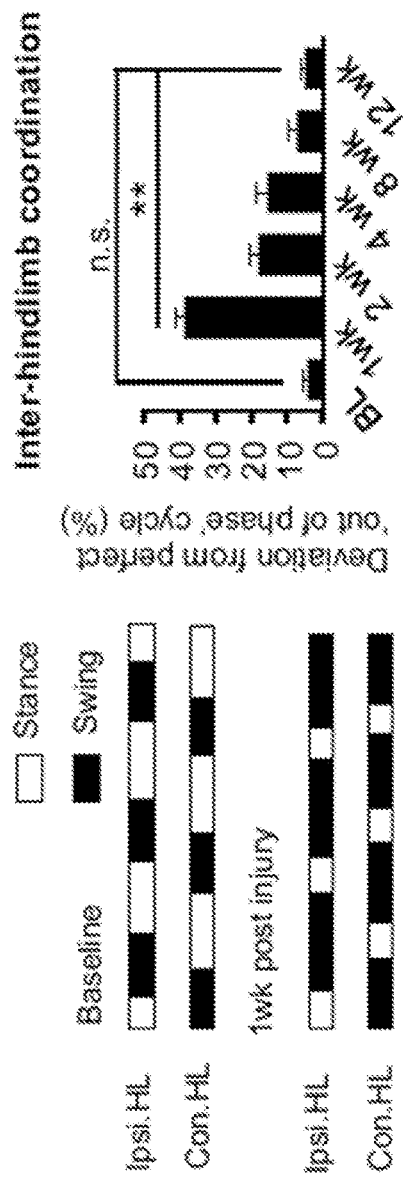
FIG 2F
FIG 2E
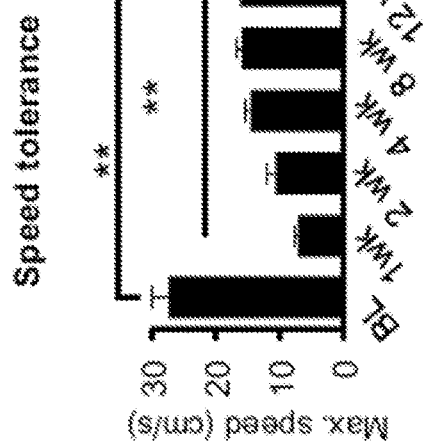
FIG 2I
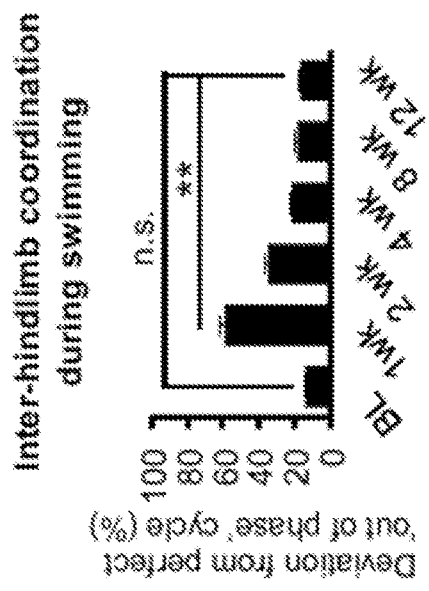
FIG 2H

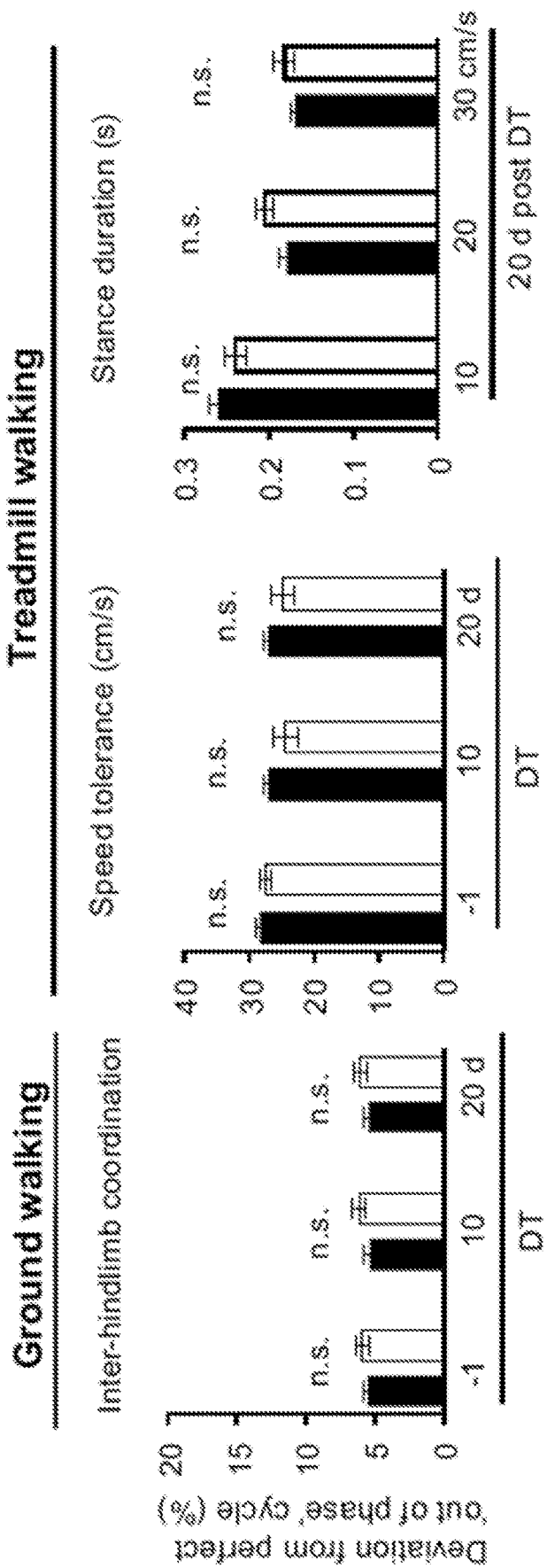

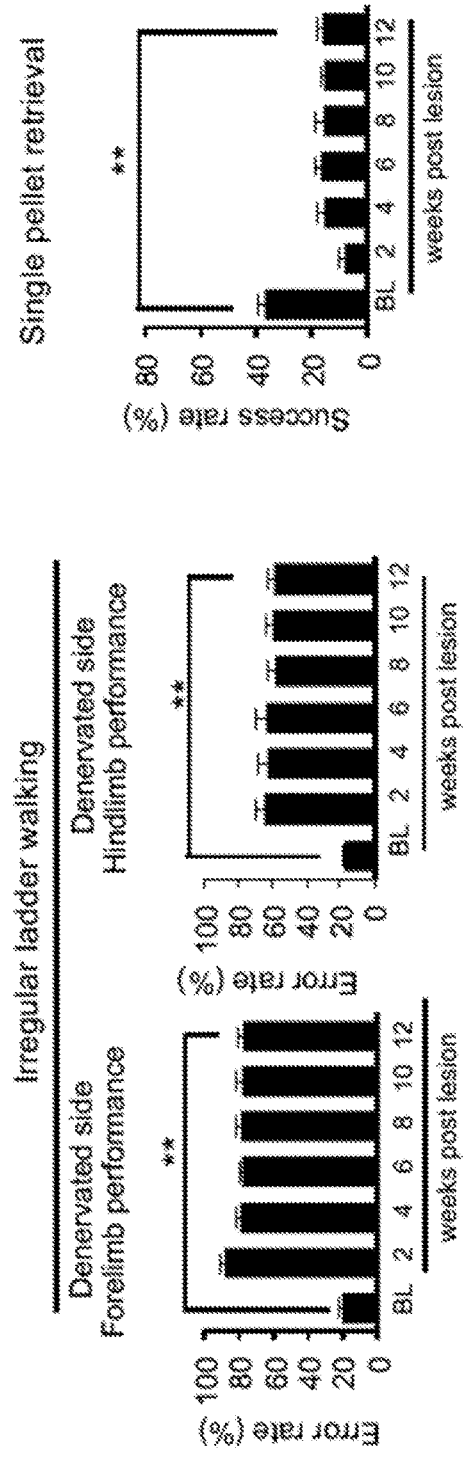
FIG. 12C
FIG. 12D
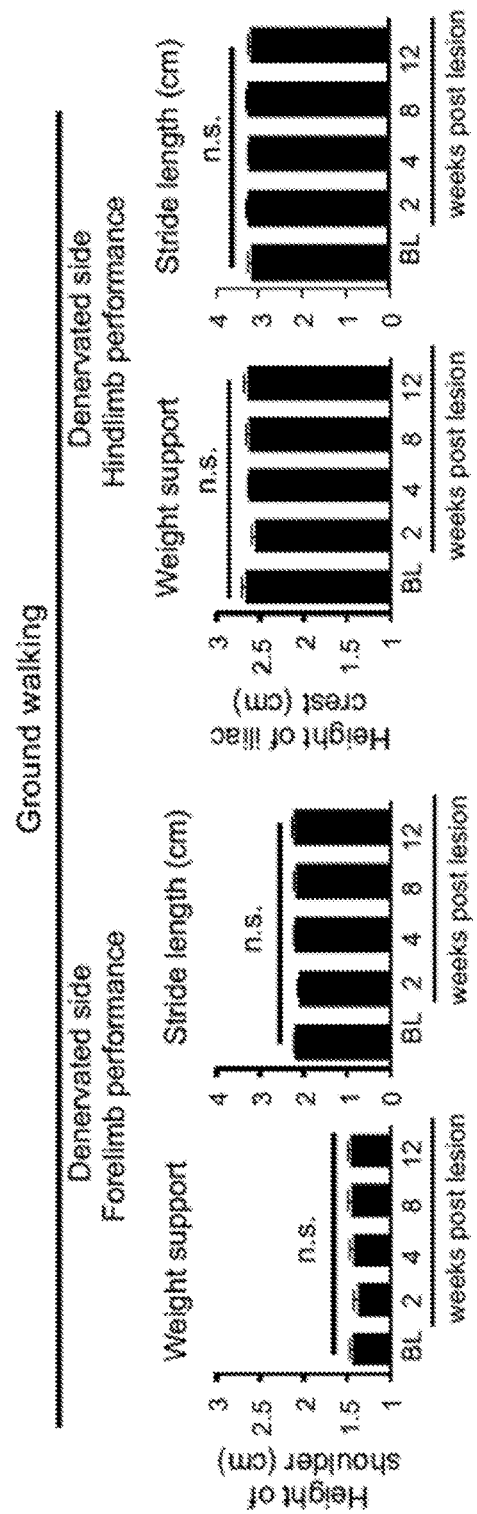
FIG. 12E

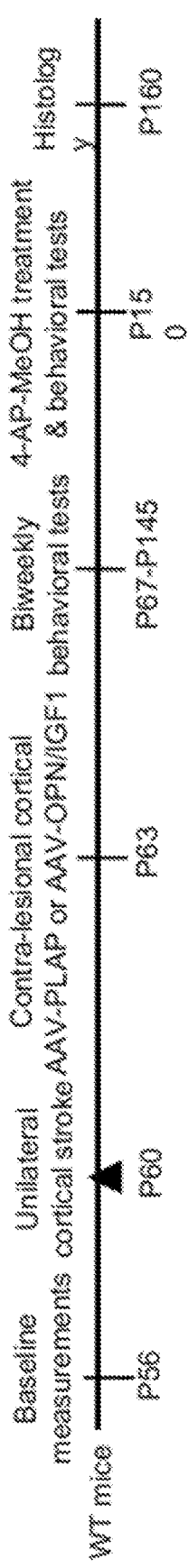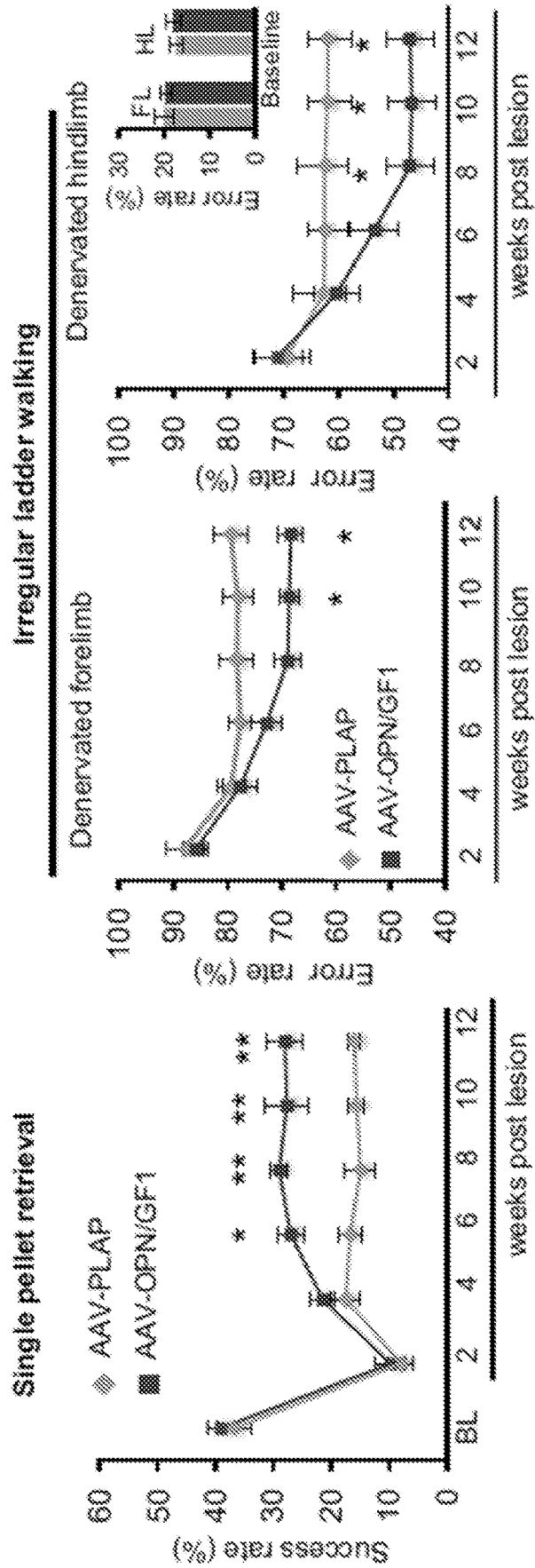
FIG. 13A
FIG. 13B
FIG. 13C

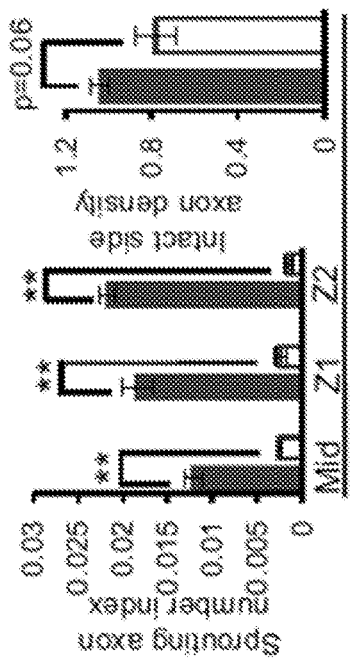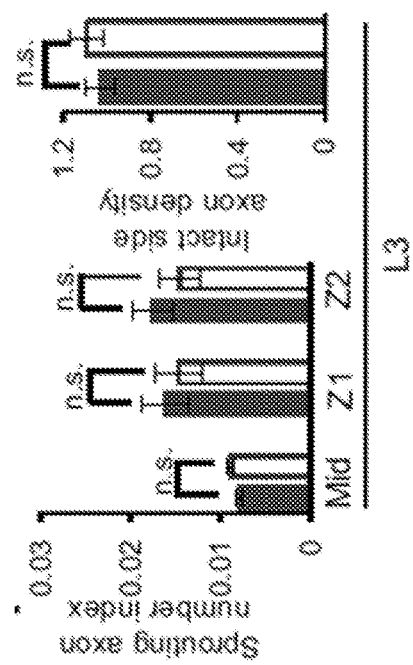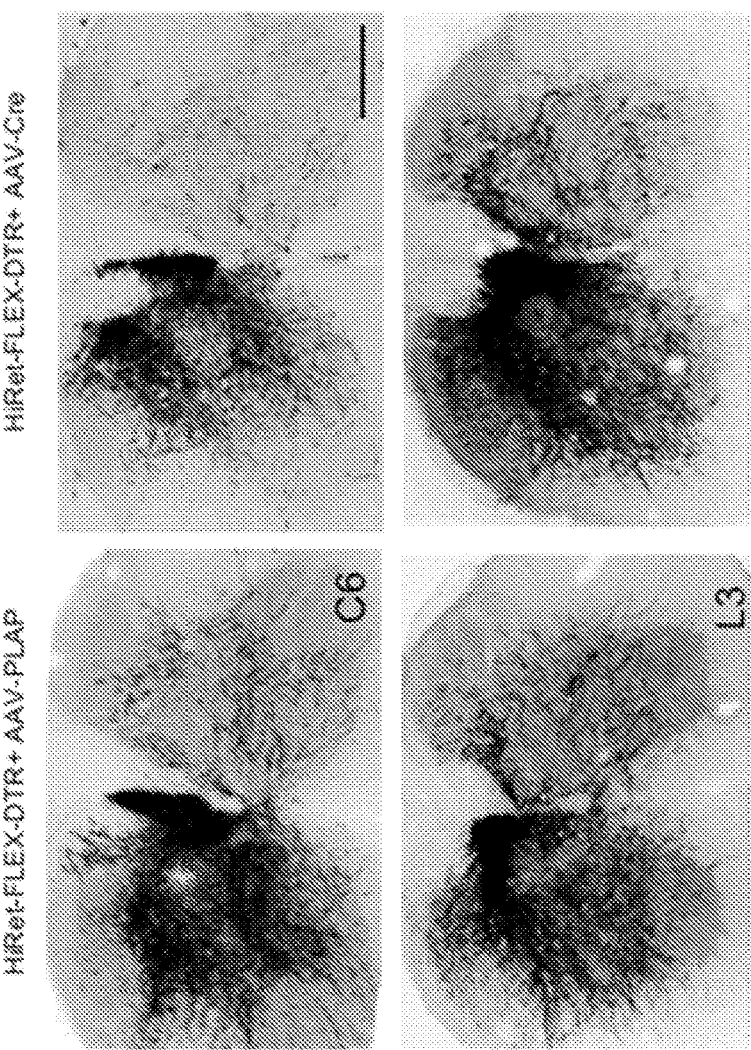
FIG. 16E
FIG. 16F
FIG. 16D

AAV-Control

AAV-fOPN rIGF1

AAV-fOPN + rIGF1 rNGF

AAV-fOPN + rNGF rBDNF

AAV-fOPN + rBDNF rNT3

AAV-fOPN + rNT3

METHODS OF PROMOTING CORTICOSPINAL NEURONAL OUTGROWTH IN NEURONAL LESIONS USING A PRO-REGENERATIVE HUMAN OSTEOPONTIN FRAGMENT

CROSS REFERENCE TO RELATED APPLICATIONS

This application is a 35 U.S.C. § 371 National Phase Entry Application of International Application No. PCT/US18/046436 filed Aug. 13, 2018, which designates the U.S. and claims benefit under 35 U.S.C. § 119(e) of U.S. Provisional Application No. 62/545,772 filed Aug. 15, 2017, the contents of which are incorporated herein by reference in their entireties.

GOVERNMENT SUPPORT

This invention was made with government support under Grant nos. NS029169 and EY021342 awarded by the National Institutes of Health. The government has certain rights in the invention.

FIELD OF THE INVENTION

The field of the invention relates to methods for treating neuronal lesion by promoting neuronal outgrowth.

SEQUENCE LISTING

The instant application contains a Sequence Listing which has been submitted electronically in ASCII format and is hereby incorporated by reference in its entirety. Said ASCII copy, created on Aug. 31, 2018, is named 701039-088710WOPT_SL.txt and is 20,641 bytes in size.

BACKGROUND

In exploring the molecular mechanisms that control the growth ability of corticospinal neurons (CSNs), several important regulators have been identified, such as mTOR/PTEN (Liu et al., 2010; Zukor et al., 2013; Du et al., 2015), STAT3/SOCS3 (Lang et al., 2013; Jin et al., 2015), KLFs (Blackmore et al., 2012) and SoxI1 (Wang et al., 2015). It has been shown that CSNs undergo a development-dependent and injury-triggered decline of mTOR activity and that activating this pathway by inhibiting the expression of its negative regulator PTEN elicits the regrowth of the adult CST after injury (Liu et al., 2010; Zukor et al., 2013; Lewandowski and Steward, 2014; Jin et al., 2015; Danilov and Steward, 2015; Geoffroy et al., 2015). However, because PTEN is a tumor suppressor, clinical application may require other alternative methods to elevate the growth ability of CSNs.

In seeking such alternatives, it is relevant that the PI3K/mTOR pathway plays several roles, one of which is to mediate the activity of neurotrophins and other growth factors. In cultured neonatal CSNs, insulin-like growth factor 1 (IGF1) and brain derived neurotrophic factor (BDNF) are able to promote the growth and branching of CST axons, respectively (Ozdinler and Macklis, 2006). However, direct administration of these factors has limited effects on promoting CST regrowth in adults (Giehl & Tetzlaff, 1996; Lu et al., 2001; Hollins et al., 2009; Li et al., 2010), indicating that in comparison to immature neurons, mature CSNs have reduced responsiveness to growth factors. Hence, it is desirable to develop a sensitizing strategy that enhances the response of mature CSNs to growth factors. A possible means to this end is indicated by recent studies of optic nerve injury (Duan et al., 2015; Bei et al., 2016). It was shown that although IGF1 or BDNF alone failed to promote regeneration, combining either trophic factor with osteopontin (OPN) allowed injured retinal ganglion cells to respond to these growth factors, exhibiting robust axon regeneration in an mTOR-dependent manner (Duan et al., 2015; Bei et al., 2016). However, it remains to be tested whether OPN can sensitize the responses of other types of neurons to these growth factors.

SUMMARY

One aspect of the invention relates to a method of promoting neuronal outgrowth in a subject with a neuronal lesion in their central nervous system. The method comprises administering to the subject an effective amount of a pro-regenerative osteopontin (OPN) fragment and an effective amount of one or both of TGF1 and BDNF, to thereby contact the lesion. In one embodiment, the pro-regenerative OPN fragment is amino acids 1-204 of mouse OPN. In one embodiment, the pro-regenerative OPN fragment is amino acids 1-219 of human OPN. In one embodiment, the pro-regenerative OPN fragment is full length OPN. In one embodiment, the pro-regenerative OPN fragment has 90% homology to any one of the above-discussed fragments.

In one embodiment of all aspects, the method further comprises administering to the subject an effective amount of a voltage gated potassium channel blocker. In one embodiment of all aspects, the voltage gated potassium channel blocker is 4-AP or 4-AP-MeOH.

In one embodiment of all aspects, the subject is an adult.

In one embodiment of all aspects, the neuronal lesion results from spinal cord injury, traumatic brain injury or stroke.

In one embodiment of all aspects, administration results in slow release of the pro-regenerative OPN fragment.

In one embodiment of all aspects, administration begins within 24 hours of the time of lesion development. In another embodiment of all aspects, administration is periodic. In another embodiment of all aspects, administration occurs over a period of at least 8 weeks. In yet another embodiment of all aspects, administration occurs over a period of at least 12 weeks.

In one embodiment of all aspects, administration is localized. In another embodiment of all aspects, administration is directly to the injury site. In yet another embodiment of all aspects, administration is systemic.

Another aspect of the invention relates to a method of treating a subject with a neuronal lesion in their central nervous system comprising administering to the subject an effective amount of a pro-regenerative OPN fragment and an effective amount of one or both of IGF1 and BDNF, to thereby contact the lesion. In one embodiment, the pro-regenerative OPN fragment is amino acids 1-204 of mouse OPN. In one embodiment, the pro-regenerative OPN fragment is amino acids 1-219 of human OPN. In one embodiment, the pro-regenerative OPN fragment is full length OPN. In one embodiment, the pro-regenerative OPN fragment has 90/o homology to any one of the above-discussed fragments.

In one embodiment of all aspects, the method further comprises administering to the subject an effective amount of a voltage gated potassium channel blocker. In one embodiment of all aspects, wherein the voltage gated potassium channel blocker is 4-AP or 4-AP-MeOH.

In one embodiment of all aspects, the subject is an adult.

In one embodiment of all aspects, the neuronal lesion results from spinal cord injury, traumatic brain injury or stroke.

In one embodiment of all aspects, administration results in slow release of the pro-regenerative OPN fragment.

In one embodiment of all aspects, administration begins within 24 hours of the time of lesion development.

In one embodiment of all aspects, administration is periodic. In one embodiment of all aspects, administration occurs over a period of at least 8 weeks. In one embodiment of all aspects, administration occurs over a period of at least 12 weeks. In another embodiment of all aspects, administration is localized. In another embodiment of all aspects, administration is directly to the injury site. In yet another embodiment of all aspects, administration is systemic Another aspect of the invention relates to a pharmaceutical composition comprising a pro-regenerative OPN fragment and a pharmaceutically acceptable excipient. In one embodiment, the pro-regenerative OPN fragment is amino acids 1-204 of mouse OPN. In one embodiment, the pro-regenerative OPN fragment is amino acids 1-219 of human OPN. In one embodiment, the pro-regenerative OPN fragment is full length OPN. In one embodiment, the pro-regenerative OPN fragment has 90% homology to any one of the above-discussed fragments.

In one embodiment of all aspects, the pharmaceutical composition further comprises one or both of IGF1 and BDNF.

In one embodiment of all aspects, the pharmaceutical composition further comprises a voltage gated potassium channel blocker. In one embodiment of all aspects, wherein the voltage gated potassium channel blocker is 4-AP or 4-AP-MeOH.

One aspect of the invention relates to a delivery device comprising a pharmaceutical composition comprising active osteopontin fragment a pro-regenerative OPN fragment and a pharmaceutically acceptable excipient, for delivery of the pharmaceutical composition to a neuronal lesion of a subject. In one embodiment, the pro-regenerative OPN fragment is amino acids 1-204 of mouse OPN. In one embodiment, the pro-regenerative OPN fragment is amino acids 1-219 of human OPN. In one embodiment, the pro-regenerative OPN fragment is full length OPN. In one embodiment, the pro-regenerative OPN fragment has 90/6 homology to any one of the above-discussed fragments.

In one embodiment of all aspects, the pharmaceutical composition further comprises one or both of BDNF and IGF1.

In one embodiment of all aspects, the pharmaceutical composition further comprises a voltage gated potassium channel blocker. In one embodiment of all aspects, the voltage gated potassium channel blocker is 4-AP or 4-AP-MeOH.

In one embodiment of all aspects, the pharmaceutical composition is formulated for slow release of the pro-regenerative OPN fragment.

Definitions

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto. The term "gene product(s)" as used herein refers to include RNA transcribed from a gene, or a polypeptide encoded by a gene or translated from RNA.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker, an "increase" is a statistically significant increase in such level.

The terms "significantly different than", "statistically significant", and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

The term "effective amount" is used interchangeably with the terms "sufficient amount" and "therapeutically effective amount" and refers to the amount of at least one agent, e.g., at dosages and for periods of time necessary to achieve the desired therapeutic result, for example, to increase in a subject. For example, an effective amount using the methods as disclosed herein would be considered as the amount sufficient to increase by at least 10%, at least 20%, at least 30%, at least 40%, at least 50%, at least 60%, at least 70%, at least 90%, at least 99%, as measured by any standard technique. Accordingly, the term "effective amount" or "therapeutically effective amount" as used herein refers to the amount of therapeutic agent (e.g. the pro-regenerative OPN fragment, optionally including BDNF and/or IGF1) of pharmaceutical composition to increase specificity. The dosage administered, as single or multiple doses, to an individual will vary depending upon a variety of factors, including pharmacokinetic properties of the agent, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the agent are outweighed by the therapeutically beneficial effects. The effective amount in each individual case can be determined empirically by a skilled artisan according to established methods in the art and without undue experimentation.

The "pharmaceutical administration" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. The term permits the presence of elements that do not materially affect the basic and novel or functional characteristic(s) of that embodiment of the invention.

As used herein, the term "treating" includes reducing or alleviating at least one adverse effect or symptom of a condition, disease or disorder associated with a CNS lesion. Treating may result in the promotion of a significant amount of neuronal outgrowth in a subject (e.g., at the lesion site). Treating may result in the reduction of a symptom and/or a biochemical marker of such a condition (e.g., by at least 10%). As alternative examples, a detectable reduction in a symptom, for example, an increase in function, mobility, or sensation, (e.g., by 10%).

As used herein, the term neuronal "growth" or "outgrowth" includes the process by which, axons or dendrites extend from a neuron. This is also referred to in the art as neurite outgrowth. The outgrowth can result in a new neuritic projection or in the extension of a previously existing cellular process. Neuronal outgrowth can be measured by the number of neurons extending neuritic projections or processes, or by the length of the linear extensions, or a combination of both. Neuronal growth processes, including neuritogenesis, can be evidenced by GAP-43 expression detected by methods such as immunostaining. "Stimulating neuronal growth" means promoting neuronal outgrowth. Neurite outgrowth or neuritogenesis is meant to encompass outgrowth of a neuron which results in either an axon or a dendrite.

As used herein, the term "CNS neurons" is intended to include the neurons of the brain, eye, the cranial nerves and the spinal cord.

As used herein, the term "administering" to a patient includes dispensing, delivering or applying an active compound in a pharmaceutical formulation to a subject by any suitable route for delivery of the active compound to the desired location in the subject. Administration may be localized or systemic in a subject and includes delivery by either the parenteral or oral route, intramuscular injection, subcutaneous/intradermal injection, intravenous injection, buccal administration, transdermal delivery, use of nanoparticles, use of locally applied matrix containing therapeutic agent, and administration by the rectal, colonic, vaginal, intranasal or respiratory tract route. The agents may, for example, be administered to a comatose, anesthetized or paralyzed subject, or may be administered to a pregnant subject to stimulate axonal growth in a fetus, or in a neonate. Specific routes of administration may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes.

As used herein, the term "intrathecal administration" is intended to include delivering the therapeutic formulation containing the agent (e.g. the pro-regenerative OPN fragment, optionally including BDNF and/or IGF1) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna *magna*" is intended to include the area where the skull ends and the spinal cord begins at the back of the head.

The term "cerebral ventricle" is intended to include the cavities in the brain that are continuous with the central canal of the spinal cord. Administration of the therapeutic formulation to any of the above mentioned sites can be achieved by direct injection of the agent formulation or by the use of infusion pumps. For injection, the therapeutic formulation of the invention can be formulated in liquid solutions, preferably in physiologically compatible buffers such as Hank's solution or Ringer's solution. In addition, the agent formulation may be formulated in solid form and re-dissolved or suspended immediately prior to use. Lyophilized forms are also included. The injection can be, for example, in the form of a bolus injection or continuous infusion (e.g., using infusion pumps) of the inhibitor(s) formulation.

As used herein, the term "contacting CNS neurons" refers to any mode of agent delivery or "administration" either to cells, or to whole organisms in which the agent is capable of exhibiting its pharmacological effect in neurons. "Contacting CNS neurons" is intended to include both in vivo and in vitro methods of bringing an agent of the invention into proximity with a neuron. Suitable modes of administration can be determined by those skilled in the art and such modes of administration may vary between agents. For example, when axonal growth of CNS neurons is stimulated ex vivo, agents can be administered, for example, by transfection, lipofection, electroporation, viral vector infection, or by addition to growth medium.

As used herein, "effective amount" of an agent (e.g. the pro-regenerative OPN fragment, optionally including BDNF and/or IGF1) is an amount sufficient to achieve a desired therapeutic or pharmacological effect, such as an amount sufficient to promote outgrowth/regeneration of CNS neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

A therapeutically effective amount or dosage of an agent is one that results in detectable therapeutic benefit to the individual. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an active compound can include a single treatment or a series of treatments. A therapeutically effective amount may range from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. In one example, a subject is treated with an agent in the range of between about 0.1 to 20 mg/kg body weight, one time per week for between about 1 to 10 weeks, alternatively between 2 to 8 weeks, between about 3 to 7 weeks, or for about 4, 5, or 6 weeks. It will also be appreciated that the effective dosage of an agent used for treatment may increase or decrease over the course of a particular treatment. The agents of the present invention can be administered simultaneously or separately.

As used herein, the term "neurological disorder" is intended to include a disease, disorder, or condition which directly or indirectly affects the normal functioning or anatomy of a subject's nervous system.

As used herein, the term "stroke" is art recognized and is intended to include sudden diminution or loss of consciousness, sensation, and voluntary motion caused by rupture or obstruction (for example, by a blood clot) of an artery of the brain.

As used herein, "traumatic brain injury" is art recognized and is intended to include the condition in which, a traumatic blow to the head causes damage to the brain or connecting spinal cord, often without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

The term "interferes" or "blocks" means that the process or activity is prevented from continuing or being carried out property. Used herein, it described that the endogenous function of the protein is altered in a way that is negative to the outcome of said protein.

As used herein, a "subject" or "patient" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox or wolf. In some embodiments, the subject is a mammal, e.g., a primate, e.g., a human. The terms, "individual," "patient" and "subject" are used interchangeably herein. The subject is preferably a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like). A subject as the term is used herein can refer to a male or a female.

The terms "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein may be easily ascertained by the skilled artisan.

The term "conservative substitution," or "conservative amino acid substitution" when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).)

BRIEF DESCRIPTION OF THE DRAWINGS

FIGS. 1A-1H are experimental results that indicate functional deficits after spinal cord T10 lateral hemisection and hindlimb CSN ablation. (A) Upper: A Cartoon of the T10 lateral hemisection. Lower: A representative transverse section at epicenter of the lesion stained with anti-GFAP. Scale bar: 500 μm. (B) Left: Cartoon of a spinal cord at 1 wk (upper) and 12 wk (bottom) post T10 lateral hemisection. Blue and purple lines represent descending serotonergic and corticospinal tracts, respectively. Right: Representative images of transverse sections of the lumbar spinal cord (L3) at 1 wk (upper lane) and 12 wk (bottom lane) post T10 lateral hemisection stained with anti-5-HT (serotonergic axons, left column) or anti-RFP (corticospinal axons, right column), respectively. To label corticospinal axons, animals received bilateral cortical AAV-ChR2-mCherry injection at 2 wk pre-injury. Scale bar: 500 μm. (C) The fluorescence intensity of 5-HT or mCherry immunostaining at 1 wk and 12 wk post the spinal cord T10 lateral hemisection. All images were acquired using identical optical parameters and scan setting. In each case, the intensities were normalized to 1 wk post injury  and n.s., p<0.01 and no statistical significance respectively. Student's t-test. n=3 mice per group. Five sections at L3 were quantified per mouse. (D-E) Performance on irregular ladder walking post T10 lateral hemisection of the hindlimb from the intact (D) and denervated sides (E).  and n.s.: p<0.01 and no statistical significance, n=7, repeated measures ANOVA followed by post hoc Bonferroni correction. (F) Schematic diagram of the experimental timeline. Emx1-Cre mice were intraspinally (at the spinal cord T12-L4 segments) injected with HiRet-FLEX-DTR (diptheria toxin receptor)/-GFP (control) at P12-P14, measured for behavioral baseline at P56, injected with diptheria toxin (DT, i.p.) at P60, re-measured for behavioral performance at P70, P80, respectively before terminal histological analysis. (G) Representative images of transverse sections of the dorsal spinal cord at cervical (C6) and lumbar (L3 and L5) levels stained with PKCγ in HiRct-GFP (Left column) or HiRet-FLEX-DTR (right column) injected Emx1-Cre mice after DT treatment. Arrowheads indicate the location of the main CST at the dorsal *funiculus*. Open arrowheads indicate ablation of the CST. Scale bar: 500 μm. (H) Performance on irregular ladder walking of the forelimb (upper) and hindlimb (bottom) at −1, 10, and 20 days post DT injection in HiRet-GFP and HiRet-FLEX-DTR injected Emx1-Cre mice. For both forelimb and hindlimb, error rates were averaged from both sides. ** and n.s.: p<0.01 and no statistical significance, Student's t test, n=6, 5 for HiRet-GFP or HiRet-FLEX-DTR injected mice, respectively.

FIGS. 2A-2L present experimental results that indicate partial functional recovery after T10 lateral hemisection. (A) Representative images of the lumbar spinal cord in animals with T10 lateral hemisection with post-lesional cortical injection of AAV-PLAP. AAV-ChR2-mCherry and AAV-ChR2-YFP were injected at the ipsi-lesional and contra-lesional cortexes. From left to right, examples of complete, incomplete and over-lateral spinal hemisection Arrowheads indicated the locations (bilateral) of the main CST tract. Notice for incomplete hemisection: the YFP+ CST axons were spared at the injured side in the lumbar spinal cord. For over hemisection; the mCherry+ CST axons were significantly reduced at the "uninjured" side in the lumbar spinal cord. Scale bar: 500 μm. (B-G) Kinematic measurements of weight support (B), denervated side hindlimb retraction (C) and protraction (D), inter-hindlimb coordination (E, F) and forelimb-hindlimb coordination (G) during overground walking at pre- and 1, 2, 4, 8, and 12 wk post T10 lateral hemisection. (H) Inter-hindlimb coordination during swimming at pre- and 1, 2, 4, 8, and 12 wk post T10 lateral hemisection. (I-J) Speed tolerance (I) and denervated side hindlimb dragging at maximal tolerated speed (J) during treadmill walking at pre- and 1, 2, 4, 8, and 12 wk post T10 lateral hemisection. For (B-J): **, *, and n s.: p<0.01, p<0.05 and no statistical significance, respectively. n=7, Repeated one-way ANOVA, followed by Bonferroni post hoc correction. (K-L) Breakdown of hindpaw hit, miss and slips on the irregular ladder walking at 1 wk and 12 wk post T10 lateral hemisection of the hindlimbs from the intact (K) and denervated (L) sides. Hit stands for correct placement. Miss indicates when a paw completely misses the ladder rung, and Slip indicates that a paw contacted a ladder rung but fell through the gap.

FIGS. 4A-4H present experimental results that indicate gross, but not skilled, locomotion was unperturbed in hindlimb CSN ablated mice. (A-D) Gross locomotor function [weight support (A), hindlimb protraction (B) and retraction (C), inter-limb coordination (D)] measured at −1, 10, and 20 d post DT injection in HiRet-GFP (control) and HiRet-FLEX-DTR injected animals at time points indicated after DT injection. (E-G) Performance on treadmill walking. Speed tolerance (E) was measured at −1, 10, and 20 d post DT injection in control and HiRet-FLEX-DTR injected mice. Stance duration (F) with representative stick views of hindlimb movement (G) at various speeds in control and HiRet-FLEX-DTR mice at 20 d post DT injection. Notice no overt hindlimb dragging in either control or HiRet-FLEX-DTR injected mice at speeds of 10 or 20 cm·s-1 on treadmill. Student's t-test n.s.: no statistical significance. n=6 and 5 for control and HiRet-FLEX-DTR injected animals respectively (H) Percentage of hindpaw placement categories on irregular ladder walking at pre (−1 d) and post (20 d) DT injection in HiRet-GFP or HiRet-FLEX-DTR injected animals.

FIGS. 12A-12E present experimental results that indicate characterization of unilateral photothrombotic stroke. (A) Schematic paradigm showing the light covered areas (primary sensoromotor cortex) of the unilateral photothrombotic stroke. *, position of the bregma, RFA, CFA and HL SI/MI (Tennant et al., 2011; Ayling et al., 2009): rostral forelimb area, caudal forelimb area and hindlimb primary somatosensory/motor area. (B) Representative images of TTC (Left column) or Nissl (right column) staining of coronal sections [bregma 0.14 (upper lane); bregma −0.46 (bottom lane)] showing the lesion (dashed line in Nissl staining) across the primary sensoromotor cortex (M I/SI). Scale bar: 1 mm. (C-D) Performance of irregular ladder walking (C) and single pellet retrieval (D), respectively following photothrombotic stroke. **, p<0.01, One-way ANOVA with Bonferroni post hoc correction (n=7). (E) Kinematic measurements of weight support and stride length of both forelimb and hindlimb from the denervated side during overground walking, n.s., no statistical significance, One way ANOVA (n=7).

FIGS. 13A-13D present experimental results that indicate OPN/IGF1 treatment improves skilled locomotion after unilateral cortical stroke. (A) Schematic diagram of the experimental timeline. Wild type mice received baseline behavioral training at P56, unilateral cortical photothrombotic stroke at P60, unilateral cortical injection (the intact side) of AAV-PLAP or AAV-OPN/IGF1 at P63, biweekly behavioral tests from P67-P145 before terminal histological analysis. (B-C) Performance on single pellet retrieval task (B) and irregular ladder walking (C) respectively. * and **, p<0.05 and p<0.01, Repeated measures ANOVA with Bonferroni post hoc correction, n=8, 9 for AAV-PLAP, AAV-OPN/IGF1 injected animals. (D) Performance on single pellet retrieval task and irregular walking in AAV-PLAP and AAV-OPN/IGF1 treated groups with systematic administration of 4-AP-MeOH. *, p<0.05, Student's t-test. n=8, 9 for AAV-PLAP, AAV-OPN/IGF1 injected animals.

FIGS. 16A-16F present experimental results that indicate ablation of sprouted CSNs abolishes recovered skilled locomotor performance. (A) Schematic drawing of the experimental procedure. Mice that received AAV-OPN/IGF1 treatment after stroke were subjected to intraspinal lentivirus (HiRet-FLEX-DTR) injection on the denervated side of the cervical spinal cord (C5-C7) at P160 (1), and cortical AAV-Cre (ablation) or AAV-PLAP (control) injection (intact side) at P163 (2). At P175, DT was administrated (i.p.) (3).(B. C) Performance on the single pellet retrieval task (B) and irregularly horizontal ladder (C), respectively. Notice that for irregular horizontal ladder walking test, the performance of both intact and denervated sides of forelimbs and hindlimbs was analyzed. *, p<0.01 or 0.05, n.s., not significant, Student's t-test, n=6 and 5 for AAV-Cre (ablation) or AAV-PLAP (control) injected group, respectively. (D) Representative images of transverse spinal cord sections at C6 and L3 immunostained with anti-RFP to label the CST axons originated from the intact side in cortical AAV-PLAP (control) or AAV-Cre (ablation) injected animals. Scale bar: 500 μm. (E-F) Quantification of midline crossing axons (left) and axon density of the intact side (right) in the cervical (E) and lumbar (F) spinal cord (C6 & L3) in cortical AAV-PLAP (control) or AAV-Cre (ablation) injected groups **, p=0.06, and n s.: p<0.01, borderline p value, and no statistical significance, respectively. Student's t-test. n=3 mice per group. Five serial sections at C6 and L3 were quantified per mouse.

DETAILED DESCRIPTION

Figure 1C:
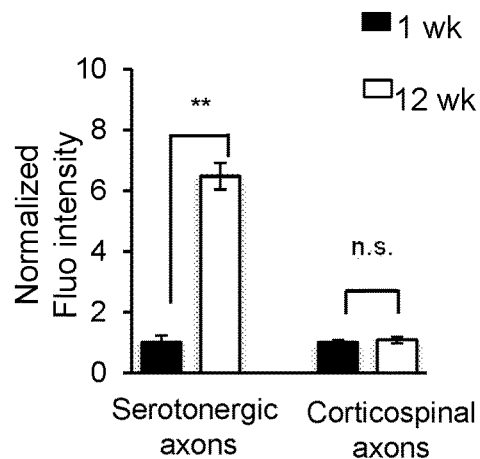

A major hurdle for functional recovery after both spinal cord injury and cortical stroke is the limited regrowth of the axons in the corticospinal tract (CST) that originate in the motor cortex and innervate the spinal cord. Methods and compositions described herein are based in part on the discovery of a region of the osteopontin protein that is necessary and sufficient for conferring neuroregenerative properties. Administration of an osteopontin fragment containing this region (a pro-regenerative OPN fragment) is sufficient to promote neuronal outgrowth in an animal following neuronal injury.

Accordingly, one aspect of the invention described herein relates to a method for promoting neuronal outgrowth in a subject with a neuronal lesion in their central nervous system, the method comprising administering to the subject an effective amount of a pro-regenerative OPN fragment and an effective amount of one or both of IGF1 and BDNF, to thereby contact the lesion. A neuronal lesion can be caused by a spinal cord injury, a traumatic brain injury, or a stroke. Methods for identifying a neuronal lesion are described herein. In one embodiment, the method further comprises administering a voltage gated potassium channel blocker. Non-limiting examples of such voltage gated potassium channel blocker include 4-AP or 4-AP-MeOH.

In one embodiment, administering of the pro-regenerative OPN fragment to a subject occurs within a recent time frame of the injury. Examples of such time frames, include, without limitation, contacting within 12 hours following the injury. Other such time frames are contacting the neuron within 24, 36, and 48 hours of the injury. Other such time frames are contacting the neuron within 1, 2, 3, 4, 5, 6, and 7 days of the injury. Administering at a later point following the injury may also have some benefit. Administering can be localized, systemic, or directly at the injury site. Administering can be periodic, ongoing or repeated, following the initial contact. Method of promoting the required contact (e.g., in a subject) are described herein. In one embodiment, administration results in the slow release of the pro-regenerative OPN fragment.

Another aspect of the invention described herein relates to a method of treating neuronal lesion in the central nervous system, the method comprising administering to a subject an effective amount of a pro-regenerative OPN fragment and an effective amount of one or both of IGF1 and BDNF, to thereby contact the lesion. In one embodiment, the method further comprises administering to a subject a voltage gated potassium channel blocker. In one embodiment, the voltage gated potassium channel blocker is 4-AP or 4-AP-MeOH. In one embodiment, the administration results in the slow release of the pro-regenerative OPN fragment.

In one embodiment, administering of the pro-regenerative OPN fragment to a subject occurs within a recent time frame of the injury. Examples of such time frames, include, without limitation, contacting within 12 hours following the injury. Other such time frames are contacting the neuron within 24, 36, and 48 hours of the injury. Other such time frames are contacting the neuron within 1, 2, 3, 4, 5, 6, and 7 days of the injury. Administering at a later point following the injury may also have some benefit. Administering can be localized, systemic, or directly at the injury site. Administering can be periodic, ongoing or repeated, following the initial contact. Method of promoting the required contact (e.g., in a subject) are described herein. In one embodiment, administration results in the slow release of the pro-regenerative OPN fragment.

Another aspect of the invention relates to a pharmaceutical composition, the pharmaceutical composition comprising a pro-regenerative OPN fragment (optionally including BDNF and/or IGF1) and a pharmaceutically acceptable excipient. In one embodiment, the pharmaceutical composition further comprises one or both IGF1 and BDNF. In one embodiment, the pharmaceutical composition further comprises a voltage gated potassium channel blocker. In one embodiment, the voltage gated potassium channel blocker is 4-AP or 4-AP-MeOH. In another embodiment, the pharmaceutical composition is formulated for slow release.

Another aspect of the invention relates to a delivery device for delivery of the pharmaceutical composition comprising a pro-regenerative OPN fragment (optionally including BDNF and/or IGF1) described herein to a neuronal lesion of a subject.

Another aspect of the invention relates to a kit comprising the pro-regenerative OPN fragment, optionally including BDNF and/or IGF1. The various components may be in a container or in separate containers. The kit may comprise a delivery device for delivery of the pharmaceutical composition comprising a pro-regenerative OPN fragment (optionally including BDNF and/or IGF1) described herein to a neuronal lesion of a subject.

Osteopontin (OPN)

OPN, also known as secreted phosphoprotein 1 (SPP1), is a highly negatively charged, extracellular matrix protein that lacks an extensive secondary structure. OPN has diverses cellular roles dependent on the biological system. In bone, OPN is an important factor in bone remodeling anchoring osteoclasts to the bone mineral matrix. OPN is expressed in a range of immune cells and acts as an immune modulator. In addition, OPN inhibits production of Th2 cytokine IL-10, which leads to an enhanced Th1 response. OPN has a role in chemotaxis, as it has been implicated in recruited neutrophil in alcoholic liver disease. Finally, OPN has been shown to play an important anti-apoptoic role in several biological systems.

OPN sequences are known for a number of species, e.g., human OPN (NCBI Gene ID: 6696) and mRNA (NCBI Ref Seq NM_000582.2). OPN can refer to human OPN, including naturally occurring variants and alleles thereof. Homologs and/or orthologs of human OPN are readily identified for such species by the skilled practitioner, e.g., using the NCBI ortholog search function or searching available sequence data for a given species for sequence similar to a reference OPN sequence. Preferably, the origin of the OPN or fragment is the same as the species to which it is administered.

The sequence of full length mouse OPN is 294 amino acids in length, the sequence of which is shown below:

(SEQ ID NO: 1)
MRLAVICFCL FGIASSLPVK VTDSGSSEEK LYSLHPDPIA

TWLVPDPSQK QNLLAPQNAV SSEEKDDFKQ ETLPSNSNES

HDHMDDDDDD DDDDGDHAES EDSVDSDESD ESHHSDESDE

TVTASTQADT FTPIVPTVDV PNGRGDSLAY GLRSKSRSFQ

VSDEQYPDAT DEDLTSHMKS GESKESLDVI PVAQLLSMPS

DQDNNGKGSH ESSQLDEPSL ETHRLEHSKE SQESADQSDV

IDSQASSKAS LEHQSHKFHS HKDKLVLDPK SKEDDRYLKF

RISHELESSS SEVN

The sequence of full length human OPN is 314 amino acids in length, the sequence of which is shown below:

(SEQ ID NO: 2)
MRIAVICFCL LGITCAIPVK QADSGSSEEK QLYNKYPDAV

ATWLNPDPSQ KQNLLAPQNA VSSEETNDFK QETLPSKSNE

SHDHMDDMDD EDDDDHVDSQ DSIDSNDSDD VDDTDDSHQS

DESHHSDESD ELVTDFPTDL PATEVFTPVV PTVDTYDGRG

DSVVYGLRSK SKKFRRPDIQ YPDATDEDIT SHMESEELNG

AYKAIPVAQD LNAPSDWDSR GKDSYETSQL DDQSAETHSH

KQSRLYKRKA NDESNEHSDV IDSQELSKVS REFHSHEFHS

HEDMLVVDPK SKEEDKHLKF RISHELDSAS SEVN

As described herein, a pro-regenerative fragment of OPN is a polypeptide fragment of OPN that retains a substantial amount of the neurological pro-regenerative activity of full length OPN. In one embodiment, the pro-regenerative fragment is mouse OPN (e.g., amino acids 1-204). In one embodiment, the pro-regenerative fragment contains at least 1-204 amino acids of mouse OPN. In one embodiment, the pro-regenerative fragment is human OPN (e.g., amino acids 1-219). In one embodiment, the pro-regenerative fragment contains at least 1-219 amino acids of human OPN. In one embodiment the pro-regenerative fragment of OPN is full length OPN (e.g., human or mouse).

In one embodiment, the pro-regenerative mouse OPN fragment (mouse N-OPN$_{1-204}$) has the amino acid sequence shown below:

(SEQ ID NO: 3)
MRLAVICFCLFGIASSLPVKVTDSGSSEEKLYSLHPDPIATTWLVPDPSQK

QNLLAPQNAVSSEEKDDFKQETLPSNSNESHDHMDDDDDDDDDGDHAESE

DSVDSDESDESHHSDESDETVTASTQADTFTPIVPTVDVPNGRGDSLAYGL

RSKSRSFQVSDEQYPDATDEDLTSHMKSGESKESLDVIPVAQLLSMPSDQD

N

In one embodiment, the pro-regenerative human OPN fragment (human N-OPN$_{1-219}$) has the amino acid sequence shown below:

(SEQ ID NO: 4)
MRIAVICFCLLGITCAIPVKQADSGSSEEKQLYNKYPDAVATWLNPDPSQK

QNLLAPQNAVSSEETNDFKQETLPSKSNESHDHMDDMDDEDDDDHVDSQDS

IDSNDSDDVDDTDDSHQSDESHHSDESDELVTDFPTDLPATEVFTPVVPTV

DTYDGRGDSVVYGLRSKSKKFRRPDIQYPDATDEDITSHMESEELNGAYKA

IPVAQDLNAPSDWDS

Table 1 shows the conservation of mouse and human OPN: these proteins share a 62% identity. For both mouse and human OPN, the first 16 amino acids are cleaved in vivo to produce mature Osteopontin protein. In light of this, in one embodiment, the pro-regenerative mouse OPN fragment is amino acids 17-204 of the (mouse N-OPN$_{17-204}$).

In one embodiment mouse OPN$_{17-204}$ has the amino acid sequence:

(SEQ ID NO: 5)
LPVKVTDSGSSEEKLYSLHPDPIATWLVPDPSQKQNLLAPQNAVSSEEKDD

FKQETLPSNSNESHDHMDDDDDDDDDGDHAESEDSVDSDESDESHHSDES

DETVTASTQADTFTPIVPTVDVPNGRGDSLAYGLRSKSRSFQVSDEQYPDA

TDEDLTSHMKSGESKESLDVI PVAQLLSMPSDQDN

In one embodiment, the pro-regenerative human OPN fragment is amino acids 17-219 of the (human N-OPN$_{17-219}$). In one embodiment human OPN$_{17-219}$ has the amino acid sequence:

(SEQ ID NO: 6)
IPVKQADSGSSEEKQLYNKYPDAVATWLNPDPSQKQNLLAPQNAVSSEETN

DFKQETLPSKSNESHDHMDDMDDEDDDDHVDSQDSIDSNDSDDVDDTDDSH

QSDESHHSDESDELVTDFPTDLPATEVFTPVVPTVDTYDGRGDSVVYGLRS

KSKKFRRPDIQYPDATDEDITSHMESEELNGAYKAIPVAQDLNAPSDWDS

In one embodiment, the pro-regenerative fragment is either mouse N-OPN$_{17-204}$ or human N-OPN$_{1-219}$ having one or more conservative amino acid substitutions that preserve the pro-regenerative activity. In one embodiment, the pro-regenerative fragment has at least 90% homology to either mouse N-OPN$_{17-204}$ or human N-OPN$_{17-219}$ or mouse N-OPN$_{1-204}$ or human N-OPN$_{1-219}$.

Table 1: Comparison of mouse and human N-OPN fragments. In Table 1, Query is SEQ ID NO: 9 and Sbjct is SEQ ID NO: 10.

TABLE 1

Comparison of mouse and human N-OPN fragments. In Table 1, Query is SEQ ID
NO: 9 and Sbjct is SEQ ID NO: 10.

```
                 Range 1:1 to 314 Graphics                ▼Next Match   ▲Previous Match Score         Expect Method                 Identities    Positives         Gaps
327  bits(839) 3e-117 Compositional matrix adjust. 195/314(62%) 231/314(73%) 20/314(6%)

Query    1    MRLAVICFCLFGIASSLPVKVIDSGSSEEK-LYSLEPDPIATWLVPDPSQKQNLLAPQNA        59
              MR+AVICFCL GI  ++PVK  DSGSSEEK LY+ +PD +ATWL PDPSQKQNLLAPQNA
Sbjct    1    MRIAVICFCLLGITCAIPVKQADSGSSEEKQLYNKYPDAVATWLNPDPSQKQNLLAPQNA        60

Query   60    VSSEEKDDFKQETLPENSNESHDHMDDDDDDDDDGDHASSEDSVDSQ----------ES       109
              VSSEE +DFKQETLPS SNESEDHMDD DD+DDDD    ++       +           +S
Sbjct   61    VSSEETNDFKQETLPSKSNESEDHMDDMDDEDDDDHVDSQDSIDSNDSDDVDDTDDSHQS      120

Query  110    DESEESDESDETVTAST----QADTFTPIVPTVDVPNGRGDSLAYGLRSKSRSFQVSDEQ      165
              DESHESDESDE VT       + FTP+VPTVD  +GRGDS+ YGLRSKS+ F+  D O
Sbjct  121    DESEESDESDELVTDFPTDLPATEVFTPVVPTVDTYDGRGDSVVYGLRSKSKKFRRFDIQ      180

Query  166    YPDATDEDLTSEMESGESKESLDVIPVAQLLSMPSDQONNGKGSKESSQLDEPSLETH--      223
              YPDATDED+TSEM+S E    +    IPVAG L+ PSD D+ GK S+E+SQLD+ S ETS
Sbjct  181    YPDATDEDITSHMESEELNGAYKAIPVAQDLNAPSDWDSRGKDSYETSQLDDQSAEYHSH      246

Query  224    ---RLEHSKESQESADQSDVIDSQASSKASLEHQSEKFESHKDKLVLDFKSKEDDRILKF      280
                 RL   K + ES + SDVIDSQ   SK S E   SE+FESH+D LV+DPKSKE+D++LKF
Sbjct  241    KQSRLYKRKANSESNESSSVIDSQELSKVSREFHSEEFESHEDMLVVBPKSKEEDKRLKF      300

Query  281    RISEELESSSSEVN                                                   294
              RISHEL+S+SSEVN
Sbjct  301    RISEELDSASSEVN                                                   314
```

Additional Agents for Administration

In some embodiments, a subject is administered insulin-like growth factor 1 (IGF1) with the pro-regenerative OPN fragment. IGF1 is a hormone similar in molecular structure to insulin. IGF1 is important in adolescent growth and displays anabolic effects in adults. IGF1 is a primary mediator of the effects of growth hormone (GH). Growth hormone is made in the anterior pituitary gland, is released into the blood stream, and then stimulates the liver to produce IGF1. IGF1 then stimulates systemic body growth, and has growth-promoting effects on almost every cell in the body, especially skeletal muscle, cartilage, bone, liver, kidney, nerves, skin, hematopoietic cell, and lungs. In addition to the insulin-like effects, IGF1 can also regulate cell growth and development, especially in nerve cells, as well as cellular DNA synthesis.

IGF1 is mediated by binding to its specific receptor, the insulin-like growth factor 1 receptor (IGF1R). Binding to the IGF1R, a receptor tyrosine kinase, initiates intracellular signaling; IGF1 is a potent activator of the AKT signaling pathway, a stimulator of cell growth and proliferation, and a potent inhibitor of programmed cell death. IGF1 additionally binds to the insulin receptor. IGF1 has been shown to bind and interact with all the IGF1 binding proteins (IGFBPs), of which there are seven: IGFBP1, IGFBP2, IGFBP3, IGFBP4, IGFBP5, IGFBP6, and IGFBP7. Some IGFBPs are inhibitory, for example, both IGFBP-2 and IGFBP-5 bind IGF1 at a higher affinity than it binds its receptor. Therefore, increases in serum levels of these two IGFBPs result in a decrease in IGF1 activity.

IGF1 sequences are known for a number of species, e.g., human IGF1 (NCBI Gene ID: 3479) and mRNA (NCBI Ref Seq NM_000618.4). IGF1 can refer to human IGF1, including naturally occurring variants and alleles thereof. Homologs and/or orthologs of human IGF1 are readily identified for such species by the skilled practitioner, e.g., using the NCBI ortholog search function or searching available sequence data for a given species for sequence similar to a reference IGF1 sequence.

In some embodiments, a subject is administered brain-dervived neurotrophic factor (BDNF) combined with the pro-regenerative OPN fragment. BDNF is a member of the neurotrophin family of growth factors, and is localized to the brain and its periphery. BDNF acts on certain neurons of the central nervous system and the peripheral nervous system to support the survival of existing neurons, and encourage the growth and differentiation of new neurons and synapses. In the brain, it is active in the hippocampus, cortex, and basal forebrain; areas vital to learning and memory.

Neurotrophins are proteins that help to stimulate and control neurogenesis, BDNF being one of the most active. Mice born without the ability to make BDNF suffer developmental defects in the brain and sensory nervous system, and die soon after birth, indicating that BDNF plays an important role in normal neural development.

BDNF is made in the endoplasmic reticulum and secreted from dense-core vesicles. It binds carboxypeptidase E (CPE), and the disruption of this binding has been proposed to cause the loss of sorting of BDNF into dense-core vesicles. Certain types of physical exercise have been shown to markedly (threefold) increase BDNF synthesis in the human brain, a phenomenon which is partly responsible for exercise-induced neurogenesis and improvements in cognitive function.

BDNF sequences are known for a number of species, e.g., human BDNF (NCBI Gene ID: 627) and mRNA (NCBI Ref Seq NM_001143805.1). BDNF can refer to human BDNF, including naturally occurring variants and alleles thereof. Homologs and/or orthologs of human BDNF are readily identified for such species by the skilled practitioner, e.g., using the NCBI ortholog search function or searching available sequence data for a given species for sequence similar to a reference BDNF sequence.

In some embodiments, a voltage gated potassium channel blocker is administered with the pro-regenerative OPN fragment (optionally with BDNF and/or IGF1). A voltage gated potassium channel is a transmembrane channels specific for potassium and sensitive to voltage changes in the cell's membrane potential. During action potentials, they play a crucial role in returning the depolarized cell to a resting state. The channel is made up of multiple alpha and beta subunits, and is selective for potassium. Blocking a voltage gated potassium channel prolongs the duration of action potentials and increases acetylcholine release at the neuromuscular junction. Examples of voltage gated potassium channel blockers include, but are not limited to 2-Aminopyridine (4-AP), 4-AP-MeOH, dendrotoxins, ADWX1, Agitoxin 2, AM 92016 hydrochloride, AmmTX3, Astemizole, BAPTA AM, BDS1, BeKm1, Chromanol 293B, Dofetilide, DPO-1, E-4031 dihydrochloride, Guangxitoxin 1E, HMR1556, JNJ 303, Kaliotoxin, KN 92, KN 93, Linopirdine dihydrochloride, Margatoxin, ProTx1, Psora 4, RuBi-4AP, ShK-Dap22, Terfenadine, Tetraethylammonium chloride, UK 78282 hydrochloride, and XE 991 dihydrochloride.

Efficacy of Treatment

The ability of a therapeutic agent to produce neuronal outgrowth of CNS neurons in a subject may be assessed using any of a variety of known procedures and assays. For example, the ability of a therapeutic agent to re-establish neural connectivity and/or function after a CNS injury, may be determined histologically (either by slicing neuronal tissue and looking at neuronal branching, or by showing cytoplasmic transport of dyes). Therapeutic agents may also be assessed by monitoring the ability of the agent to fully or partially restore the electroretinogram after damage to the neural retina or optic nerve; or to fully or partially restore a pupillary response to light in the damaged eye.

Other tests that may be used to determine the ability of a therapeutic agent to produce neuronal outgrowth in a subject include standard tests of neurological function in human subjects or in animal models of spinal injury (such as standard reflex testing, urologic tests, urodynamic testing, tests for deep and superficial pain appreciation, propnoceptive placing of the hind limbs, ambulation, and evoked potential testing). In addition, nerve impulse conduction can be measured in a subject, such as by measuring conduct action potentials, as an indication of the production of a neurosalutary effect.

Animal models suitable for use in the assays of the present invention include the rat model of partial transaction (described in Weidner et al., (2001) Proc Natl Acad Sci USA 98:3513-3518). This animal model tests how well a compound can enhance the survival and sprouting of the intact remaining fragment of an almost fully-transected cord. Accordingly, after administration of a candidate agent these animals may be evaluated for recovery of a certain function, such as how well the rats may manipulate food pellets with their forearms (to which the relevant cord had been cut 97%).

Another animal model suitable for use in the assays of the present invention includes the rat model of stroke as described by Kawamata et al., ((1997) Proc Natl Acad Sci USA 94:8179-8184), which describes in detail various tests that may be used to assess sensor motor function in the limbs as well as vestibulomotor function after an injury. Administration to these animals of the agents described herein can be used to assess whether a given compound, route of administration, or dosage results in neuronal outgrowth or a neurosalutary effects, such as increasing the level of function, or increasing the rate of regaining function or the degree of retention of function in the test animals.

Standard neurological evaluations used to assess progress in human patients after a stroke may also be used to evaluate the ability of a therapeutic agent to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

Forms of Administration

The therapeutic agents described herein can be delivered to the subject in a variety of forms. In one embodiment, one or more polypeptides are administered corresponding to the therapeutic agents. The polypeptides can further contain additional amino acid sequences (heterologous to the active agents) such that the active agent is delivered in the form of a fusion protein. In one embodiment, vectors containing nucleic acids encoding the therapeutic agents in expressible form are delivered to the subject. Examples of nucleic acids encoding OPN are provided herein.

The coding region of full length human OPN is shown below and can be found within the human OPN gene, Gene ID: 6696, transcript variant 1.

(SEQ ID NO: 7)
atgag aattgcagtg atttgctttt gcctcctagg catcacctgt gccataccag ttaaacaggc tgattctgga agttctgagg aaaagcagct ttacaacaaa tacccagatg ctgtggccac atggctaaac cctgacccat ctcagaagca gaatctccta gccccacaga atgctgtgtc ctctgaagaa accaatgact ttaaacaaga gacccttcca agtaagtcca acgaaagcca tgaccacatg gatgatatgg atgatgaaga tgatgatgac catgtggaca gccaggactc cattgactcg aacgactctg atgatgtaga tgacactgat gattctcacc agtctgatga gtctcaccat tctgatgaat ctgatgaact ggtcactgat tttcccacgg acctgccagc aaccgaagtt ttgtccccac agtagacaca tatgatggcc gaggtgatag tgtggtttat ggactgaggt caaaatctaa gaagtttcgc agacctgaca tccagtaccc tgatgctaca gacgaggaca tcacctcaca catggaaagc gaggagttga atggtgcata caaggccatc cccgttgccc aggacctgaa cgcgccttct gattgggaca gccgtgggaa ggacagttat agctggatga ccagagtgct gaaacccaca gccacaagca gtccagatta tataagcgga aagccaatga tgagagcaat gagcattccg atgtgattga tagtcaggaa ctttccaaag tcagccgtga attccacagc catgaatttc acagccatga agatatgctg gttgtagacc ccaaaagtaa ggaagaagat aaacacctga aatttcgtat ttctcatgaa ttagatagtg catcttctga ggtcaattaa Coding region of full length mouse OPN is shown below and can be found within the mouse OPN gene, Gene ID: 20750, transcript variant 5.

(SEIQ ID NO: 8)
```
atg agattggcag tgatttgctt ttgcctgttt ggcattgcct cctcctccc ggtgaaagtg actgattctg gcagctcaga ggagaagctt tacagcctgc acccagatcc tatagccaca tggctggtgc ctgacccatc tcagaagcag aatctccttg cgccacagaa tgctgtgtcc tctgaagaaa aggatgactt taagcaagaa actcttccaa gcaattccaa tgaaagccat gaccacatgg acgacgatga tgacgatgat gatgacgatg gagaccatgc agagagcgag gattctgtgg actcggatga atctgacgaa tctcaccatt cggatgagtc tgatgagacc gtcactgcta gtacacaagc agacactttc actccaatcg tccctacagt cgatgtcccc aacggccgag gtgatagctt ggcttatgga ctgaggtcaa agtctaggag tttccaggtt tctgatgaac agtatcctga tgccacagat gaggacctca cctctcacat gaagagcggt gagtctaagg agtccctcga tgtcatccct gttgcccagc ttctgagcat gccctctgat caggacaaca acggaaaggg cagccatgag tcaagtcagc tggatgaacc aagtctggaa acacacagac ttgagcattc caaagagagc caggagagtg ccgatcagtc ggatgtgatc gatagtcaag caagttccaa agccagcctg gaacatcaga gccacaagtt tcacagccac aaggacaagc tagtcctaga ccctaagagt aaggaagatg ataggtatct gaaattccga atttctcatg aattagagag ttcatcttct gaggtcaact aa
```

Expression Vectors

The nucleic acid molecules of the invention can be present in the context of an expression vector and/or a cloning vector. Such vectors are typically specifically designed for the host cell in which they are to be used (e.g., prokaryotic, eukaryotic or both).

Expression vector may be, for example, plasmid or virus vectors, and typically contain an origin of replication, a promoter and a regulator of the promoter. The recombinant expression vector may then be used to transform or transfect suitable host cells such as bacterial cells, e.g. $E.$ $coli$ cells, or eukaryotic cells such as yeast, insect or preferably, mammalian cells, to provide for expression of a nucleic acid sequence described herein. Suitable bacterial and eukaryotic expression vectors are commercially available and well known in the art and their use is described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994).

Many mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of nucleic acids in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Many such vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g. EPV and EBV vectors.

Expression and cloning vectors usually contain one or more regulatory sequences (e.g., a promoter) operably linked to the encoding nucleic acid sequence to direct RNA synthesis. Promoters recognized by a variety of potential host cells are well known. Promoters suitable for use with prokaryotic hosts include the beta-lactamase and lactose promoter systems (Chang et al., Nature, 275:615 (1978); Goeddel et al., Nature, 281:544 (1979)), alkaline phosphatase, a tryptophan (trp) promoter system (Gocddcl, Nucleic Acids Rcs., 8:4057 (1980); EP 36,776), and hybrid promoters such as the tac promoter (deBoer et al., Proc. Natl. Acad. Sci. USA, 80:21-25 (1983)). Promoters for use in bacterial systems also will contain a Shine-Dalgarno (S.D.) sequence operably linked to the encoding DNA. Promoters for vectors in mammalian host cells can be obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. The promoter sequence may be a "tissue-specific promoter," which means a nucleic acid sequence that serves as a promoter, i.e., regulates expression of a selected nucleic acid sequence operably linked to the promoter, and which affects expression of the selected nucleic acid sequence in specific cells.

Transcription of a DNA by higher eukaryotes may be increased by inserting an enhancer sequence into the vector. Enhancers are cis-acting elements of DNA, usually about from 10 to 300 bp that act on a promoter to increase its transcription. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be present at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the RNA. Such sequences are commonly present at the 5' and, occasionally 3', untranslated regions of eukaryotic or viral DNAs or cDNAs. These regions contain nucleotide segments transcribed as polyadenylated fragments in the untranslated portion of the RNA.

Pharmaceutically Acceptable Formulations

The therapeutic agent (e.g., pro-regenerative OPN fragment), or combination of agents (pro-regenerative OPN fragment with BDNF and/or IGF1), described herein can be contained in pharmaceutically acceptable formulations, otherwise referred to herein as a pharmaceutical composition. Such a pharmaceutically acceptable formulation may include a pharmaceutically acceptable carrier(s) and/or excipient(s). As used herein, "pharmaceutically acceptable excipient" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and rescaled crythrocytes. In one embodiment, the pharmaceutical composition is formulated for localized administration directly to a neuronal lesion (e.g., at the site of origin of the injured neuron or at the site of axonal injury).

The active therapeutic compound can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 μm, preferably less than 20 μm, and more preferably between about 0.1 and 10 μm.

Administration of the Pharmaceutically Acceptable Formulations to a Subject

Administration is to a subject by a route that results in contacting an effective amount of one or more of the therapeutic agents described herein (e.g., a pro-regenerative OPN fragment) to the target neuron(s). In one embodiment, administration of the therapeutic agent to a subject (e.g., in a single or in different pharmaceutical compositions, with or without an additional factor described herein) results in the therapeutic agent directly contacting an injured neuron in need of regeneration (e.g., at the site of axonal injury or at the site of origin of the injured neuron). In one embodiment, administration results in contacting neurons proximal to a site of neuronal injury. In one embodiment, the administration is directly to an injured neuron (e.g., at the site of origin of the injured neuron or at the site of axonal injury). Such administration can be achieved by localized or systemic administration.

The term "administering" to a subject includes dispensing, delivering or applying an active compound in a pharmaceutical formulation to a subject by any suitable route for delivery of the active compound to the desired location in the subject, (e.g., the injury, the injured neuron, or the site of desired outgrowth of the neuron). This includes, without limitation, delivery by either the parenteral or oral route, intramuscular injection, subcutaneous/intradermal injection, intravenous injection, buccal administration, transdermal delivery and administration by the rectal, colonic, vaginal, intranasal or respiratory tract route, intraocular, ocular. Another form of administration suitable for treatment of spinal cord injury is injection into the spinal column or spinal canal.

Specific routes of administration and the dosage regimen will be determined by skilled clinicians based on factors such as the exact nature of the condition being treated, the severity of the condition, and the age and general physical condition of the patient.

Administration to the subject can be by any one or combination of a variety of methods (e.g., parenterally, enterally and/or topically). The appropriate method(s) will depend upon the circumstances of the individual (e.g. the location of the target neuron(s), the condition of the individual, the desired duration of the contact, whether local or systemic treatment is desired). The administration can be by any methods described herein that will result in contact of sufficient therapeutic agent(s) to the target neuron to promote survival and/or regeneration.

Since regeneration and axonal generation in the treatment of a neuronal injury includes compensatory promotion of neuronal outgrowth of uninjured neurons, benefit is expected from mere delivery of the agent to an injury site. As such, suitable target neurons are actual damaged neurons, and also neurons that are undamaged (e.g., in the immediate area of an injury site). The specific location and extent of an injury site can be determined by the skilled practioner. Examples of injury sites are the site of physical damage or disruption of neuronal activity. The immediate area of an injury site will vary with respect to the specific injury, the nature of the injury, and the nature of the injured neurons (e.g., axonal length, specific function, etc.) and can be determined by the skilled practitioner.

In one embodiment, the administration is localized so as to be highly targeted to a specific site. In one embodiment, the administration is systemic, and results in delivery of the appropriate concentration to the specific site.

When an agent is delivered to a patient, it can be administered by any suitable route, including, for example, orally (e.g., in capsules, suspensions or tablets) or by parenteral administration. Parenteral administration can include, for example, intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally.

Both local and systemic administration are contemplated by the invention. Desirable features of local administration include achieving effective local concentrations of the active compound as well as avoiding adverse side effects from systemic administration of the active compound. In one embodiment, the therapeutic agents are administered by introduction into the cerebrospinal fluid of the subject. In certain aspects of the invention, the therapeutic agent is introduced into a cerebral ventricle, the lumbar area, or the cisterna *magna*. In another aspect, the therapeutic agent is introduced locally, such as into the site of nerve or cord injury, into a site of pain or neural degeneration, or intraocularly to contact neuroretinal cells.

The pharmaceutically acceptable formulations can be suspended in aqueous vehicles and introduced through conventional hypodermic needles or using infusion pumps.

In one embodiment, the therapeutic agent formulation described herein is administered to the subject in the period from the time of, for example, an injury to the CNS up to about 100 hours after the injury has occurred, for example within 6, 12, or 24 hours from the time of injury.

In one embodiment, the therapeutic agent formulation is administered into a subject intrathecally. As used herein, the term "intrathecal administration" is intended to include delivering an active compound formulation directly into the cerebrospinal fluid of a subject, by techniques including lateral cerebroventricular injection through a burrhole or cisternal or lumbar puncture or the like (described in Lazorthes et al., 1991, and Ommaya A. K., 1984, the contents of which are incorporated herein by reference). The term "lumbar region" is intended to include the area between the third and fourth lumbar (lower back) vertebrae. The term "cisterna *magna*" is intended to include the area where the skull ends and the spinal cord begins at the back of the head. The term, "cerebral ventricle" is intended to include the cavities in the brain that are continuous with the central canal of the spinal cord. Administration of a therapeutic agent to any of the above mentioned sites can be achieved by direct injection of the active compound formulation or by the use of infusion pumps. Implantable or external pumps and catheter may be used.

For injection, the active agent (e.g., pro-regenerative OPN fragment) can be formulated in liquid solutions, preferably in physiologically compatible buffers such as Hank's solution or Ringer's solution or saline. In addition, the agent be formulated in solid form and re-dissolved or suspended immediately prior to use. Lyophilized forms are also included. The injection can be, for example, in the form of a bolus injection or continuous infusion (such as using infusion pumps) of the agent formulation.

In one embodiment of the invention, the formulation is administered by lateral cerebroventricular injection into the brain of a subject, preferably within 24 hours of when an injury (resulting in a condition characterized by aberrant axonal outgrowth of central nervous system neurons) occurs (such as within 6, 12, or 24 hours of the time of the injury). The injection can be made, for example, through a burr hole made in the subject's skull. In another embodiment, the formulation is administered through a surgically inserted shunt into the cerebral ventricle of a subject, preferably within 24 hours of when an injury occurs (such as within 6, 12 or 24 hours of the time of the injury). For example, the injection can be made into the lateral ventricles, which are larger, even though injection into the third and fourth smaller ventricles can also be made. The formulation can be administered by injection into the cisterna *magna*, or lumbar area of a subject, preferably within 24 hours of when an injury occurs (such as within 6, 12, or 24 hours of the time of the injury).

An additional means of administration to intracranial tissue involves application of compounds of the invention to the olfactory epithelium, with subsequent transmission to the olfactory bulb and transport to more proximal portions of the brain. Such administration can be by nebulized or aerosolized preparations.

In another embodiment, the formulation is administered to a subject at the site of injury, preferably within 24 hours of when an injury occurs (such as within 6, 12, or 24 hours of the time of the injury).

Formulations for ophthalmic administration are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic formulation may also be used as an adjunct to ophthalmic surgery, such as by vitreal or subconjunctival injection following ophthalmic surgery. The formulation may be used for acute treatment of temporary conditions, or may be administered chronically, especially in the case of degenerative disease. The ophthalmic formulation may also be used prophylactically, especially prior to ocular surgery or noninvasive ophthalmic procedures or other types of surgery.

The therapeutic agents described herein (e.g., pro-regenerative OPN fragment optionally with BDNF and/or IGF1) can contact with the neuron using an implantable device that contains the therapeutic agent and that is specifically adapted for delivery to a neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the agents sufficient to promote regeneration and/or survival of the neuron. In one embodiment, the device provides continuous contact of the neuron with the agent at nanomolar or micromolar concentrations, (e.g., for at least 2, 5, or 10 days, or for at least 2, 3, or 4 weeks, or for greater than 4 weeks, e.g., 5, 6, 7, or 8 weeks).

In one embodiment, the agent (e.g., pro-regenerative OPN fragment optionally with BDNF and/or IGF1) is contacted in vivo by introduction into the central nervous system of a subject, e.g., into the cerebrospinal fluid of the subject. In certain aspects of the invention, the agent is introduced intrathecally, e.g., into a cerebral ventricle, the lumbar area, or the cisterna *magna*. In another aspect, the agent is introduced intraocularly, to thereby contact retinal ganglion cells or the optic nerve. Modes of administration are described in U.S. Pat. No. 7,238,529.

In one embodiment of the invention, the therapeutic agent is administered by lateral cerebro ventricular injection into the brain of a subject in the inclusive period from the time of the injury to a time determined by the skilled practitioner (e.g., 24 hours). The injection can be made, for example, through a burr hole made in the subject's skull. In another embodiment, said encapsulated therapeutic agent is administered through a surgically inserted shunt into the cerebral ventricle of a subject in the inclusive period from the time of the injury to a time determined by the skilled practitioner (e.g., 24 hours thereafter). For example, the injection can be made into the lateral ventricles, which are larger, even though injection into the third and fourth smaller ventricles can also be made.

The therapeutic agent (e.g., pro-regenerative OPN fragment optionally with BDNF and/or IGF1) can be administered by injection into the cisterna *magna*, or lumbar area of a subject in the inclusive period from the time of the injury to a time determined by the skilled practitioner (e.g., 100 hours thereafter). Administration can be continuous, or can be by repeated doses.

In one embodiment, the repeated doses are formulated so that an effective amount of the therapeutic agent is continually present at the injury site.

In one embodiment, administration occurs following neuronal injury in the subject, not prior to or at the time of neuronal injury.

Duration and Levels of Administration

Depending on the intended route of delivery, the therapeutic formulations containing the pro-regenerative OPN fragment may be administered in one or more dosage form(s) (e.g. liquid, ointment, solution, suspension, emulsion, tablet, capsule, caplet, lozenge, powder, granules, cachets, douche, suppository, cream, mist, eye drops, gel, inhalant, patch, implant, injectable, infusion, etc.). The dosage forms may include a variety of other ingredients, including binders, solvents, bulking agents, plasticizers etc.

In one embodiment, the therapeutic composition is administered to a subject for an extended period of time to produce optimum neuronal outgrowth. Such administration can be periodic or sustained. Sustained contact with the active compound can be achieved by, for example, repeated administration of the active compound over a period of time, such as one week, several weeks, one month or longer. More preferably, the formulation containing the pro-regenerative OPN fragment used to administer the active compound provides sustained delivery, such as by "slow release" of the active compound to a subject. For example, the formulation may deliver the active compound for at least one, two, three, or four weeks after the formulation is administered to the subject. Preferably, a subject to be treated in accordance with the present invention is treated with the formulation for at least 30 days (either by repeated administration or by use of a sustained delivery system, or both).

As used herein, the term "sustained delivery" is intended to include continual delivery of the therapeutic agent (e.g., pro-regenerative OPN fragment optionally with BDNF and/or IGF1) in vivo over a period of time following administration, preferably at least several days, a week, several weeks, one month or longer. Sustained delivery of the therapeutic agent can be demonstrated by, for example, the continued therapeutic effect of the active compound over time (such as sustained delivery of the agents can be demonstrated by continued axonal growth in CNS neurons in a subject). Alternatively, sustained delivery of the therapeutic agent may be demonstrated by detecting the presence of the active agent in vivo over time.

Preferred approaches for sustained delivery include use of a polymeric capsule, a minipump to deliver the formulation, a biodegradable implant. Implantable infusion pump systems (such as Infusaid) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

It is to be noted that dosage values may vary with the severity of the condition to be alleviated. It is to be further understood that for any particular subject, specific dosage regimens should be adjusted over time according to the individual need and the professional judgment of the person administering or supervising the administration of the agent and that dosage ranges set forth herein are exemplary only and are not intended to limit the scope or practice of the claimed invention.

The amount of agent (e.g., pro-regenerative OPN fragment optionally with BDNF and/or IGF1) administered to the individual will depend on the characteristics of the individual, such as general health, age, sex, body weight and tolerance to drugs as well as the degree, severity and type of rejection. The skilled artisan will be able to determine appropriate dosages depending on these and other factors. The dosage can be determined by the skilled practitioner and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In some embodiments of any of the aspects, the dose range is from 5 µg/kg body weight to 30 µg/kg body weight. Alternatively, the dose range will be titrated to maintain serum levels between 5 µg/mL and 30 µg/mL.

Delivery Device

Another aspect of the invention relates to a device for promoting regeneration in a lesioned neuron. The device may be implantable into the subject. The device may have a reservoir loaded with a premeasured and contained amount of a therapeutic formulation containing the pro-regenerative OPN fragment described herein (e.g., with BDNF and/or IGF1). The device may be specifically adapted for delivery to a region of the body having one or more lesioned CNS neurons. In one embodiment, the device is specifically adapted for delivery to a neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the therapeutic agent sufficient to promote regeneration and/or survival of the neuron. In one embodiment, the device provides continuous contact of the neuron with the agent at nanomolar or micromolar concentrations, (e.g., for at least 2, 5, or 10 days, or for at least 2, 3, or 4 weeks, or for greater than 4 weeks, e.g., 5, 6, 7, 8, 9, 10, 11, or 12 weeks).

Detection of Effects

Survival of a neuron is indicated by the number of neurons surviving from a specific injury or condition, as compared to the number of neurons surviving as a result of the effects of the administered agent (e.g., pro-regenerative OPN fragment optionally with BDNF and/or IGF1), and also by the length of time the survival persists, as compared to the length of time survival persists as a result of the effects of the administered agent. Survival is considered to be significant if it persists for an extended period of time post-injury (e.g., greater than 2 weeks post-injury, greater than 3 weeks, and greater than 4 weeks post-injury). In one embodiment, greater than 10% of neurons (e.g., 15%, 20%, 25%, 30%, 35%, 0%, 45%, 50%, 55%, 60%, 65%, 70% and 75%), survive for an extended period of time post-injury. In one embodiment, greater than 20% of neurons survive for an extended period of time post-injury.

Regeneration is indicated by the number of neurons (injured and also uninjured) and by extended length of the axonal outgrowth of the neurons, as compared to the number of neurons and extended length of the axonal outgrowth of the neurons that results from the effects of the adminstered agent, and by the time frame post-injury that the outgrowth occurs, as compared to the time frame post-injury that outgrowth occurs resulting from the effects of the administered agent. Regeneration and axonal outgrowth occurs if greater than 10% or greater than 20% (e.g., 15%, 20%, 25%, 30%, 35%, 0%, 45%, 50%, 55%, 60%, 65%, 70% and 75%) of the neurons regenerate injured axons or generate new axons, that extend at least 0.5 mm distal to the lesion epicenter. In one embodiment, greater than 10% or greater than 20% (e.g., 15%, 20%, 25%, 30%, 35%, 0%, 45%, 50%, 55%, 60%, 65%, 70% and 75%) of neurons regenerate injured axons or generate axons over 1 mm distal to the lesion site. In one embodiment, greater than 10% (e.g., 15%, 20%, 25%, 30%, 35%, 0%, 45%, 50%, 55%, 60%, 65%, 70% and 75%) or greater than 20% of neurons regenerate or generate new axons that extend at least 2 mm distal from the lesion site.

Regeneration and neuronal outgrowth is also indicated by a significant amount of outgrowth having occurred on or after 2 weeks post-injury. For example significant outgrowth occurs for up to 3 weeks or 4, 5, 6, 7, 8, 9, 10, 11, or 12 weeks post-injury. Regeneration and neuronal outgrowth can also be indicated by restoration of function to the neuron. Function of a neuron can be detected by a variety of methods known in the art.

Neurons

The methods and compositions described herein are suited for the promotion of survival, neuronal regeneration and axonal outgrowth of CNS (central nervous system) neurons. In one embodiment the neuron is a terminally differentiated neuron. In one embodiment, the neuron is an adult neuron (e.g., in a subject that has reached maturity, such as in humans older than 18 years). In one embodiment, the neuron is non-embryonic. In one embodiment, the neuron is in an immature organism (e.g., embryo, infant, child).

All CNS neurons are suitable for such methods described herein. CNS neurons include, without limitation, a cerebellar granule neuron, spinal cord neuron, or an ocular neuron. In one embodiment, the neuron is the optic nerve. In one embodiment, the neuron is a sensory neuron (e.g., dorsal root ganglion (DRG) sensory neuron). In one embodiment, the CNS neuron is known or determined to be under specific regeneration inhibition. Such determination can be determined by the skilled practitioner.

Neuronal Lesions

As used in the art, the term lesion refers to damage (e.g., to a system or a cell). Damage to a system is evidenced by aberrant function, reduction of function, loss of function of the system, or loss of essential components (e.g., specialized cells such as neurons). Damage to a specific neuron is also evidenced by aberrant function, loss of function, reduced function, and/or cell death. Some forms of damage to a neuron can be directly detected (e.g., by visualization as with a severed or crushed neuronal axon). Neuronal lesions can result from a variety of insults, including, injury from physical trauma, toxic effects, atrophy (e.g., due to lack of trophic factors). Injuries that typically cause neuronal lesions include, without limitation, severing and crushing. A neuronal lesion, as the term is used herein, results from damage to the neuron. Such damage may be complete loss of a neuron, or loss of a part of the neuron (e.g., an axon). Such damage may results from acute or traumatic injury to the neuron (e.g., crush, severing) such as the result of external trauma to the subject (e.g., contusion, laceration, acute spinal cord injury, traumatic brain injury, cortical impact, etc.). Acute traumatic injury to a neuron can also result from an acute condition, such as stroke, that results in acute ischemia to the neuron resulting in acute damage. The specific location of neuronal damage will vary with the specific cause of the damage, and the specific individual. In one embodiment of the invention described herein, the lesioned CNS neuron is located in CNS white matter, particularly white matter that has been subjected to traumatic injury.

Damage to a neuron may also be incurred from a chronic injury (e.g., repetitive stress injury) or condition (e.g., chronic inflammation or disease). Chronic injury leads to neurodegeneration such as caused by neurotoxicity or a neurological disease or disorder (e.g. Huntington's disease, Parkinson's disease, Alzheimer's disease, multiple system atrophy (MSA), etc.). In one embodiment, the damage is not incurred from a chronic neurodegernative disease, such as Alzheimer's disease.

In one embodiment of the invention, damage results from an ocular injury or disorder (e.g. toxic amblyopia, optic atrophy, higher visual pathway lesions, disorders of ocular motility, third cranial nerve palsies, fourth cranial nerve palsies, sixth cranial nerve palsies, internuclear ophthalmoplegia, gaze palsies, eye damage from free radicals, etc.), or an optic neuropathy (e.g. ischemic optic neuropathies, toxic optic neuropathies, ocular ischemic syndrome, optic nerve inflammation, infection of the optic nerve, optic neuritis, optic neuropathy, papilledema, papillitis, retrobulbar neuritis, commotio retinae, glaucoma, macular degeneration, retinitis pigmentosa, retinal detachment, retinal tears or holes, diabetic retinopathy, iatrogenic retinopathy, optic nerve drusen, etc.).

Damage to a neuron can be detected by the skilled practitioner through a variety of assays known in the art. Loss of function assays can be used to determine neuronal damage. Physical damage to the neuron (e.g., axonal crushing or severing) can sometimes be observed diagnostically through routine methods. One way to detect a lesion is through detection of axotomy-induced stress and/or pathology-induced down-regulation of protein translation (e.g., detected directly, indirectly, or inferred).

Treatment of Neurological Disorders

Elements of the nervous system subject to disorders which may be effectively treated with the therapeutic compounds and methods of the invention include the central, somatic, autonomic, sympathetic and parasympathetic components of the nervous system, neurosensory tissues within the eye, ear, nose, mouth or other organs, as well as glial tissues associated with neuronal cells and structures. Neurological disorders may be caused by an injury to a neuron, such as a mechanical injury or an injury due to a toxic compound, by the abnormal growth or development of a neuron, or by the misregulation, such as downregulation, of an activity of a neuron. Neurological disorders can detrimentally affect nervous system functions such as the sensory function (the ability to sense changes within the body and the outside environment); the integrative function (the ability to interpret the changes); and the motor function (the ability to respond to the interpretation by initiating an action such as a muscular contraction or glandular secretion).

Examples of neurological disorders include traumatic (e.g., acute) or toxic injuries to cranial nerves, spinal cord or to the brain, cranial nerves, traumatic brain injury, stroke, cerebral aneurism, and spinal cord injury. Other neurological disorders include cognitive and neurodegenerative disorders such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, hereditary motor and sensory neuropathy (Charcot-Marie-Tooth disease), diabetic neuropathy, progressive supranuclear palsy, epilepsy, and Jakob-Creutzfieldt disease. Autonomic function disorders include hypertension and sleep disorders.

As used herein, the term "acute" is used in reference to the timing of an injury. An acute injury is one which has taken place within a few days and is not ongoing.

In Vitro Treatment of Neurons

Neurons derived from the central nervous system can be contacted with the agents ex vivo to modulate axonal outgrowth in vitro. Accordingly, neurons can be isolated from a subject and grown in vitro, using techniques well known in the art, and then treated in accordance with the present invention to modulate axonal outgrowth. Briefly, a neuronal culture can be obtained by allowing neurons to migrate out of fragments of neural tissue adhering to a suitable substrate (such as a culture dish) or by disaggregating the tissue, such as mechanically or enzymatically, to produce a suspension of neurons. For example, the enzymes trypsin, collagenase, elastase, hyaluronidase, DNase, pronase, dispase, or various combinations thereof can be used. Methods for isolating neuronal tissue and the disaggregation of tissue to obtain isolated cells are described in Freshney, Culture of Animal Cells, A Manual of Basic Technique, Third Ed., 1994, the contents of which are incorporated herein by reference.

Such cells can be subsequently contacted with the therapeutic agent denoted herein (alone or in combination with another agent) in amounts and for a duration of time as described above. Once modulation of axonal outgrowth has been achieved in the neurons, these cells can be re-administered to the subject, such as by implantation.

Unless otherwise defined herein, scientific and technical terms used in connection with the present application shall have the meanings that are commonly understood by the skilled practioner. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following numbered paragraphs:

1. A method of promoting neuronal outgrowth in a subject with a neuronal lesion in their central nervous system comprising administering to the subject an effective amount of a pro-regenerative OPN fragment and an effective amount of one or both of IGF1and BDNF, to thereby contact the lesion.
2. The method of paragraph 1 further comprising administering to the subject an effective amount of a voltage gated potassium channel blocker.
3. The method of paragraph 2, wherein the voltage gated potassium channel blocker is 4-AP or 4-AP-MeOH.
4. The method of any one of paragraphs 1-3, wherein the subject is an adult.
5. The method of any one of paragraphs 1-4, wherein the neuronal lesion results from spinal cord injury, traumatic brain injury or stroke.
6. The method of any one of paragraphs 1-5, wherein administering results in slow release of the pro-regenerative OPN fragment.
7. The method of any one of paragraphs 1-6, wherein administering begins within 24 hours of the time of lesion development.
8. The method of any one of paragraphs 1-7, wherein administering is periodic.
9. The method of any one of paragraphs 1-8, wherein administering is over a period of at least 8 weeks.

10. The method of any one of paragraphs 1-9, wherein administering is over a period of at least 12 weeks.
11. The method of any one of paragraphs 1-10, wherein administering is localized.
12. The method of any one of paragraphs 1-11, wherein administering is directly to the injury site.
13. The method of any one of paragraphs 1-10, wherein administering is systemic.
14. A method of treating a subject with a neuronal lesion in their central nervous system comprising administering to the subject an effective amount of a pro-regenerative OPN fragment and an effective amount of one or both of IGF1 and BDNF, to thereby contact the lesion.
15. The method of paragraph 14 further comprising administering to the subject an effective amount of a voltage gated potassium channel blocker.
16. The method of paragraph 15, wherein the voltage gated potassium channel blocker is 4-AP or 4-AP-MeOH.
17. The method of any one of paragraphs 14-16, wherein the subject is an adult.
18. The method of any one of paragraphs 14-17, wherein the neuronal lesion results from spinal cord injury, traumatic brain injury or stroke.
19. The method of any one of paragraphs 14-18, wherein administering results in slow release of the pro-regenerative OPN fragment.
20. The method of any one of paragraphs 14-19, wherein administering begins within 24 hours of the time of lesion development.
21. The method of any one of paragraphs 14-20, wherein administering is periodic.
22. The method of any one of paragraphs 14-21, wherein administering is over a period of at least 8 weeks.
23. The method of any one of paragraphs 14-22, wherein administering is over a period of at least 12 weeks.
24. The method of any one of paragraphs 14-23, wherein administering is localized.
25. The method of any one of paragraphs 14-23, wherein administering is directly to the injury site.
26. The method of any one of paragraphs 14-23, wherein administering is systemic
27. A pharmaceutical composition comprising a pro-regenerative OPN fragment and a pharmaceutically acceptable excipient.
28. The pharmaceutical composition of paragraph 27 further comprising one or both of IGF1 and BDNF.
29. The pharmaceutical composition of any one of paragraphs 27-28, further comprising a voltage gated potassium channel blocker.
30. The pharmaceutical composition of paragraph 29, wherein the voltage gated potassium channel blocker is 4-AP or 4-AP-MeOH.
31. The pharmaceutical composition of paragraph 29, wherein the pharmaceutical composition is formulated for slow release of the pro-regenerative OPN fragment.
32. A delivery device comprising a pharmaceutical composition comprising a pro-regenerative OPN fragment and a pharmaceutically acceptable excipient, for delivery of the pharmaceutical composition to a neuronal lesion of a subject.
33. The device of paragraph 32 wherein the pharmaceutical composition further comprises one or both of BDNF and IGF1.
34. The device of any one of paragraphs 32-33, wherein the pharmaceutical composition further comprises a voltage gated potassium channel blocker.
35. The device of paragraph 34, wherein the voltage gated potassium channel blocker is 4-AP or 4-AP-MeOH.
36. The device of any one of paragraphs 32-35, wherein the pharmaceutical composition is formulated for slow release of the pro-regenerative OPN fragment.

EXAMPLES

Example 1

The axons of the corticospinal tract (CST) originate from corticospinal neurons (CSNs) in layer 5 of the motor and somatosensory cortex and innervate all segments of the spinal cord. The CST transmits cortical commands to the spinal cord, allowing willful intention to be translated into observable action. Disruption of CSNs and/or CST axons results in motor functional deficits after traumatic injuries like spinal cord injury and stroke. A proposed therapeutic approach is to promote CST regrowth in a hope to rebuild functional connections. In general, recovery could be achieved either by regenerative growth of injured CST axons across the lesion site, or by compensatory sprouting of spared axons that innervate the denervated areas. However, for both types of regrowth, the limited growth ability of adult CSNs is a formidable impediment. Thus, alternate therapeutic approaches are needed for regrowth.

Because of the unique importance of CST axons in controlling spinal cord function, whether OPN can sensitize CSNs' responses to growth factors and promote CST regrowth and relevant functional recovery in clinically relevant injury models was assessed. Because multiple pathways are interrupted by such injuries, the behavioral defects that result from damage to the CST were determined. Then, the combinatorial treatment of OPN and IGF1 in two different CST-related injury models, spinal cord T10 lateral hemisection and unilateral cortical stroke was determined. This treatment promoted robust CST regrowth with significant yet partial restoration of CST-dependent tasks. Treatment of 4-aiminopyridine-3-methanol (4-AP-MeOH) in these mice further increased functional recovery. These findings reveal a translatable strategy of promoting CST-dependent functional restoration in adults.

Results

Characterization of CST-Dependent Hindlimb Behavioral Deficits after T10 Lateral Hemisection In the majority of patients of spinal cord injury or stroke, some CST axons are spared, leading to an "incomplete" injury (Raineteau & Schwab, 2001). Accordingly, an ideal model involves incomplete injury with characterized tract-specific behavioral defects. Thoracic lateral hemisection was used, because the resultant lesions and behavioral deficits are reproducible and quantifiable (FIG. 1A, Ballermann and Fouad, 2006; Courtine et al., 2008; Takeoka et al., 2014). Furthermore, it is known that different from other types of descending axons (Tetzlaff et al., 1994; Ballermann and Fouad, 2006; Courtine et al. 2008; Alilain et al., 2011; Ruschel et al., 2015), CST axons have limited ability of exhibiting midline crossing after injury in the adult mice (Fouad et al., 2001; Weidner et al., 2001; Bareyre et al., 2004; Liu et al., 2010). Thus, CST-related anatomical and behavioral features of adult mice following T10 spinal cord lateral hemisection were examined. Within weeks after injury, several descending axon tracts (Ballermann and Fouad, 2006; Courtine et al., 2008; Takeoka et al., 2014), including reticulospinal, propriospinal and serotonergic (FIGS. 1B and 1C), on the intact side sprouted across the midline and innervated the denervated side of the spinal cord. In contrast, CST axons had limited sprouting in the same mice (FIGS. 1B and 1C).

Next, a variety of behavioral tests were performed to define the functional deficits due to T10 lateral hemisection (FIGS. 2B-2J, 1D and 1E). Consistent with previous reports (Ballermann and Fouad, 2006; Courtine et al., 2008; Takeoka et al., 2014), the denervated hindlimbs showed severe locomotor deficits during the first week after injury (FIGS. 2B-2H). Over the following weeks, recovery varied dramatically among tasks. For example, inter-limb coordination recovered almost completely (FIGS. 2E-2H); weight support, protraction during walking, and speed tolerance on treadmill recovered partially (FIGS. 2B-2D and 2I), and paw dragging of the denervated hindlimb on a treadmill showed no significant recovery (FIG. 2J).

Figure 1D:
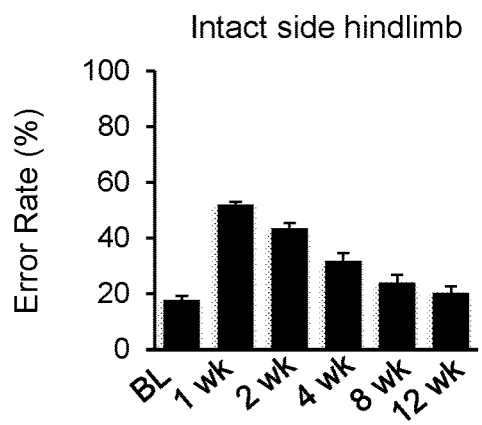
Figure 1E:
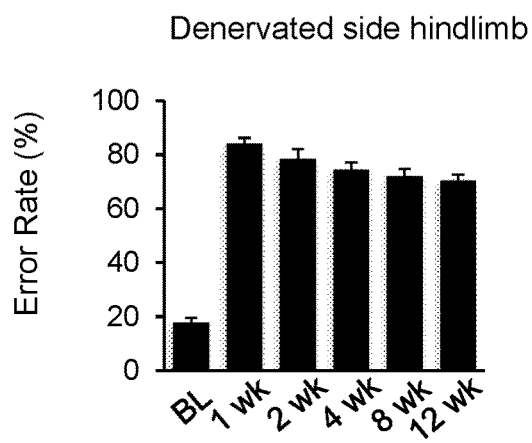
Figure 2A:
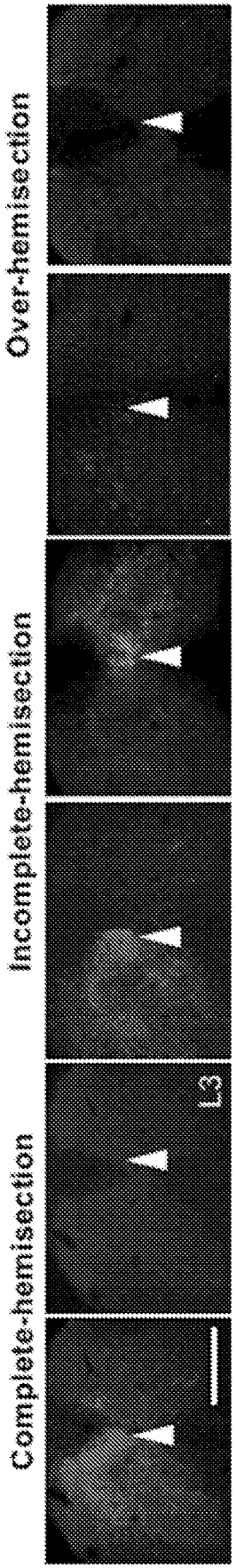
Figure 2D:
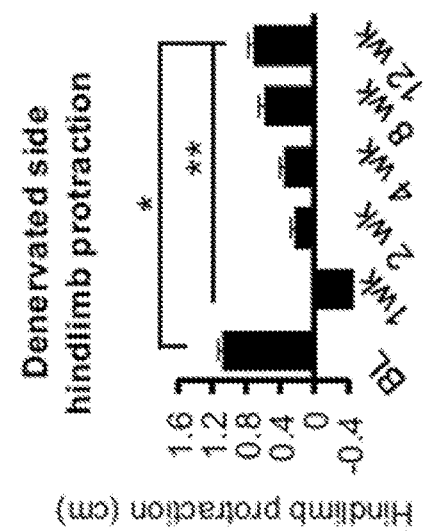
Figure 2C:
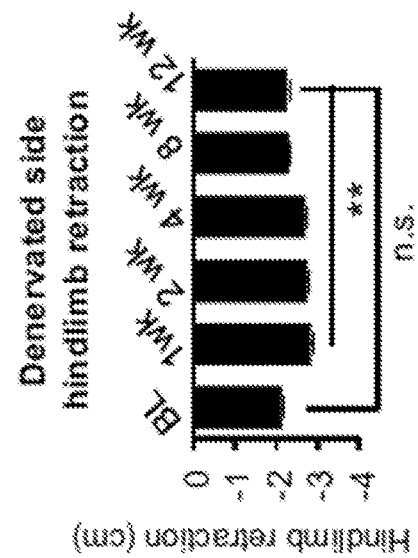
Figure 2B:
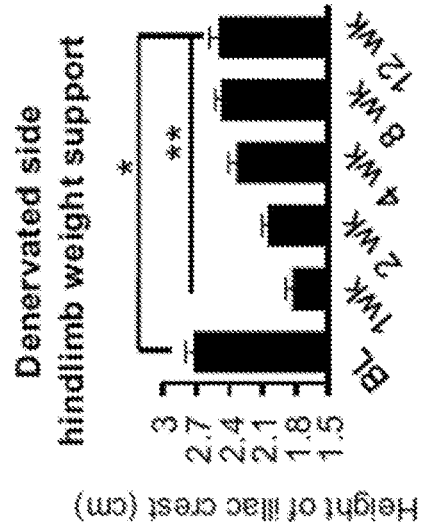
Figure 2K:
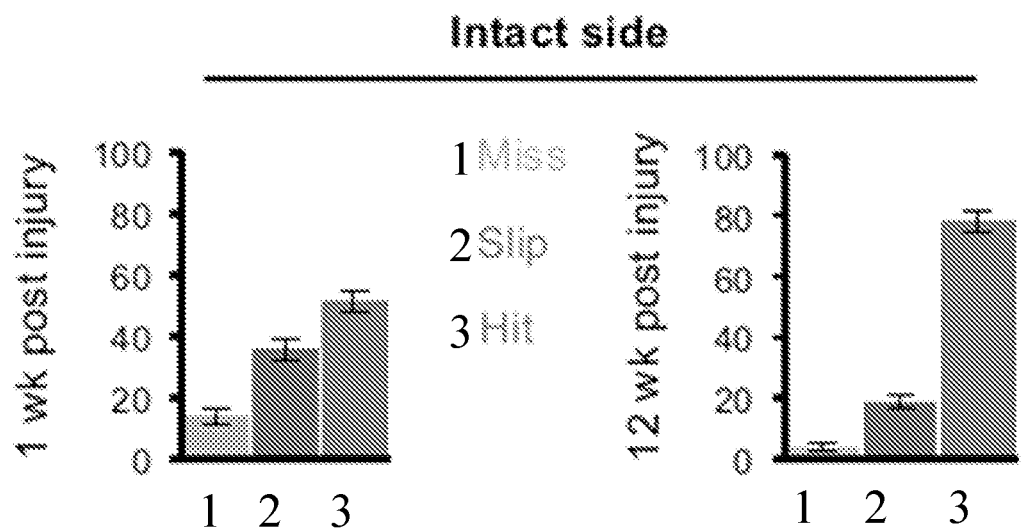
Figure 2L:
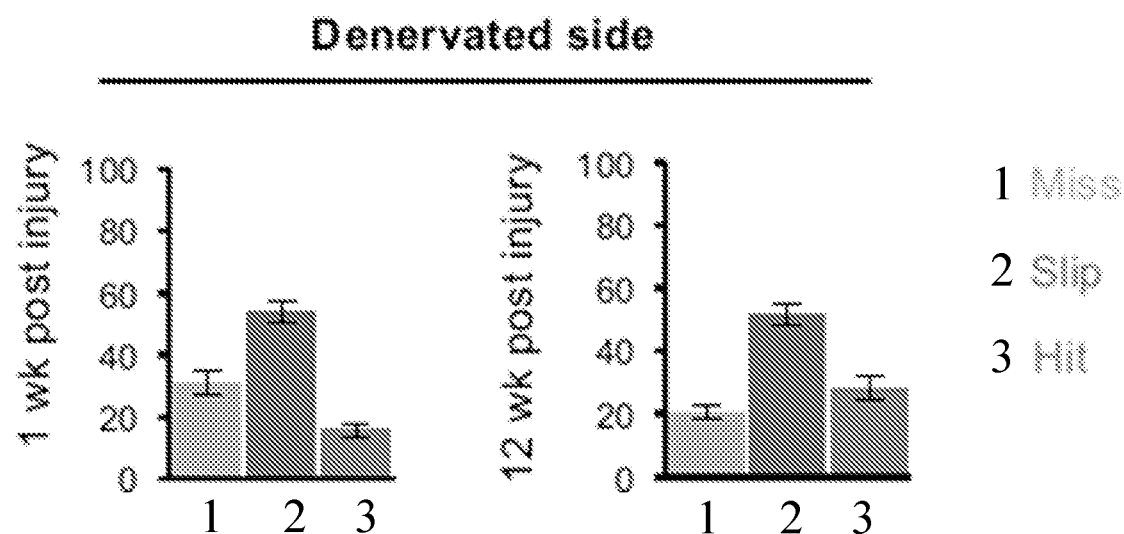

In addition, the ability of mice to walk on a horizontal ladder with irregularly spaced rungs was tested (Metz and Whishaw, 2002; Carmel et al., 2010, 2014; Jin et al., 2015). In this task, mice need to continuously adjust their stepping movements by aiming their limbs towards a new rung and then perform an accurate placement. The hindlimbs on the intact side showed a transient defect but then achieved almost full recovery (FIGS. 1D and 2K). In contrast, the injured hindlimb often missed the rung (miss error) or contacted the rung with a few digits followed by a slip (slip error), thereby resulting in a significantly higher error rate even at 12 weeks post injury (FIGS. 1E and 2L). Thus, despite spontaneous axonal reorganization and functional recovery, the mice with T10 lateral hemisection failed to show significant CST sprouting and still exhibited significant defects in several locomotor parameters, including paw dragging, speed tolerance on treadmill and precision placement on irregular ladder.

Figure 3A:
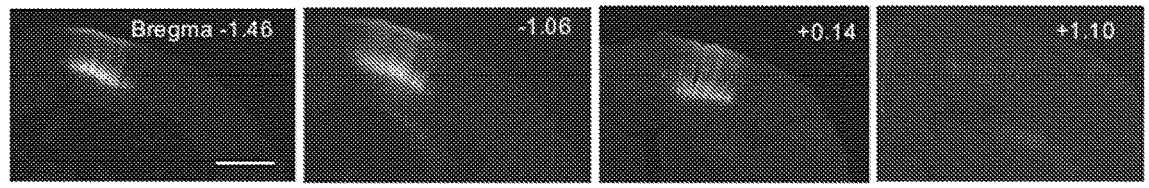
FIGS. 3A-3G present experimental results that indicate specific labeling and ablation of hindlimb CSNs. (A) Representative images showing HiRet-GFP labeled CSNs that were predominantly located in the hindlimb sensorimotor cortex. Scale bar: 1 mm. (B) Representative images showing HiRet-mCherry (left—visualized as red, shown here in black and white), green retrobeads (middle—visualized as green, shown here in black and white) and their merge (right). Bar graph: Percentage of mCherry+/Green beads+ neurons in hindlimb CSNs. The percentage in 8 sections was averaged and 3 mice in total was quantified. Scale bar: 200 μm. (C) Experimental paradigm: HiRet-FLEX-DTR or GFP (control) was injected into lower thoracic and lumbar (T13-L4) spinal cord at neonatal age P12-P14. Adult animals (P60) received DT injection, intraspinal AAV9-mCherry injection at lumbar spinal cord (L2-A) and were then perfused for histology. (D) Representative images showing retrogradely labeled mCherry+ CSNs, co-stained with anti-CD68, an activated microglia marker. Scale bar: 200 μm. (E) Quantification of retrogradely labeled hindlimb CSNs (normalized to those in control as 100). **, p<0.01. Student's t test. n=15 sections for HiRet-GFP (n=3) or HiRet-FLEX-DTR (n=3) injected mice, respectively. (F) Quantification of CD68 immunofluorescence intensities (normalized to those in control as 100) in hindlimb representing cortex (see FIG. 10). n.s.: no statistical significance. Student's t test. n=15 sections for HiRet-GFP (n=3) or HiRet-FLEX-DTR (n=3) injected mice, respectively. (G) Representative zoomed in images (63X) of the dorsal *funiculus* at the lumbar spinal cord (L3) stained with PKCγ. Scale bar 50 μm. The immunofluorescence above the threshold was quantified for both control and HiRet-FLEX-DTR injected animals. **: p<0.01, Student's t test, n=15 sections for HiRet-GFP (n=3) or HiRet-FLEX-DTR (n=3) injected mice, respectively.
Figure 3B:
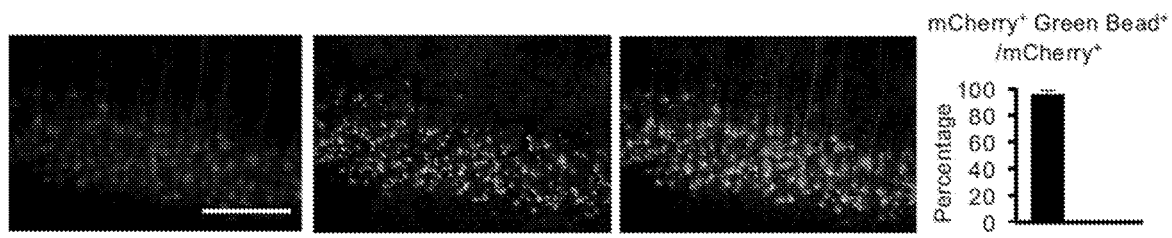
Figure 3C:
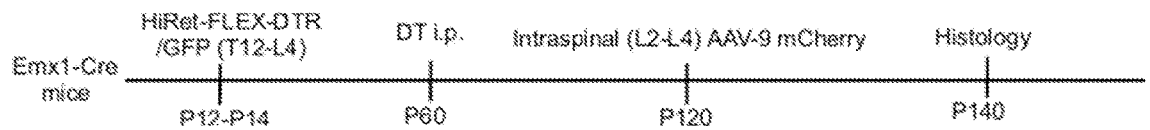
Figure 3D:
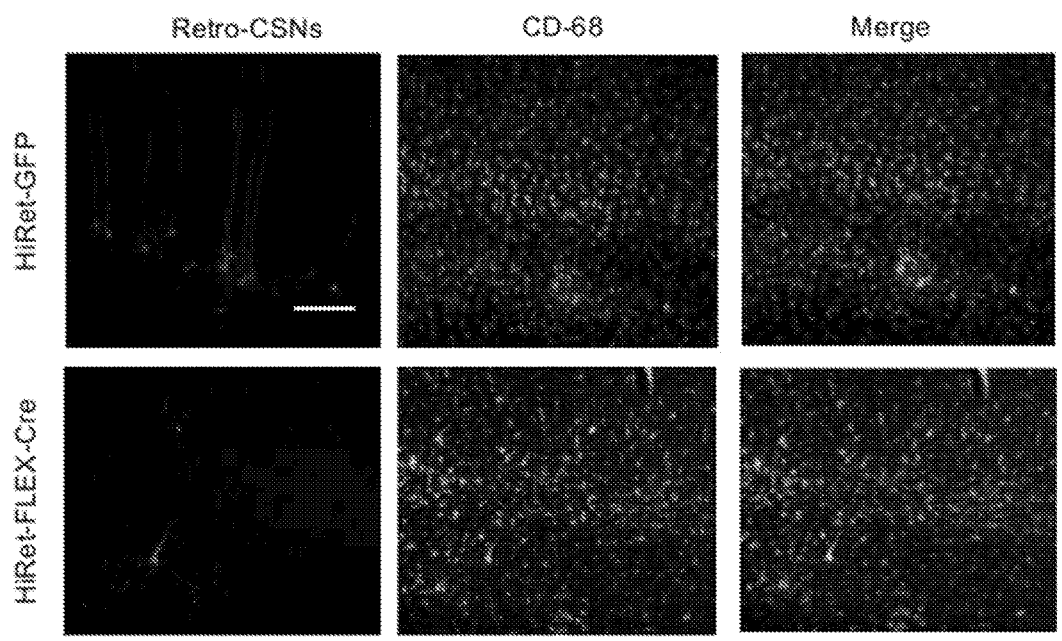
Figure 3E:
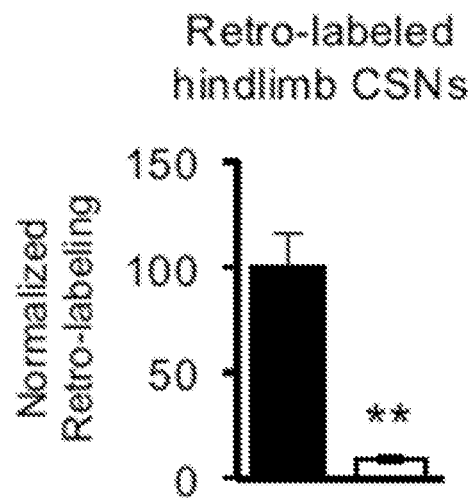
Figure 3F:
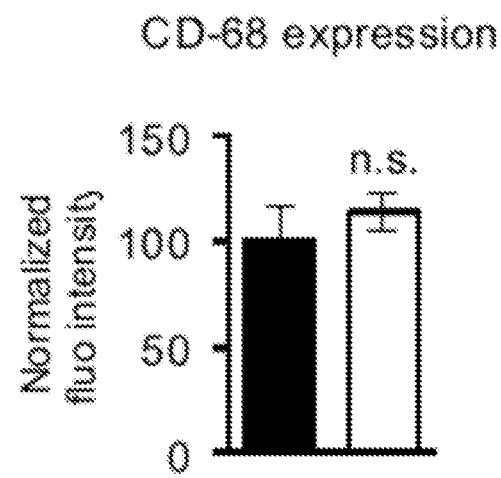
Figure 3G:
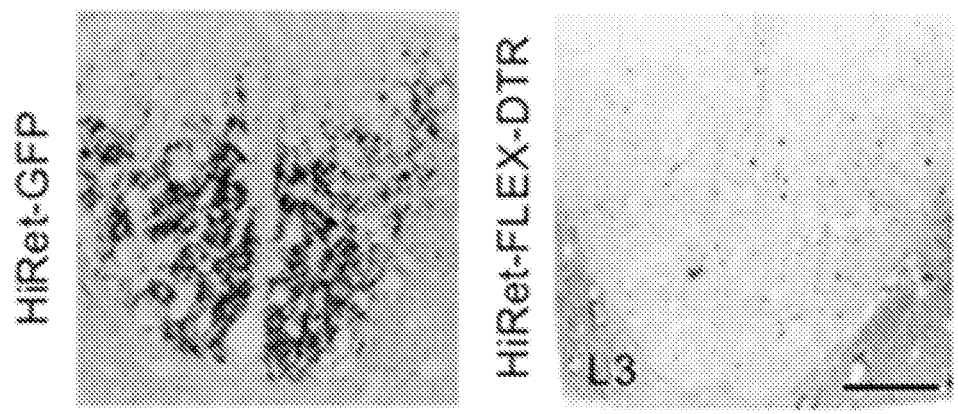
Figure 3G:
Figures 4A, 4B, 4C:
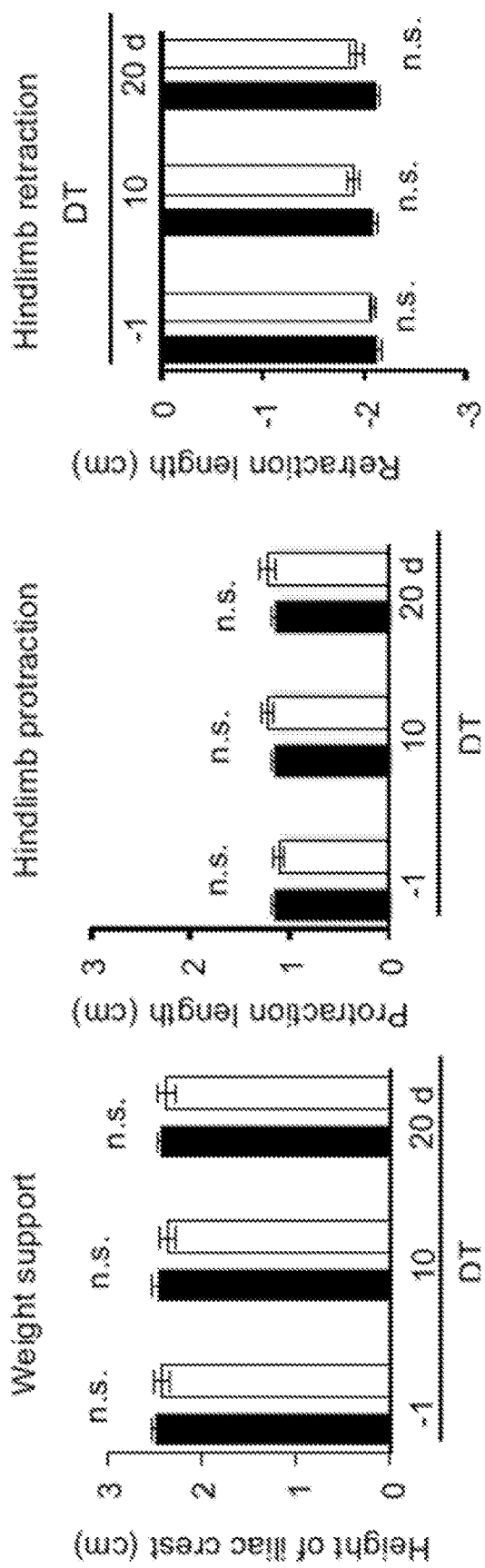
Figure 4G:
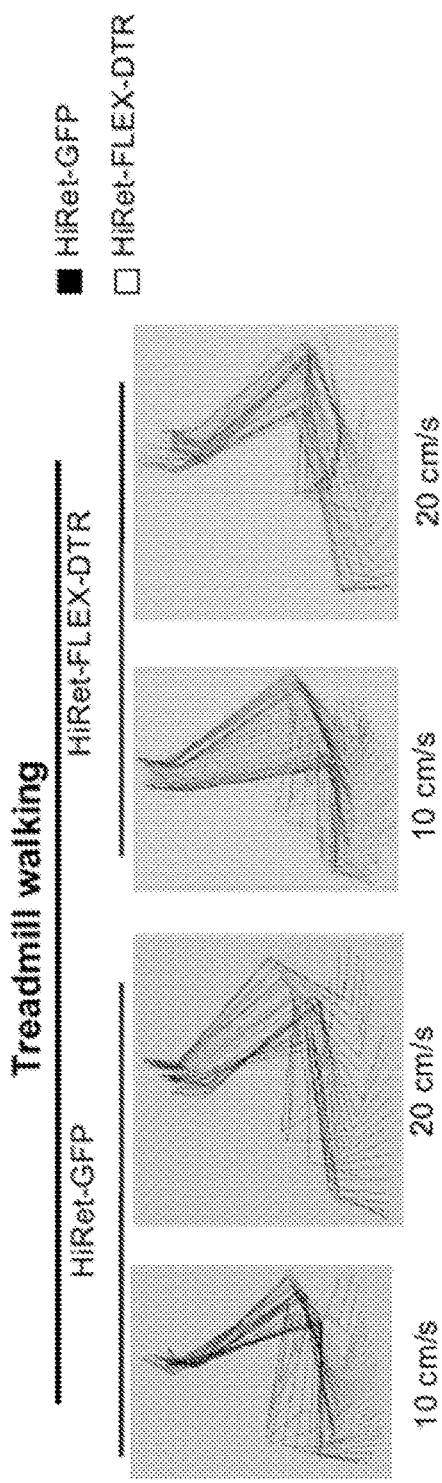
Figure 10A:
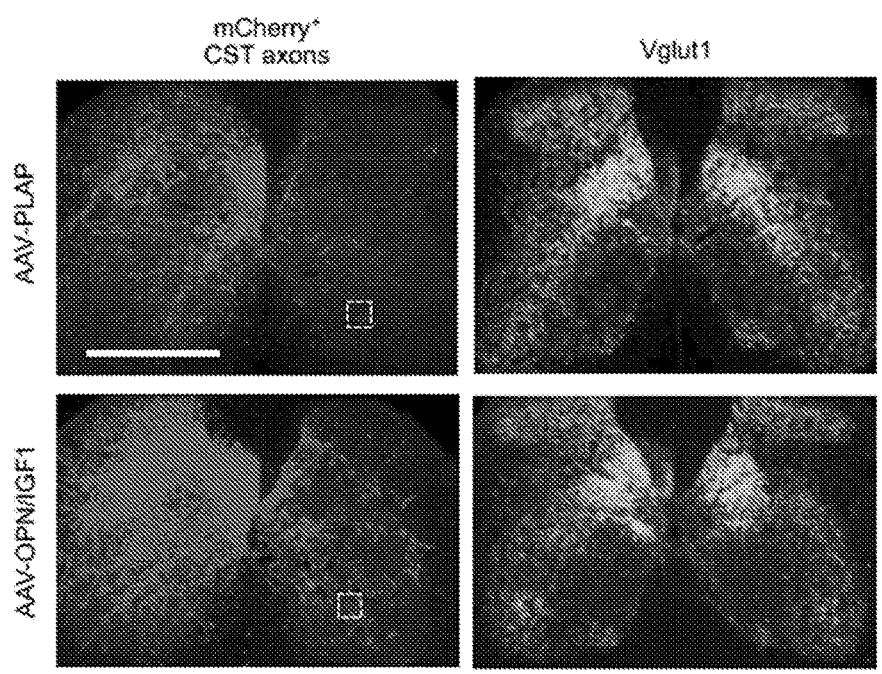
FIGS. 10A and 10B present experimental results that indicate collaterally sprouted axons form synapse-strictures in the lumbar spinal cord segments. (A) Representative images of lumbar spinal cord (L3) immunostained by anti-Vglut1 (visualized as green), anti-RFP (visualized as red) in AAV-PLAP and AAV-OPN/IGF1 treated animals with T10 lateral hemisection. The (B) Zoomed in images from (A) to show co-localization. Transparent arrowheads indicated Vglut1 and RFP co-localized synaptic boutons. Scale bars: 500 (A) and 50 (B) µm, respectively.
Figure 10B:
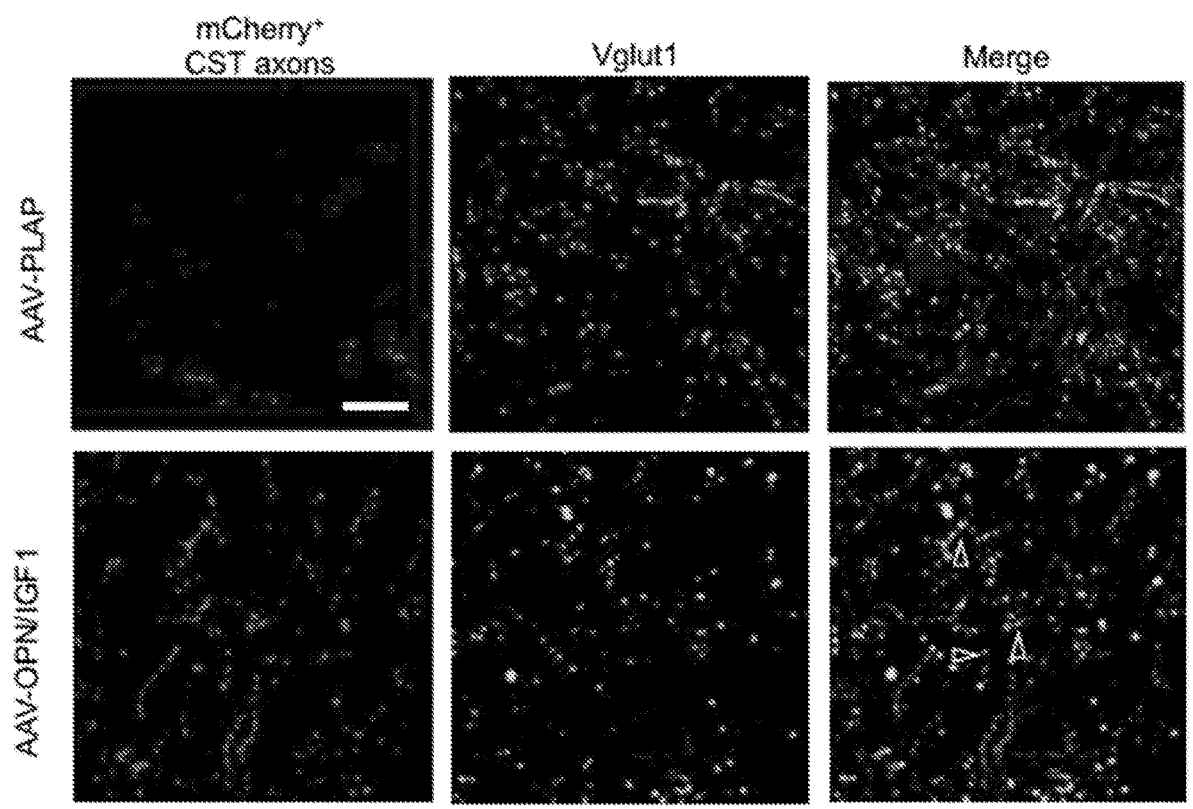

To investigate whether any of these persistent defects following T10 lateral hemisection resulted from loss of the CST, the CSNs which give rise to the CST axons that innervate the hindlimb were selectively ablated, without damaging other descending tracts. To do this, the efficient retrograde properties of a pseudotyped lentiviral vector (HiRet) were used (Kinoshita et al., 2012). GFP-expressing vector (HiRet-GFP) was injected into the spinal cord segments (T12-L4) of mice at the age of postnatal day 12-14 (P12-14) when most CST axons have reached their spinal targets (Bareyre et al., 2005) and the pruning of cortical projections is almost complete (O'Leary, 1992; O'Leary and Koester, 1993). As shown in FIG. 10A, CSNs in the hindlimb area of the primary sensorimotor cortex were efficiently targeted. To examine the retrograde labeling efficiency, HiRet-mCherry was co-injected with another commonly used retrograde tracer fluorescent microspheres (Kamiyama et al., 2015) from this, about 98% of green retrobeads labeled CSNs were co-labeled by mCherry, indicating a high efficiency of HiRet vectors in labeling CSNs (FIG. 10B). Next, HiRet vectors carrying flip-excision (FLEX) human diphtheria toxin receptor (DTR; HiRet-FLEX-DTR) were injected into the T12-L4 spinal cord of cortex-specific Emx1-Cre transgenic mice (Bareyre et al., 2005) (FIG. 1F). Upon diphtheria toxin (DT) administration, CST axons were efficiently ablated in the lumbar, but not cervical spinal cord, as indicated by immunostaining for the CST marker PKCγ (Liu et al., 2010) (FIGS. 1G and 3G). Consistent with this, the retrograde tracing at the lumbar spinal cord revealed less than 10% remaining CST axons in HiRet-FLEX-DTR injected mice (FIGS. 3C-3E). The DT-mediated CSNs ablation did not induce significant inflammatory response (FIGS. 3D and 3F). In these mice, basic locomotor functions, like weight support, excursion length, and limb coordination during ground walking were unperturbed (FIGS. 4A-4D), consistent with the previous findings that basic locomotor function achieves almost complete recovery after CST lesions (Metz et al., 1998; Muir & Whishaw, 1999). In addition, these mice were capable of adjusting gait patterns without overt paw dragging towards changing velocities when stepping on the treadmill (FIGS. 4E-4G).

Figure 1H:
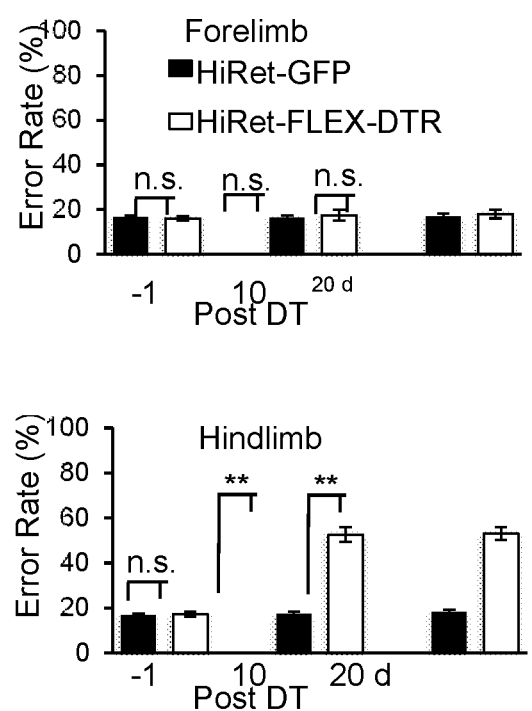
Figure 4H:
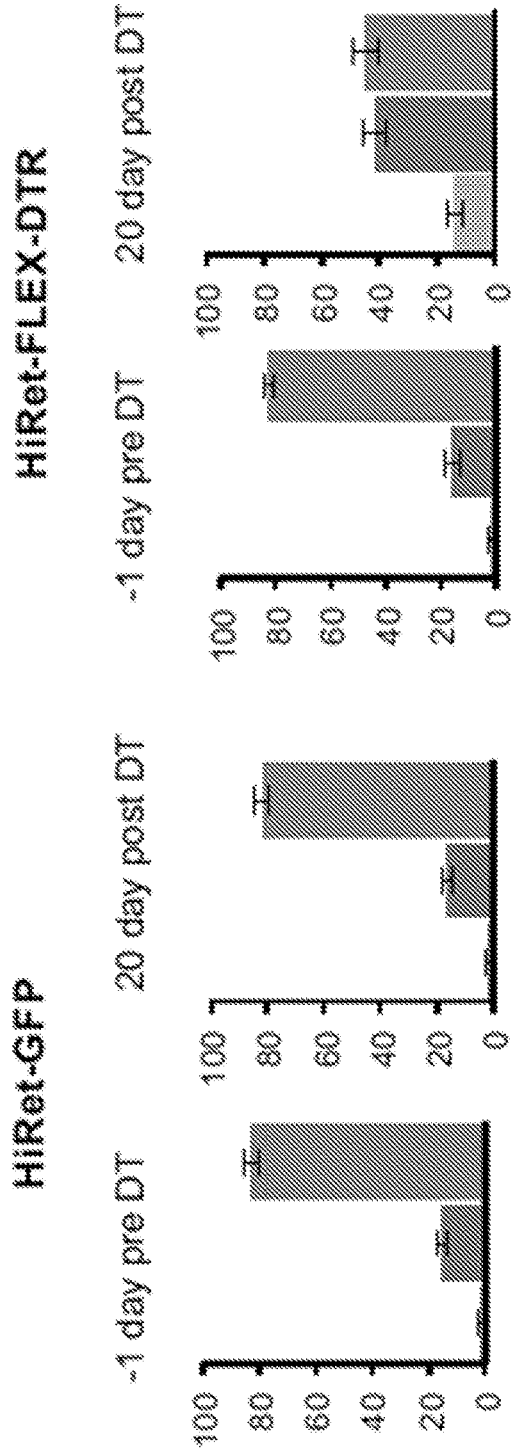

Similar to the mice with lateral hemisection (FIGS. 1D and 1E), the performance of the hindlimbs, but not the forelimbs, of these mice was permanently defective in the irregular walking assay (FIGS. 1H and 4H). Based on these results, the defects in the irregular walking task, but not the paw dragging and speed tolerance on the treadmill, after T10 hemisection is thought due to the lack of regrowth of spared CST axons and thus persistent CST denervation on the injured side of the lumbar spinal cord.

OPN Sensitizes Adult CSNs to IGF1

Figure 5A:
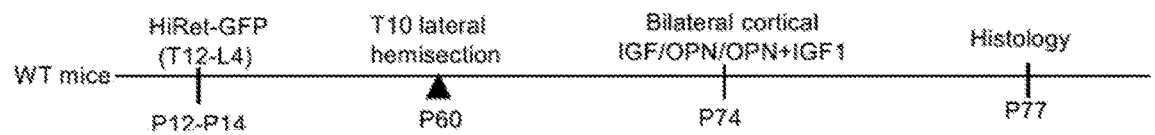
FIGS. 5A-5E present experimental results that indicate OPN sensitizes the responsiveness to IGF1 in adult CSNs. (A) Schematic diagram of the experimental timeline Wild type mice received intraspinal injection (at the spinal cord T12-L4 segments) with HiRet-GFP at P12-P14. T10 spinal cord lateral hemisection at P60, bilateral cortical injection of saline, soluble human recombinant IGF1, OPN or OPN/IGF1 at P74, and were sacrificed at P77 for histological analysis. (B) Representative images showing intact and axotomized CSNs (visualized as green: retrogradely labeled by GFP) co-stained with IGFR, piGFR, and pS6 in saline (top lanes), IGF1 (middle lanes), and OPN & IGF1 protein (bottom lanes) injected animals Arrowheads indicate the co-localization of GFP with IGFR, pIGFR, and pS6 immunofluorescence. Scale bar: 20 µm. (C,D,E) Quantification of immunofluorescence intensities of IGFR, pIGFRβ and pS6 in various conditions. All images were taken using identical optical parameters and scan settings. In each case, the intensities were normalized to that in intact CSNs with saline injection. ** and n.s., p<0.01 and no statistical significance. One way-ANOVA, followed by post hoc Bonferroni correction. For IGFR quantification, n=122, 107, 123, 126, 94, 93, 121, 113 for the intact and axotomized CSNs in saline (n=3). IGF1 (n=3). OPN (n=3) and OPN/IGF1 (n=3) injected animals, respectively. For pIGFRβ quantification, n=104, 119, 107, 122, 104, 96, 126, 118 for the intact and axotomized CSNs in saline (n=3), IGF1 (n=3), OPN (n=3) and OPN/IGF1 (n=3) injected animals, respectively. For pS6 quantification, n=130, 131, 130, 134, 119, 108, 133, 139 for the intact and axotomized CSNs in saline (n=3). IGF1 (n=3). OPN (n=3) and OPN/IGF1 (n=3) injected animals, respectively. Note that the images of OPN protein injected group were present in FIG. 12A.

Previous studies showed that IGF1 promotes axon growth by activating both PI3K and Erk/MAPK pathways in cultured CSNs isolated from neonatal mice (Ozdinler and Macklis, 2006). However, it is unknown whether IGF1 triggers similar signaling activation in adult CSNs and, if so, whether it could be altered by OPN treatment. Thus CSNs were labeled by spinal injection of HiRet-GFP, performed T10 lateral hemisection, and then bilaterally injected recombinant IGF, OPN or OPN/IGF1 proteins were bilaterally injected into the cortex (FIG. 5A). In 3 days, the cortical sections from both injured and intact sides of adult mice were immunostained for three factors. Anti-IGFR, anti-phospho-IGFRβ, an indicator for the activation of the IGF-1 mediated signaling pathways (Hernandez-Sanchez et al., 1995; Siddle, 2012), and anti-phospho-S6 (p-S6), an established marker of mTOR activation, one of the downstream target of IGF1 mediated signaling pathways (Liu et al., 2010; Pollak, 2008).

Figure 5B:
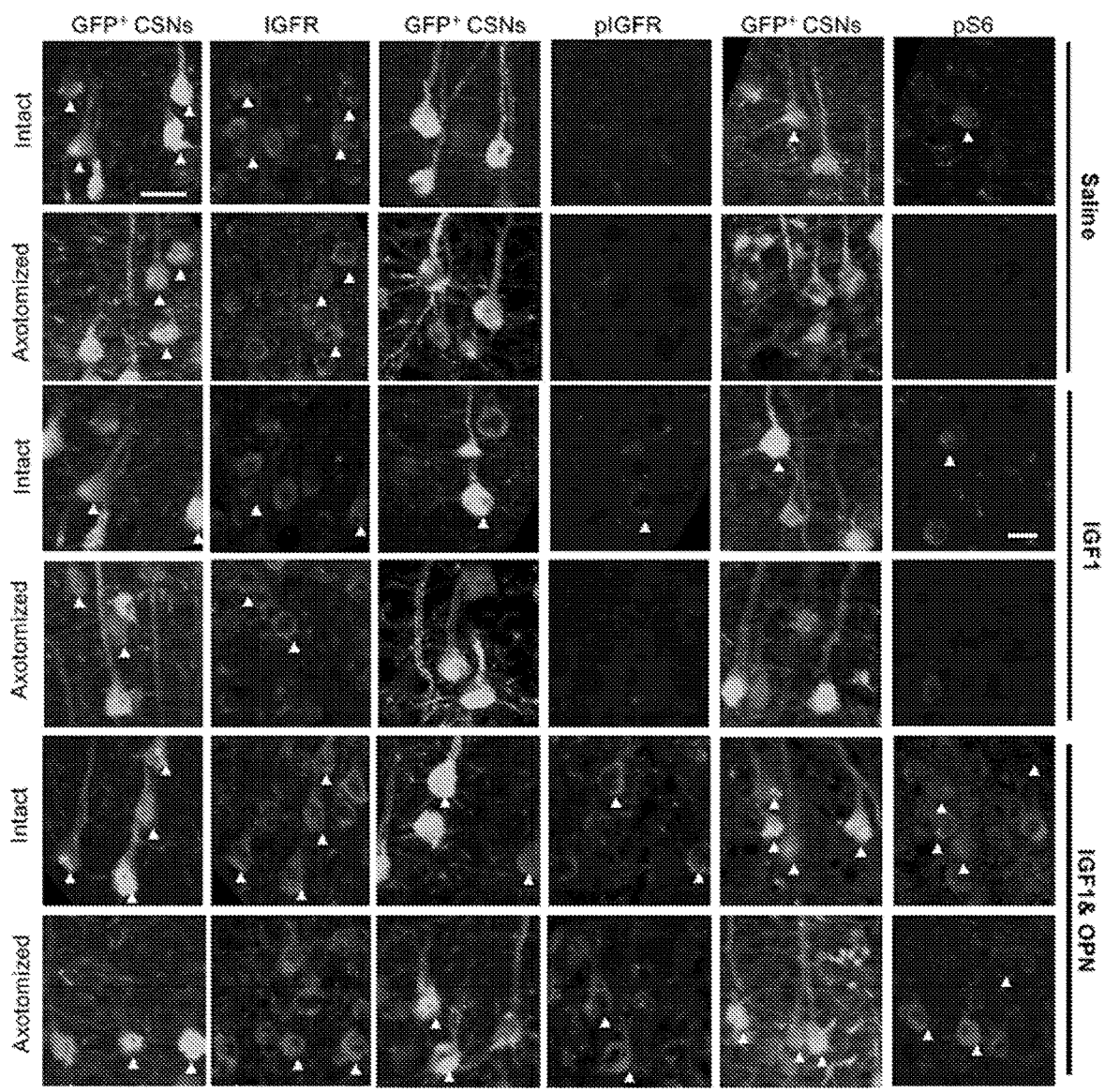
Figures 5C, 5D, 5E:
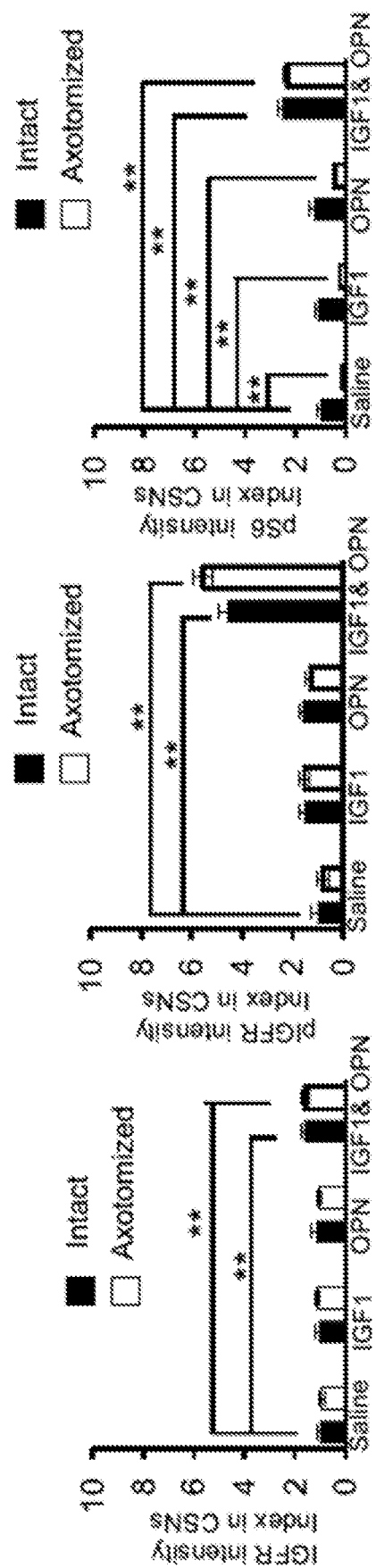
Figure 6A:
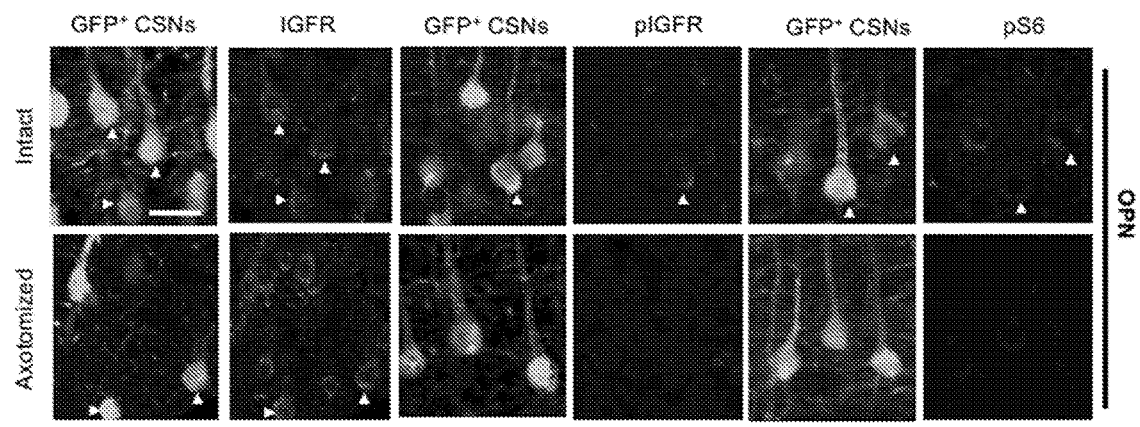
FIGS. 6A-6D present experimental results that indicate AAV-OPN/IGF1 treatment activated IGF1 mediated signaling pathways in adult CSNs. (A) Representative images showing intact and axotomized CSNs (visualized as green: retrogradely labeled by GFP) co-stained with IGFR, pIGFR, and pS6 in recombinant OPN protein injected animals (related to FIG. 2). Scale bar: 20 µm. (B) Schematic diagram of the experimental timeline. Wild type mice received T10 spinal cord lateral hemisection at P60, bilateral cortical injection of AAV-PLAP or AAV-OPN/IGF1 at P61, intraspinal AAV9-GFP injection at P180 and were sacrificed at P200 for histological analysis. (C) Representative images showing CSNs (visualized as green: retrogradely labeled by GFP) co-stained with IGFR, pIGFR, and pS6 in AAV-PLAP (upper lane) and AAV-OPN/IGF1 (bottom lane) injected animals Arrowheads indicate the co-localization of GFP with IGFR, pIGFR or pS6 immunofluorescence. Scale bar: 20 µm. (D) Quantification of immunofluorescence intensities of IGFR, pIGFRβ and pS6 in various conditions. All images were taken using identical optical parameters and scan settings. In each case, the intensities were normalized to that in intact CSNs with AAV-PLAP injection. * and **, p<0.05 and p<0.01, Student's t test. For IGFR, pIGFR and pS6 quantification, n=61, 93, 84, 102, 77, 96 for the intact CSNs in AAV-PLAP (n=3) and AAV-OPN/IGF1 (n=5) injected animals, respectively.

Levels of IGFR were comparable in intact or axotomized CSNs (FIGS. 5B, 6A, and 5C). The combination of IGF1 and OPN, but neither IGF1 or OPN alone, slightly increased (around 1.6 fold) the IGFR levels in both intact and axotomized CSNs (FIGS. 5B, 6A, and 5C). In contrast, levels of p-IGFRβ were barely detectable in intact or axotomized CSNs (FIGS. 5B, 6A, and 5D). While treatment with IGF1 or OPN alone had no overt effect on the p-IGFRβ in either intact or axotomized, mature CSNs, the combination of IGF1 and OPN significantly increased (around 6 fold) the phosphorylation level of IGFRβ (FIGS. 2B, 12A, and 2D), indicating an activation of the IGFR mediated signaling pathways. Furthermore, treatment with OPN and IGF1, but not IGF1 or OPN alone, significantly increased p-S6 levels in both intact and axotomized CSNs (FIGS. 5B, 6A, and 5E). Together, these results indicate that in both intact and injured CSNs, OPN is able to enhance the response to IGF1.

Figure 6B:
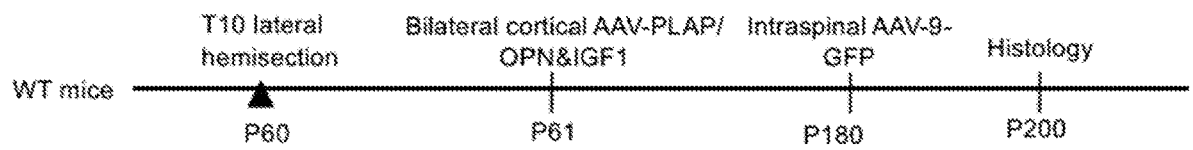
Figure 6C:
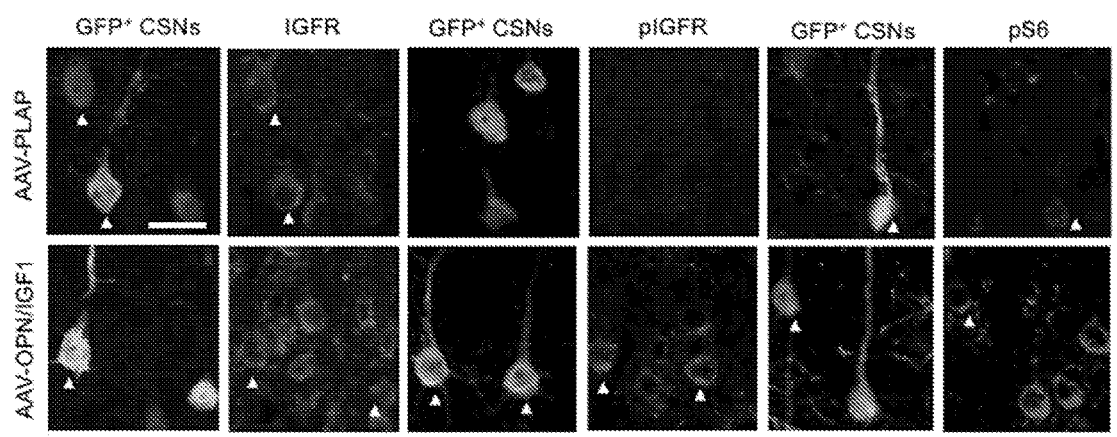
Figure 6D:
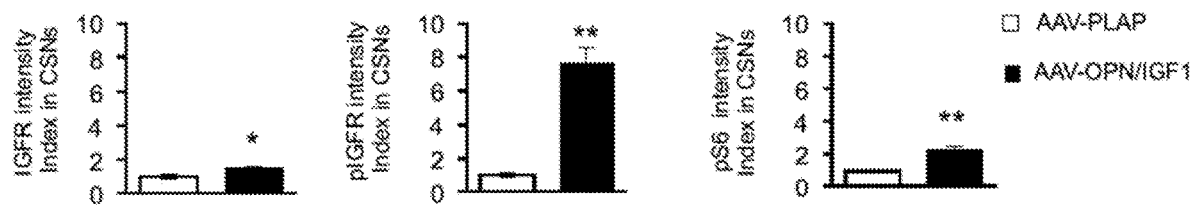
Figure 7A:
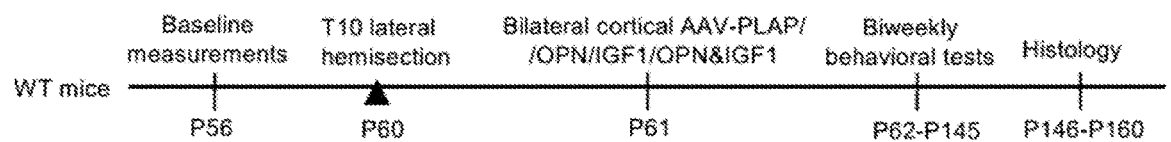
FIGS. 7A-7E present experimental results that indicate OPN/IGF1 treatment improves precision performance after spinal cord T10 lateral hemisection. (A) Schematic diagram of the experimental timeline. Wild type mice received baseline behavioral measurement at P56, T10 spinal cord lateral hemisection at P60, bilateral cortical injection of AAV-PLAP, AAV-OPN, AAV-IGF1 or AAV-OPN/IGF1 at P61, and biweekly behavioral measurement from P62-P145 before terminal histological analysis (B-E) Performance on irregular ladder walking of the hindlimb from the intact (B, C) and denervated (D. E) sides in AAV-PLAP, AAV-OPN, AAV-IGF1, and AAV-OPN/IGF1 treated animals. C and E: Hindpaw placement categories (breakdown of miss, slip, and hit) on irregular ladder walking. **: p<0.01 and p<0.05, respectively. Repeated measures ANOVA followed by post hoc Bonferroni correction. n=13, 9, 8, and 12 for AAV-PLAP, AAV-OPN, AAV-IGF1, and AAV-OPN/IGF1 treated groups respectively. Hit, miss, and slip in (C) and (E) represent three categories of hindpaw placement on the rungs during walking across the ladder.
Figure 7B:
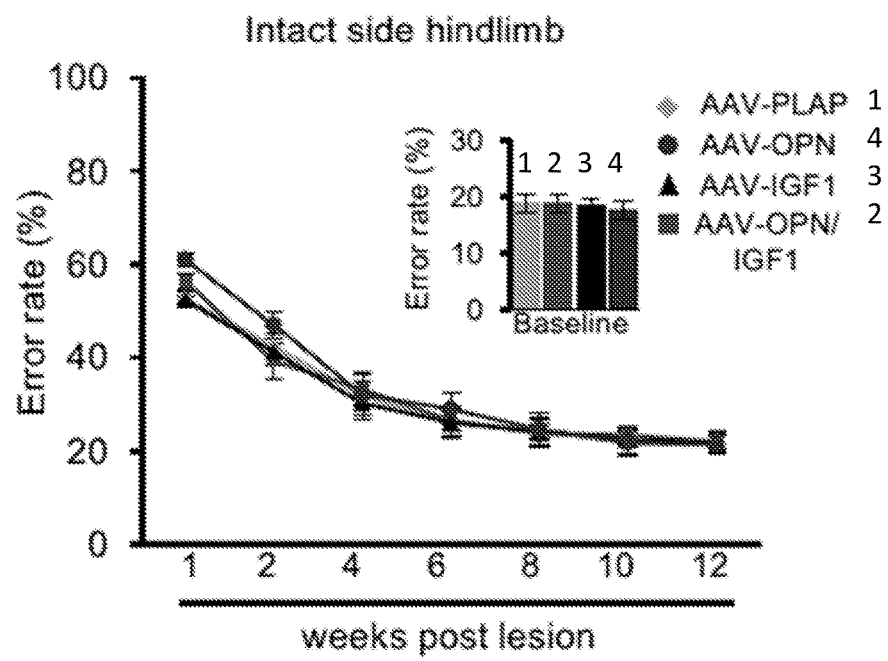
Figure 7C:
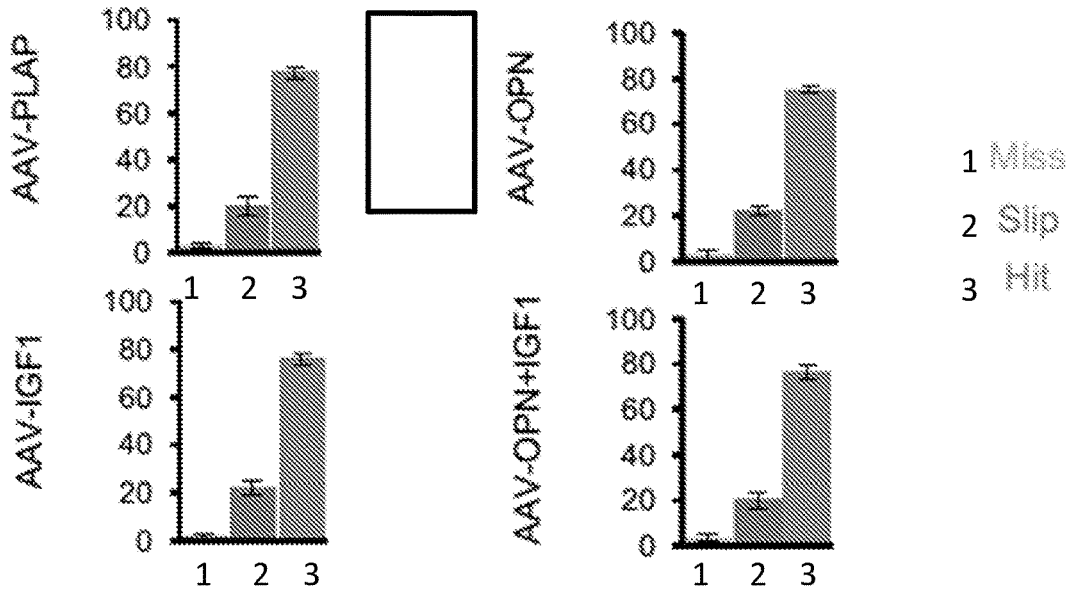
Figure 7D:
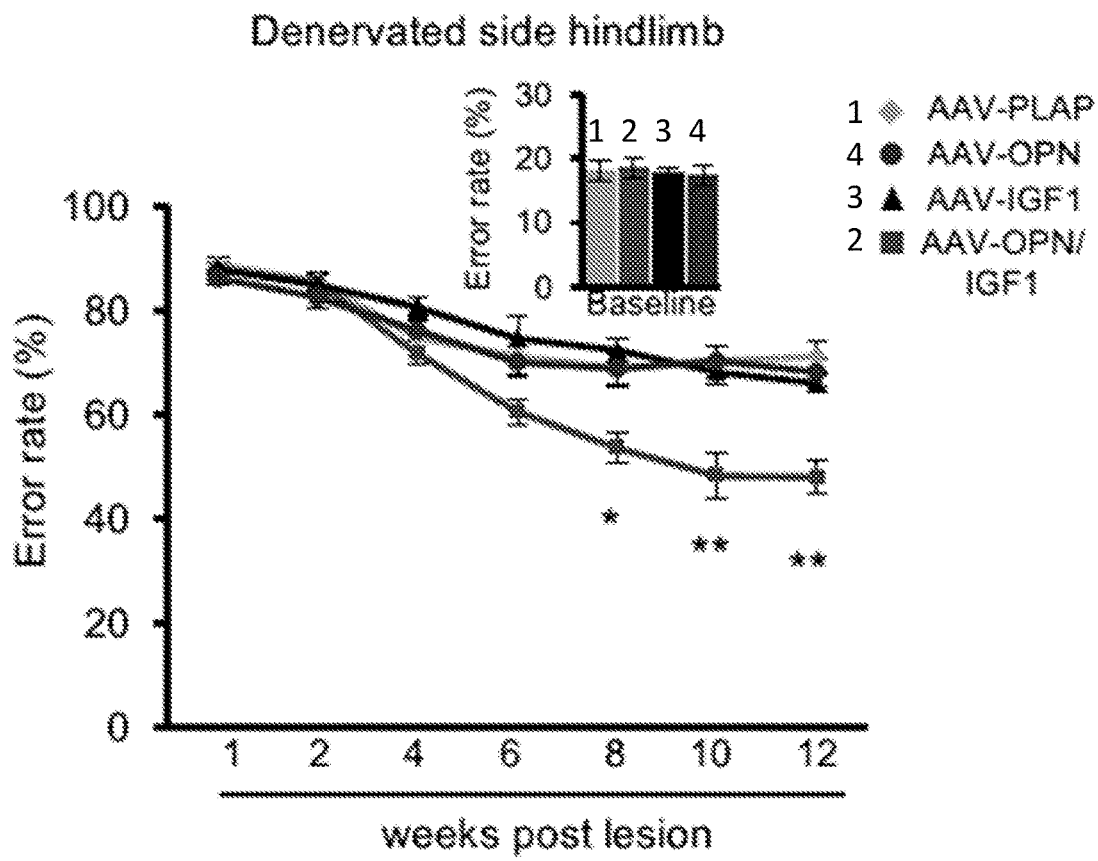
Figure 7E:
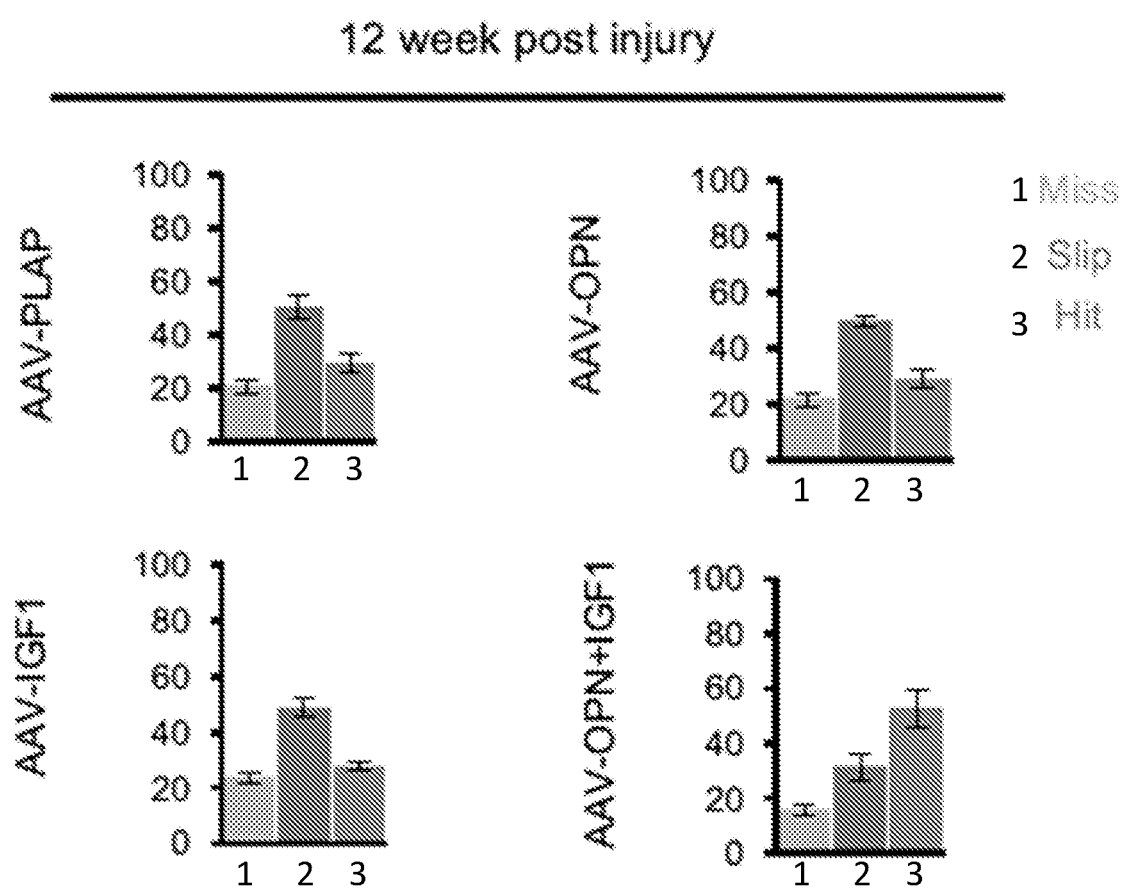
Figure 8A:
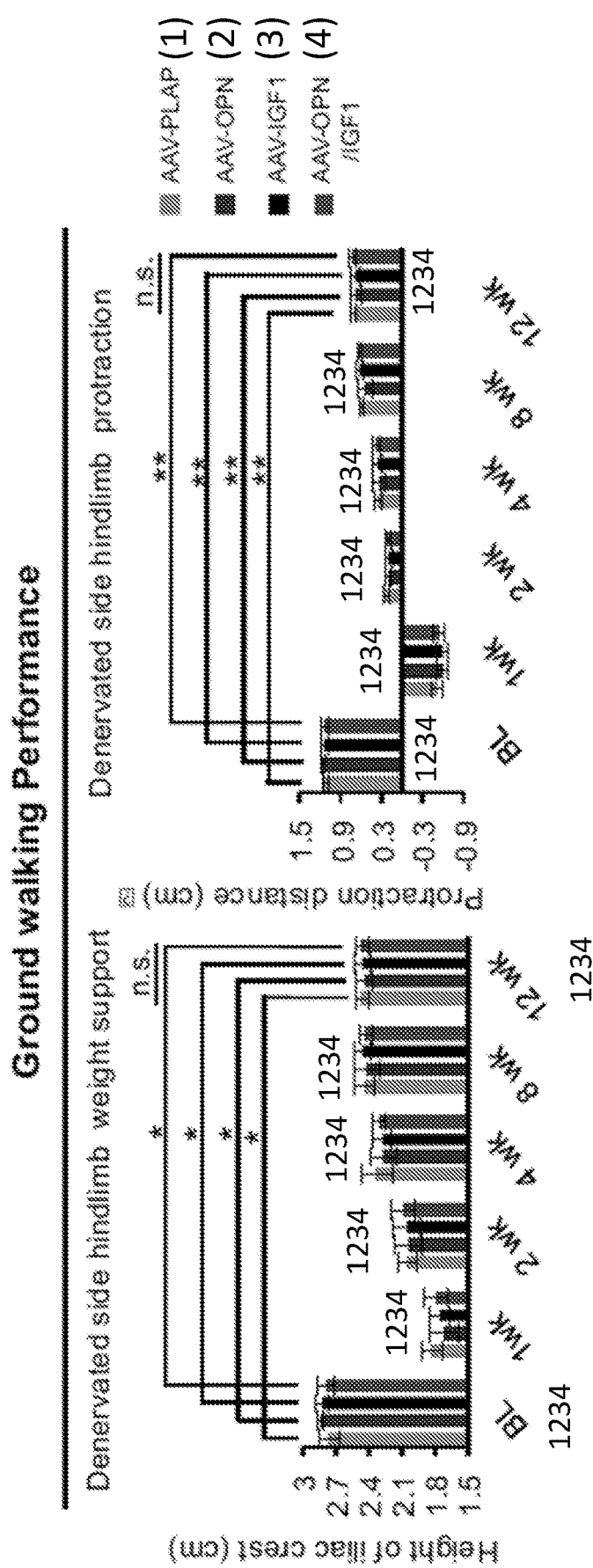
FIGS. 8A-8F present experimental results that indicate OPN/IGF1 treatment or acute pharmacological treatment had no effect on the partial functional recovery of gross locomotion after T10 lateral hemisection. (A) Hindlimb weight support and protraction from the denervated side were measured at pre- and 1, 2, 4, 8, and 12 wk post T10 lateral hemisection during overground walking. (B) Speed tolerance and hindlimb dragging (denervated side) at maximal speed were measured at pre- and 1, 2, 4, 8, and 12 wk post T10 lateral hemisection during treadmill walking. For (A-B): ** and *: p<0.01, and p<0.05, respectively. Repeated one-way ANOVA, followed by Bonferroni post hoc correction. n.s.: no statistical significance, one-way ANOVA. n=13, 9, 8, and 12 for AAV-PLAP, AAV-OPN, AAV-IGF1, and AAV-OPN/IGF1 treated groups, respectively.
Figure 8B:
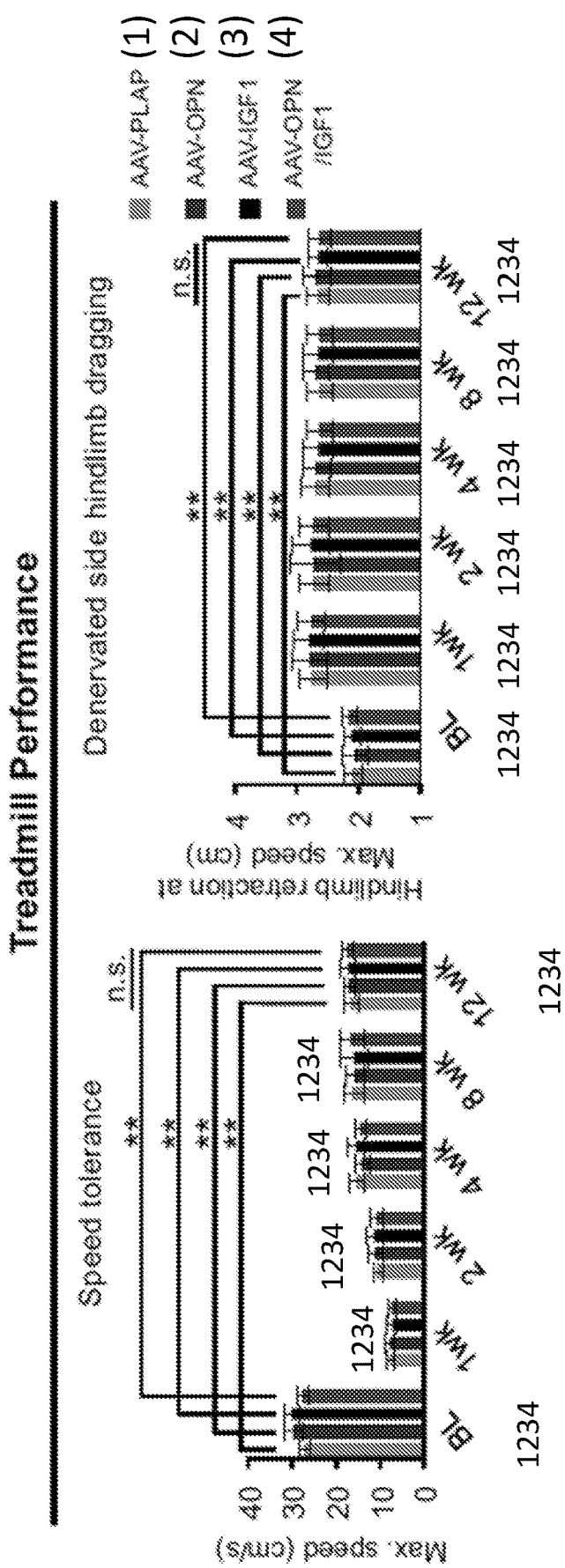
Figure 8C:
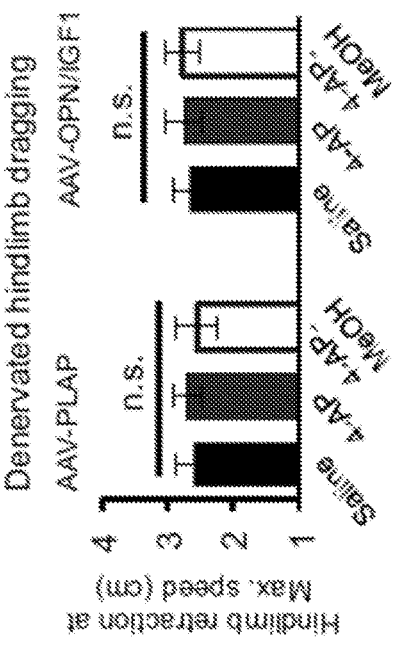
Figure 8D:
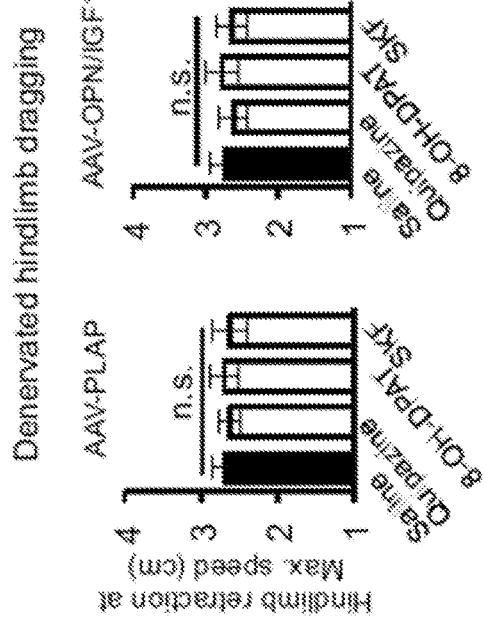

OPN/IGF1 Improve the Precision Position Performance and CST Regrowth After T10 Lateral Hemisection In contrast to unstable proteins, injected AAVs could express OPN and IGF1 for a few weeks. Thus the effects of AAV-assisted OPN/IGF1 treatment on CST regrowth and functional recovery in mice with T10 lateral hemisection were examined. As a first step, it was verified that AAV-mediated OPN/IGF1 treatment achieved similar level of IGFR and mTOR activation (FIGS. 6B-6D). To mimic clinical conditions, AAVs expressing placental alkaline phosphatase (PLAP, control) or OPN and/or IGF1 were stereotaxically injected to the sensorimotor cortex bilaterally 1 day after injury (FIG. 7A). These mice were subjected to behavioral tests biweekly in a double-blind manner. On the irregular walking task, the hindlimb performance of the intact side was similar in both control and treated groups, recovering spontaneously over 4-8 weeks (FIGS. 7B and 7C). However, there was a significant difference in the hindlimb performance of the denervated side in the double treated group from 8 weeks after injury (FIGS. 7D and 7E). In the group with treatment of both OPN and IGF1, the error rates dropped from about 86% at 1 week after injury to 46% at 12 weeks after injury, in contrast to a drop only ~70% in controls and groups treated with either OPN or IGF1 treatment (FIGS. 7B-7E). The improvements are specific to CST-mediated behaviors, in that mice in the OPN/IGF1 treated group failed to show significant improvements in weight support, hindlimb protraction of the denervated side during ground walking or speed tolerance and hindlimb retraction (denervated side) during treadmill walking when compared to other groups (FIGS. 8A and 8B).

Figure 9A:
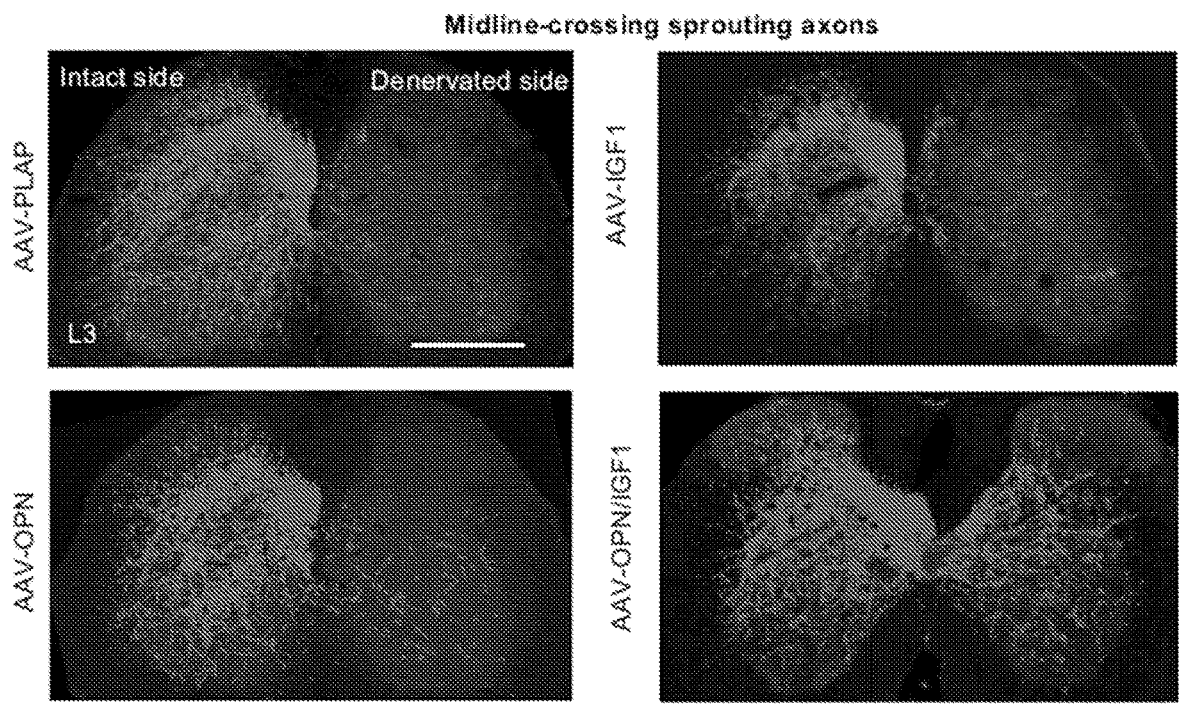
FIGS. 9A-9D present experimental results that indicate OPN/IGF1 treatment promotes CST regrowth after spinal cord T10 lateral hemisection. (A) AAV-ChR2-mCherry (visualized as red) or AAV-ChR2-YFP (visualized as green) was injected to the intact (assessing collaterally sprouted axons) or axotomized (assessing regenerating axons) cortex. Representative images in (A) of transverse sections of the lumbar spinal cord (L3) stained with anti-RFP and anti-GFP at 13-14 wk post spinal cord T10 lateral hemisection in AAV-PLAP, AAV-OPN, AAV-IGF1, and AAV-OPN/IGF1 treated groups. Notice that no GFP+ axons were detected at the denervated lumbar spinal cord. Scale bar: 500 µm. (B) Representative images of horizontal sections of the spinal cord around the lesion site (marked with star) stained with anti-GFP to mark regenerating axons at 13-14 week post spinal cord T10 lateral hemisection in each group. Scale bar: 1 mm. (C) Quantification of midline crossing axons counted in different regions of the lumbar spinal cord (L3 and L5) for each treatment group. The number was normalized against that of labeled CST axons counted at the pyramidal level (see the method section) in each condition. The schematic drawing on the upper-right corner illustrates the division of different regions of the spinal cord. Mid, midline: Z1 and Z2, different lateral positions. ** and *, p<0.01 and p<0.05, One-way ANOVA followed by Bonferroni post hoc test. n=3 per group. Five sections at L3 and L5 were quantified per mouse. (D) Quantification of labeled axons in the spinal cord caudal to the lesion site in each treatment group. *, p<0.05, repeated measures ANOVA followed by post hoc Bonferroni correction, n=3 mice per group. Five sections were quantified per mouse.
Figure 9B:
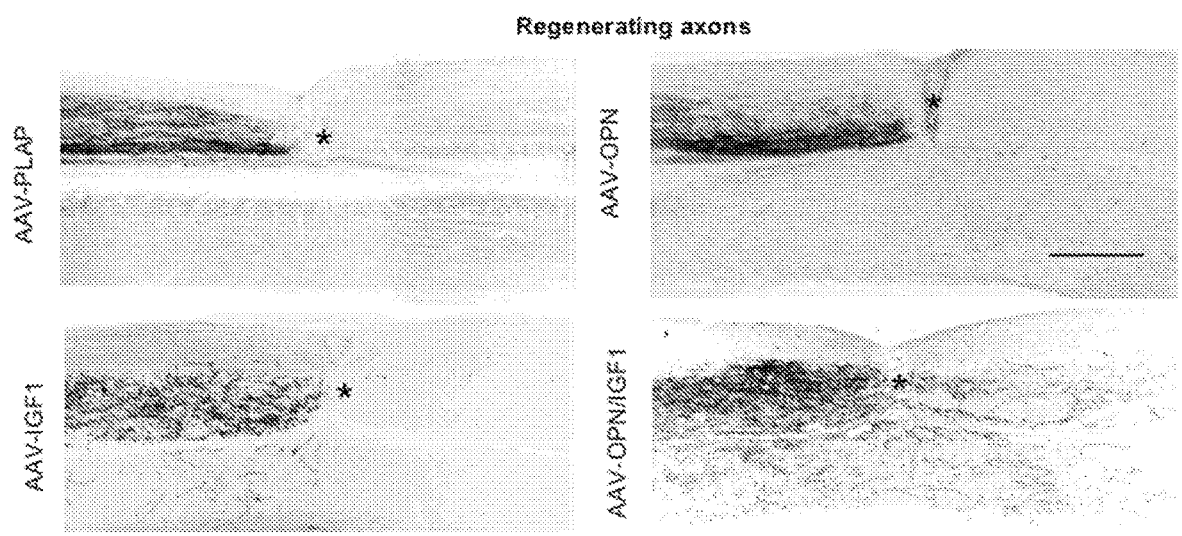
Figure 9D:
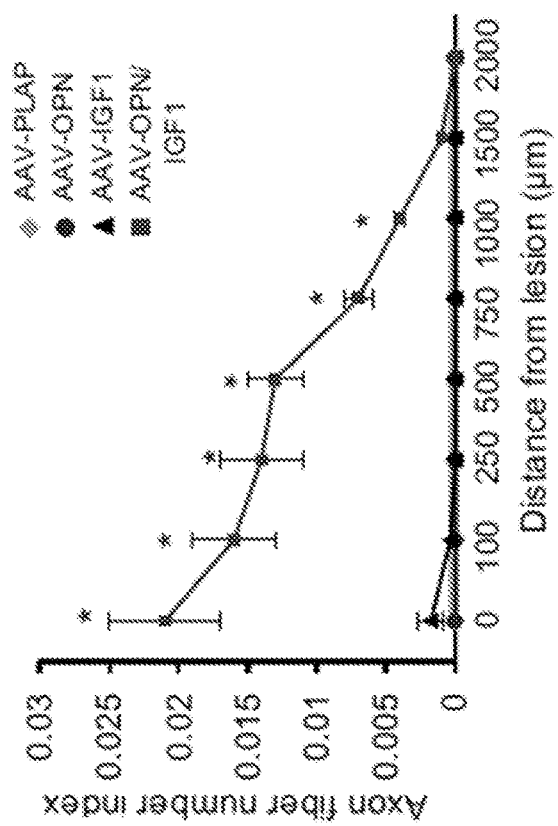
Figure 9C:
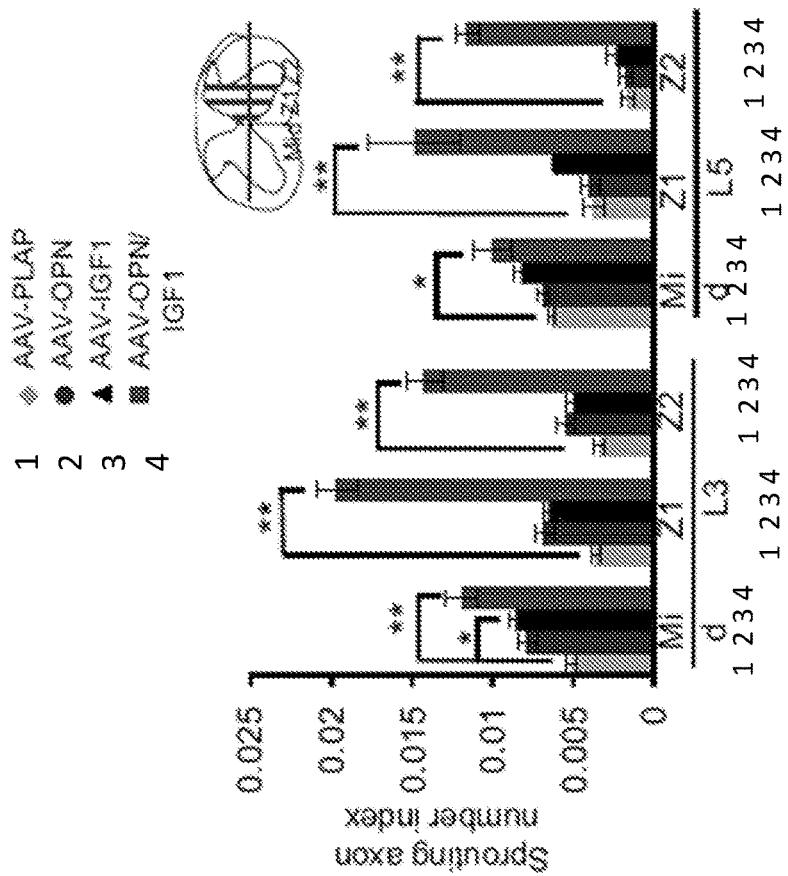

Since the mice treated with AAV-OPN/IGF1 were co-injected with AAV-channel rhodopsin (ChR2)-mCherry (AAV-ChR2-mCherry) or AAV-ChR2-YFP to the ipsi-lateral or contra-lateral cortex, respectively, at the termination of behavioral assessment, a post hoc examination of the T10 lateral hemisection histology was first performed. Mice with incomplete- or over-hemisection could be readily identified by analyzing labeled CST axons at the lumbar spinal cord and excluded from further analysis (FIG. 2A). CST regrowth was examined by preparing horizontal spinal cord sections covering the lesion sites to assess axon regeneration across the lesion site, and transverse sections of lower spinal cord segments to assess midline-crossing of CST axons from intact side. In controls and groups treated with either IGF1 or OPN, intact axons showed little sprouting across midline (FIGS. 9A and 9C) and injured axons showed significant die-back from the lesion site (FIGS. 9B and 9D). In contrast, significant numbers of injured axons regrew across the lesion in the OPN-IGF1 treated group (FIGS. 9B and 9D). However, while many of these axons projected for over 1 millimeter beyond the lesion (FIGS. 9B and 9D), they failed to reach the lumbar spinal cord (FIG. 9A). Importantly, in these mice with AAV-OPN and IGF1 treatment, CST axons from the intact side exhibited significant sprouting into the denervated side, which was observed across all spinal levels below the injury site (FIGS. 9A and 9C). These sprouted axons terminated broadly in different laminae at the lumbar spinal cord and formed bouton-like structures (FIG. 10B), as indicated by co-localization with vGlut1, a presynaptic marker for excitatory synapses (Maier et al., 2008; Liu et al., 2010) (FIGS. 10A and 10B). Thus, these sprouting axons play an important role in the observed functional recovery. Therefore, combined treatment of AAV-OPN and AAV-IGF1 not only promotes CST regrowth but also CST-dependent behavioral performance.

Figure 12B:
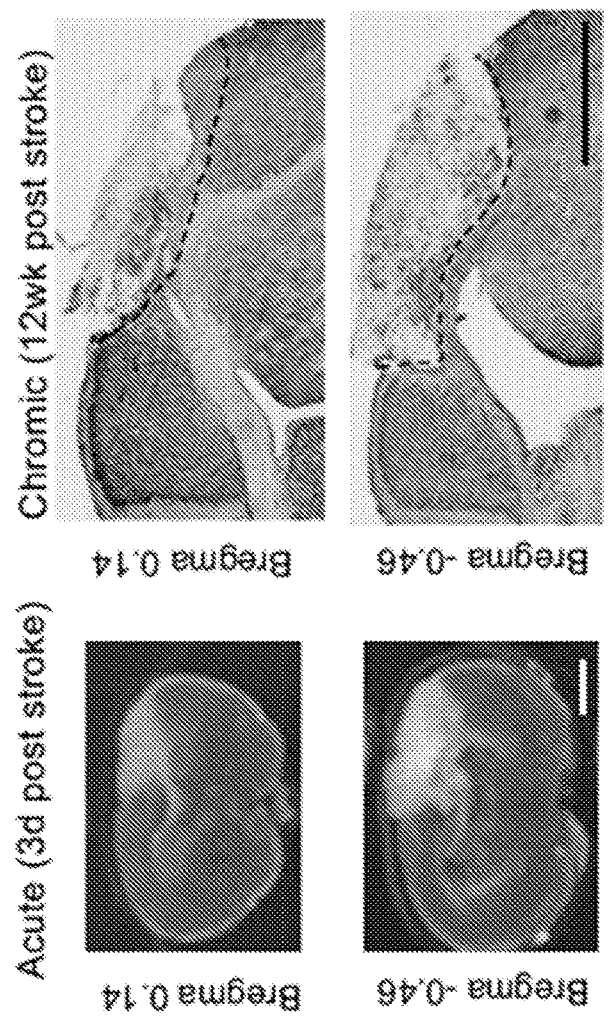
Figure 12A:
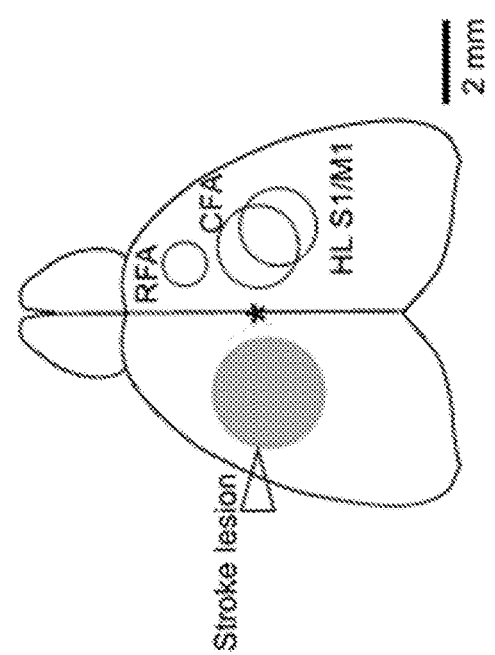

Further Improvements in Precision Performance in the OPN/IGF-treated Mice by 4-aminopyridine-3-methanol (4-AP-MeOH) Treatment Because mice treated with OPN and IGF1 showed partial improvement on the irregular ladder walking task (FIG. 7), whether additional treatments could further improve their performance was tested. As different neuro-modulatory small molecule compounds have been shown to impact locomotor function in SCI models (Fong et al., 2005; Courtine et al., 2009; Murray et al., 2010), several commonly used modulators were tested in the injured mice with AAV-OPN/IGF1 or AAV-PLAP treatments at 14 weeks post injury. Previous studies showed that systemic administration of a cocktail of serotonin receptor agonists and dopamine receptor agonists facilitates the transformation of lumbosacral circuits from dormant to highly functional states after injury (Musienko et al., 2011, van den Brand et al., 2012). However, quipazine, (a 5-HT2A agonist), 8-OH-DPAT (a 5-HT1A agonist), and SKF (a D1/D5 agonist) failed to improve their performance in irregular ladder, overground, or treadmill walking (FIGS. 11A, 11B, 8C and 8D), with one (SKF) even leading to deteriorated the hindlimb performance in irregular ladder walking on the denervated side (FIG. 12B).

Figure 11A:
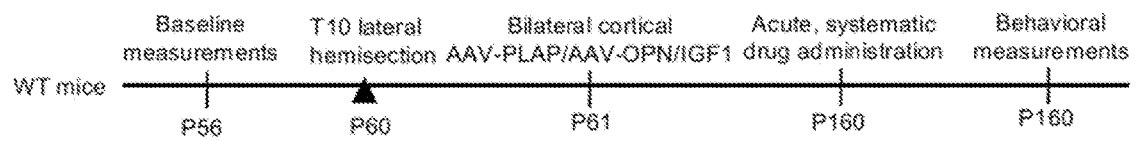
FIGS. 11A-11C present experimental results that indicate 4-AP-MeOH treatment further enhances precision performance in OPN/IGF1 treated animals. (A) Schematic diagram of the experimental timeline Wild type mice received baseline behavioral measurement at P50-P56, T10 spinal cord lateral hemisection at P60, bilateral cortical injection of AAV-PLAP or AAV-OPN/IGF1 at P61, pharmacological treatment at P160 and re-measurement of behavioral tests immediately after the treatment. (B-C) Performance on irregular walking of hindlimbs from both intact and denervated sides in AAV-PLAP and AAV-OPN/IGF1 treated groups with systematic administration of saline, 5-HT receptor agonists (B, quipazine and 8-OH-DPAT), dopamine receptor agonist (B, SKF), 4-AP (C) and 4-AP-MeOH (C). n.s. and *, no statistical differences, and p<0.05, respectively. One-way ANOVA followed by post hoc Bonferroni correction (to the saline treated group), n=7, and 8 for AAV-PLAP and AAV-OPN/IGF1 treated groups.
Figure 11B:
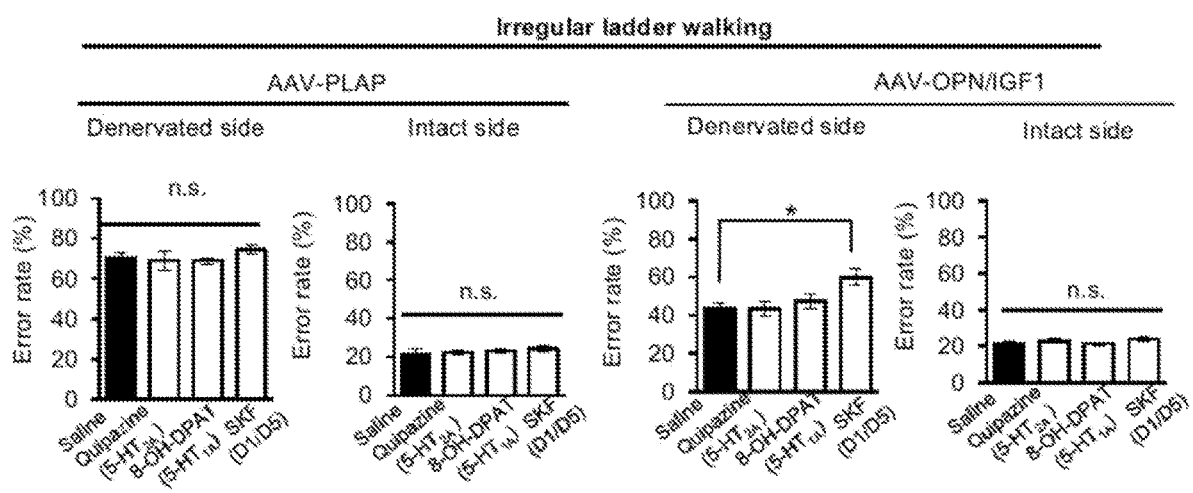
Figure 11C:
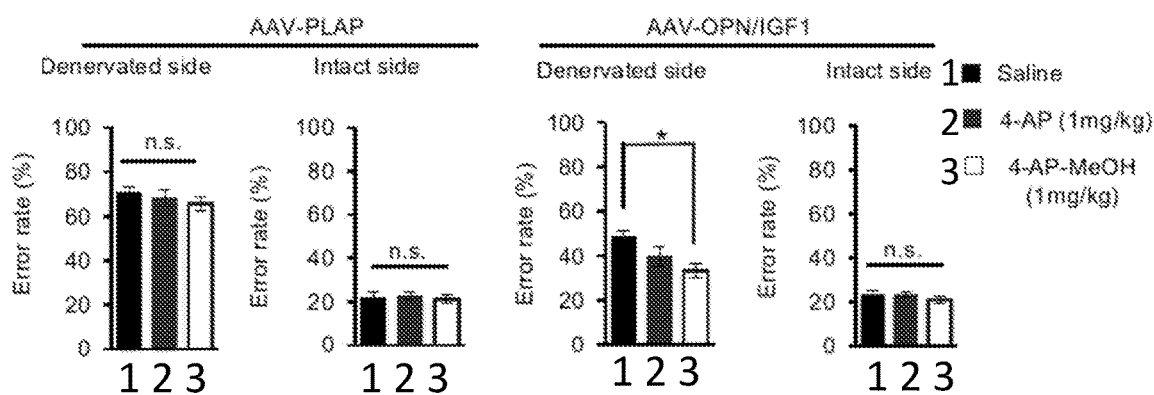

Previous studies in an optic tract injury model showed that 4-aminopyridine (4-AP) or its derivative 4-aminopyridine-3-methanol (4-AP-MeOH), both voltage-gated potassium channel blockers (Bostock et al., 1981; Sun et al., 2010), were able to improve nerve conduction of regenerated retinal axons and led to behavioral improvements in a visual task (Bei et al., 2016). Thus, whether these compounds could improve performance in locomotor tasks was tested. As shown in FIGS. 10E and 10F, neither 4-AP nor 4-AP-MeOH had significant effects on the recovery of treadmill walking performance when compared to the control. However, on the irregular ladder walking task, 4-AP at the dose of 1 mg/kg showed a trend of reducing the error rates in mice with OPN/IGF1 treatment, but failed to reach statistical significance (FIG. 11C). Reliable results with higher doses of 4-AP treatments were not obtained because of seizures as a result of such treatments in injured mice. However, in the OPN/IGF1 treated group, at the dose of 1 mg/kg, 4-AP-MeOH treatment significantly reduced the error rate from about 48% to 30% (FIG. 11C), approaching to the intact hindlimb performance (error rate about 20%). These results indicate that improving the conduction of regrowing CST axons can facilitate the recovery of CST-dependent skilled locomotor function.

Figure 15A:
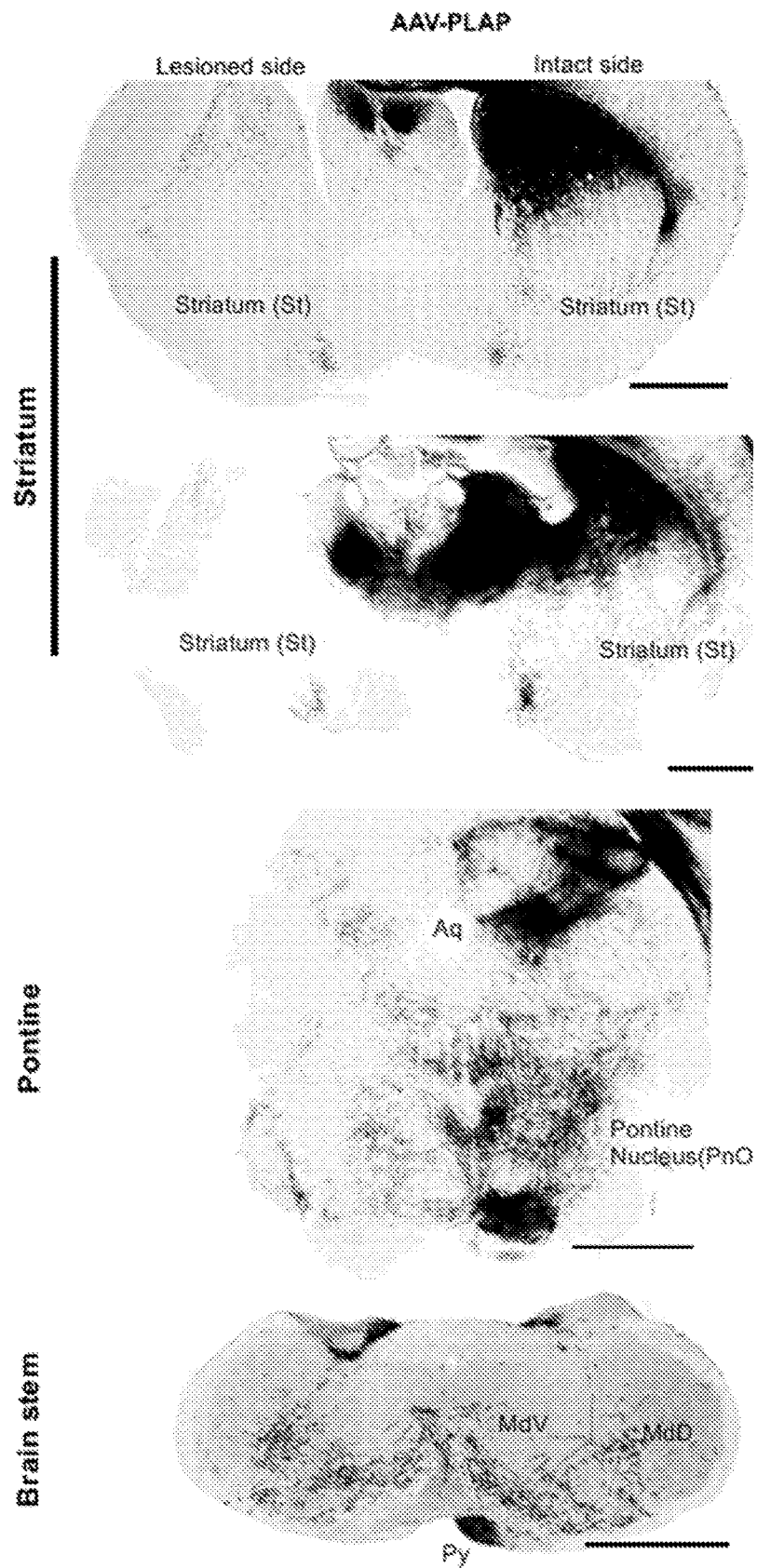
FIGS. 15A and 15B present experimental results that indicate OPN/IGF1 treatment promotes CST axon sprouting in subcortical areas after unilateral cortical stroke. (A-B) AAV-ChR2-mCherry was injected to the intact cortex 3d post stroke. Representative images of transverse sections containing axonal projections at the striatum, the pontine, and the brainstem stained with anti-RFP in AAV-PLAP (A) and AAV-OPN/IGF1 (B) treated animals. St: striatum, Aq: cerebral aqueduct: PnO: pontine reticular nucleus: MdD and MdV: medullary reticular formation, dorsal and ventral parts. Py: pyramidal tract. Scale bars: 1 mm.
Figure 15B:
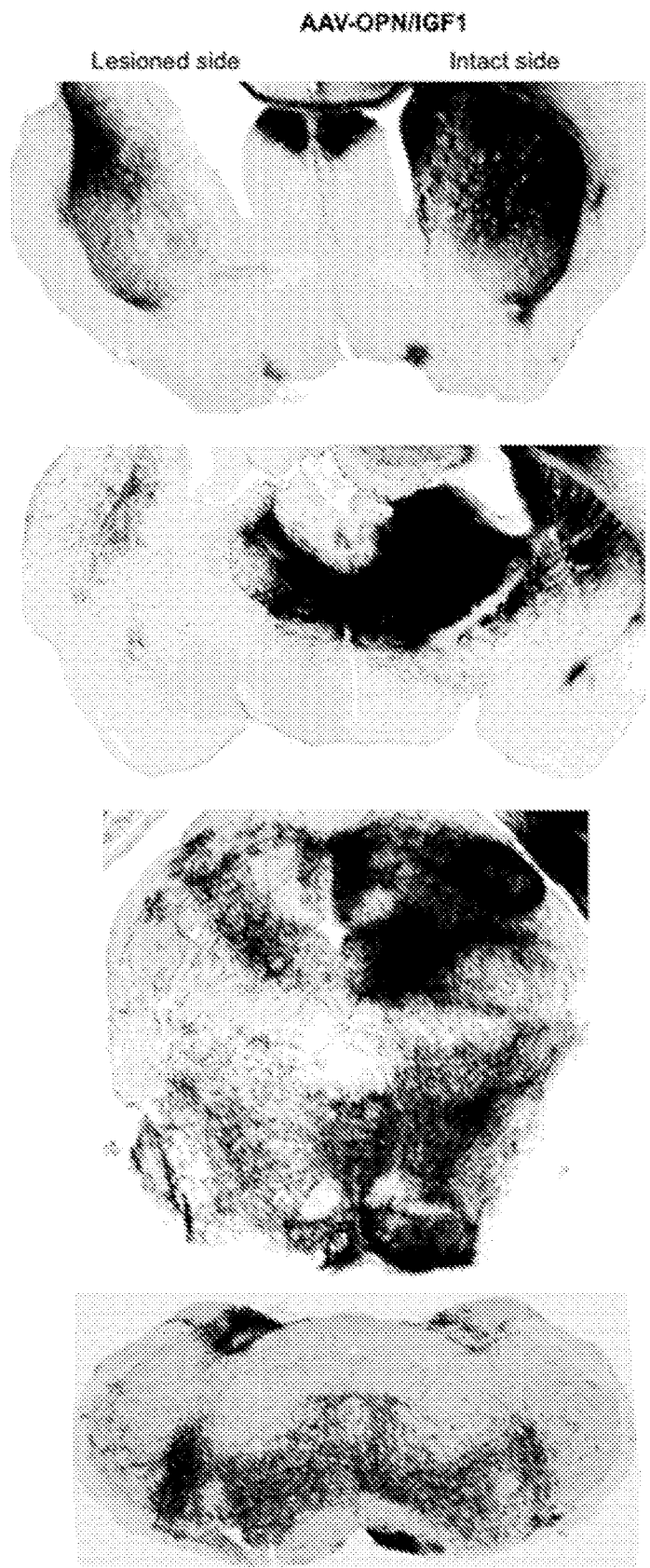

AAV-OPN/IGF1 Stimulates the Sprouting of Cortical Axons and Improves Functional Recovery in a Cortical Stroke Model Results from T10 hemisection prompted the testing of whether OPN/IGF1 treatment might be beneficial in cortical stroke models in which CSNs and their axons are disrupted. With a photothrombosis-based protocol, previous studies have established a reproducible cortical infarction that destroys the sensorimotor cortex unilaterally leading to deficits in skilled locomotor function (Watson et al., 1985; Li et al., 2015; Wahl et al., 2014). This procedure was optimized in adult mice (FIG. 12A) and resulted in consistent lesion of the sensorimotor cortex, as evident by both TTC staining (3 days post lesion) and Nissl staining (12 weeks post lesion) (FIG. 12B). Behaviorally, these lesioned mice exhibited significant unilateral defects on the irregular ladder walk task for both forelimbs and hindlimbs (FIG. 15C), and the food pellet retrieval task for the forelimbs (FIG. 12D), which is highly relevant to CST function (Farr and Whishaw, 2002, Wahl et al., 2014). In contrast, mice gained almost full functional recovery over ground locomotion (FIG. 12E).

Figure 13D:
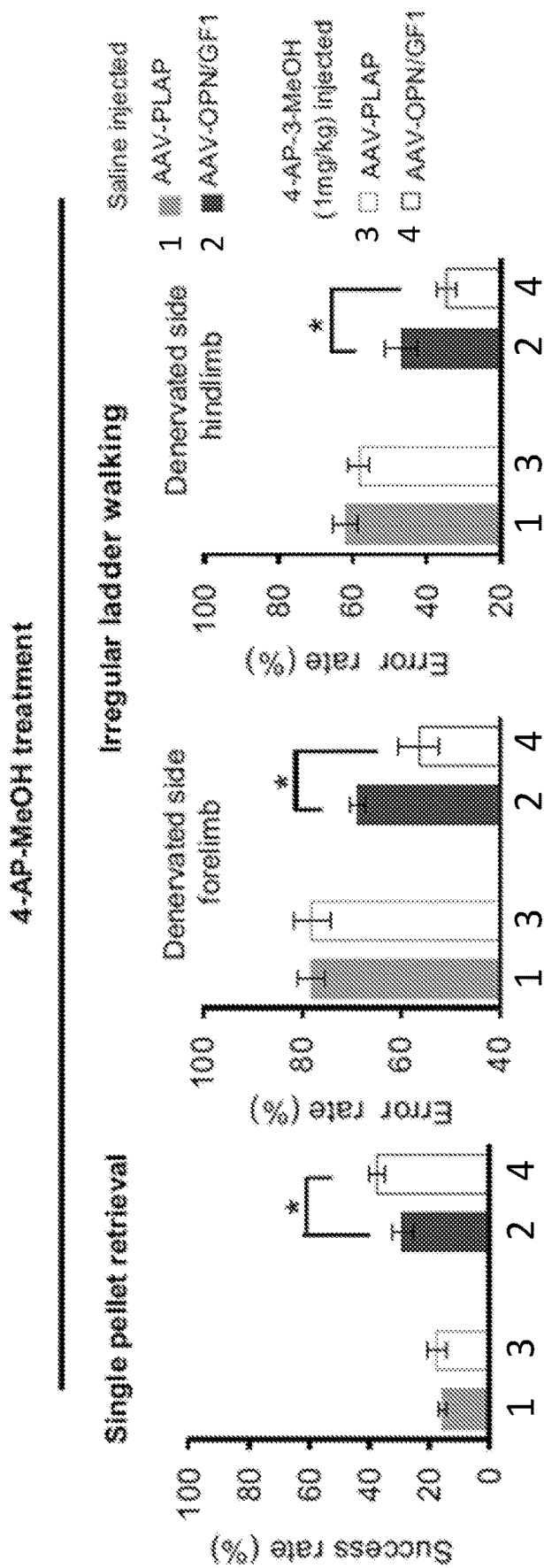
Figure 14A:
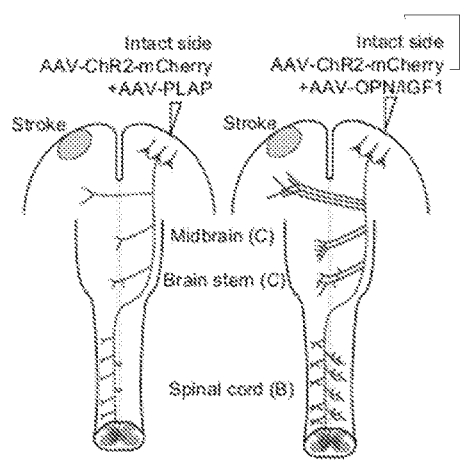
FIGS. 14A-14E present experimental results that indicate OPN/IGF1 treatment promotes CST axon sprouting in the spinal cord and subcortical areas after unilateral cortical stroke. (A) Schematic drawing of the experimental procedure. The cortical injection (intact side) of AAV-PLAP (Left) or AAV-OPN/IGF1 (right), along with AAV-ChR2-mCherry was performed 3 days after the unilateral photothrombotic stroke Notice the collateral sprouting occurred at the striatum, the midbrain, the brain stem, and the spinal cord from the corticospinal/corticofugal axons after the injury in control (AAV-PLAP) and experimental (AAV-OPN/IGF1) conditions. (B-C) Representative images of serial transverse sections at the spinal cord (C6 and L3, B), the midbrain, and the brain stem (C) stained with anti-RFP in AAV-PLAP and AAV-OPN/IGF1 treated animals Scale bar in B: 500 μm, in C: 1 mm. Aq: cerebral aqueduct, mRT: mesencephalic reticular formation; GiV: gigantocellular reticular nucleus. Sp5O: spinal trigeminal nucleus; and Py: pyramidal tract. (D) Quantification of fluorescence intensity of corticofugal projections from the intact side at multiple subcortical areas in AAV-PLAP and AAV-OPN/IGF1 treated animals. For each subcortical position, fluorescence intensity was normalized to that of the cortical area injected with AAV-ChR2-mCherry. St: striatum; R: red nucleus, PnO: pontine reticular nucleus; GiV: gigantocellular reticular nucleus; Sp5O: spinal trigeminal nucleus; MdD and MdV: medullary reticular formation, dorsal and ventral parts. Note: images of St, PnO, MdD and MdV from AAV-PLAP or AAV-OPN/IGF1 injected animals are in FIGS. 15A and 15B. , p<0.01. Student's t-test. n=3 mice per group. Five sections at C7 and L3 were quantified per mouse. (E) Quantification of midline crossing axons counted in different regions of the cervical and lumbar spinal cord (C6 & L3) in AAV-PLAP and AAV-OPN/IGF1 injected groups.  and *, p<0.01 and p<0.05, Student's t-test. n=3 mice per group. Five sections at C6 and L3 were quantified per mouse.
Figure 14B:
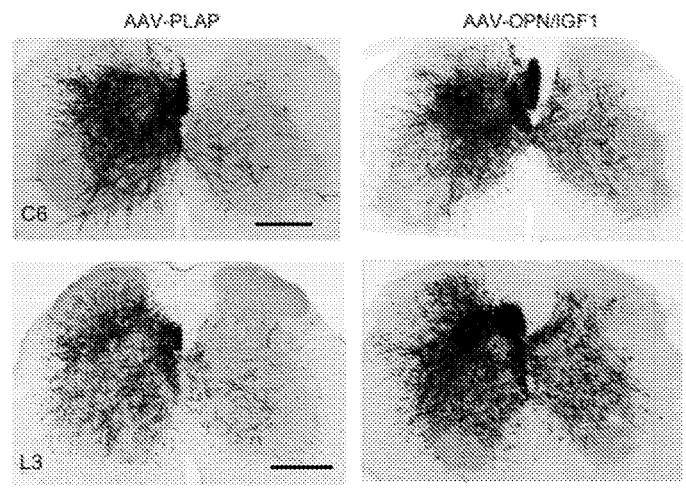
Figure 14C:
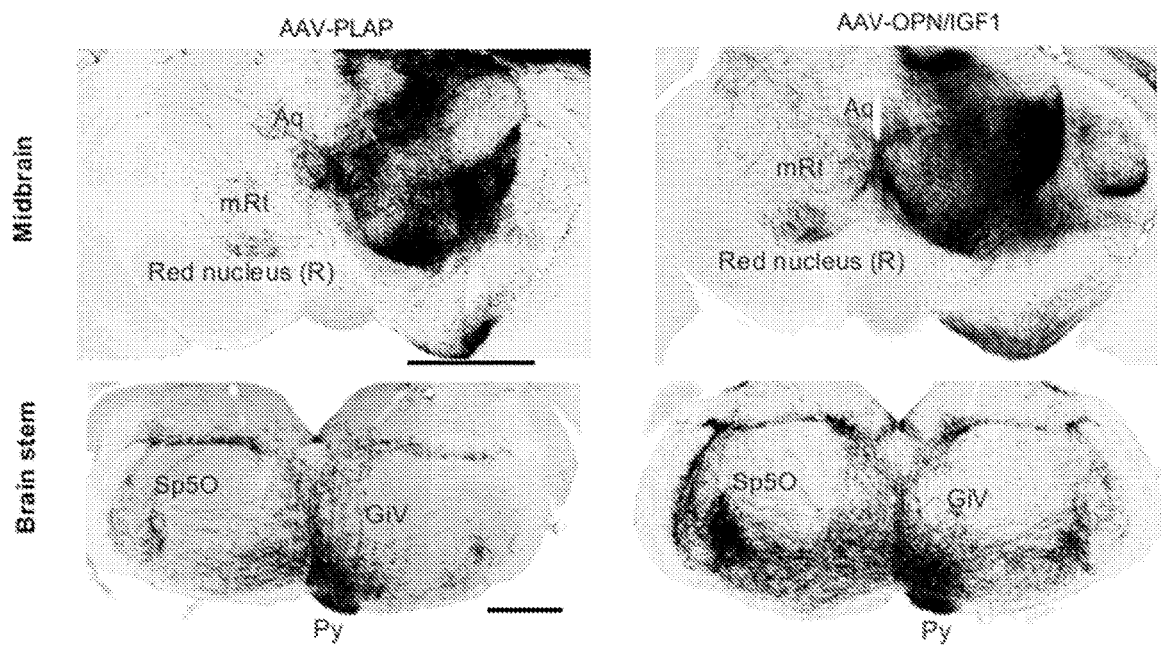
Figures 14D, 14E:
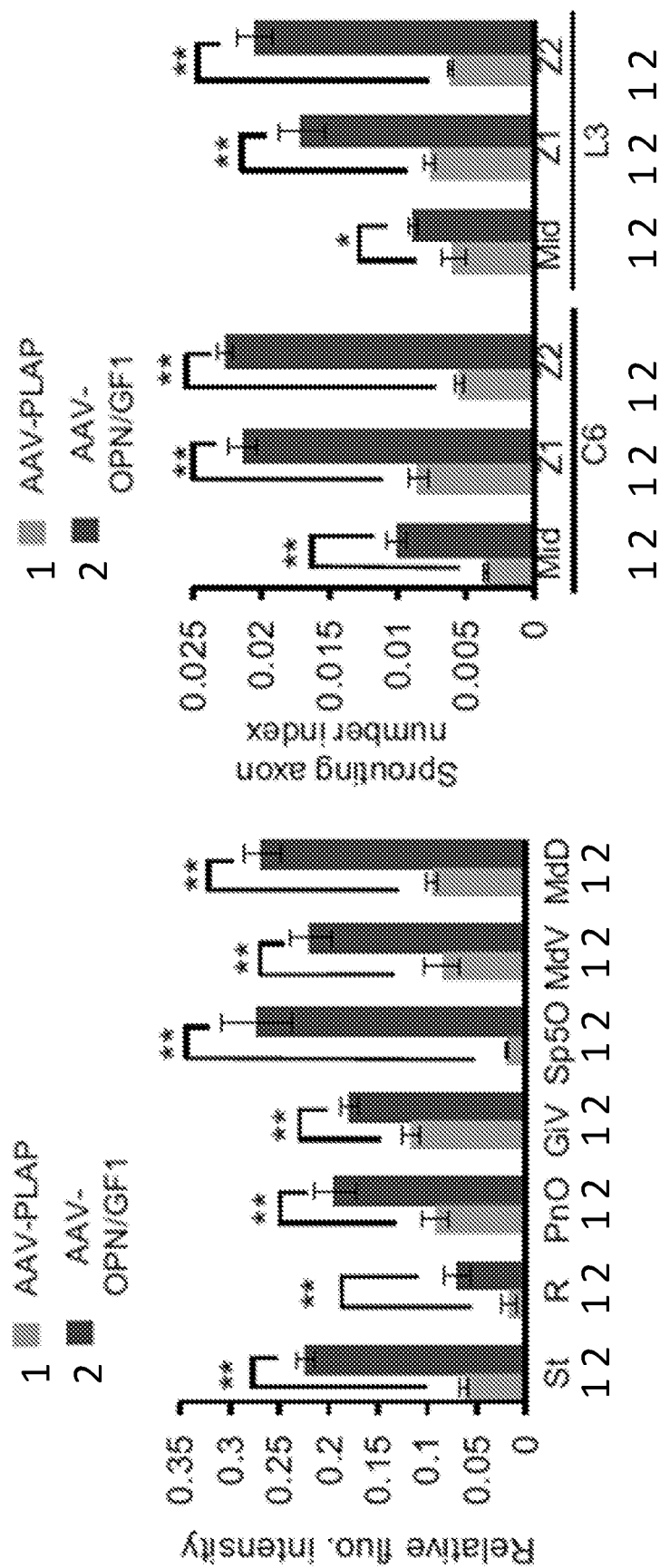

To test whether OPN/IGF1 treatment could promote recovery following stroke, AAVs expressing OPN/IGF1 (treatment group) or PLAP (control) were injection into the intact sensorimotor cortex at 3 days after photothrombotic cortical lesion (FIG. 6A). Treatment with OPN/IGF1 resulted in significant recovery in both behavioral assays, starting from 8 weeks after injury (FIGS. 13B and 13C). Furthermore, similar to treated mice with T10 lateral hemisection (FIGS. 11A-11C), the addition of 4-AP-MeOH resulted in further improvements on both assays (FIG. 13D) in these ischemic mice treated with OPN/IGF1.

At 12 weeks after the lesion, these mice were subjected to anatomical analysis. As AAV-ChR2-mCherry vectors were co-injected with AAV-OPN/IGF1 or AAV-PLAP to the intact side of the cortex (FIG. 14A), projection patterns of the labeled cortical axons could be monitored. As shown in FIGS. 14A-14E, 15A and 15B, AAV-ChR2-mCherry-labeled axons from the intact treated sensorimotor cortex showed increased sprouting not only in the cervical and lumbar spinal cord (FIGS. 14B and 14E), but also in other subcortical regions such as the medullary reticular formation (both ventral and dorsal parts; MdV & MdD, bilaterally), the spinal trigeminal nucleus (Sp5O, bilaterally) and the gigantocellular reticular nucleus (GiV, bilaterally) in the brainstem, the ipsilateral (relative to the AAV-mCherry injected side) pontine nucleus (PnO), the contralateral red nucleus (R) and ipsilateral superior colliculus (SC) in the midbrain, and the striatum (St) beneath the lesioned cortex (FIGS. 14C, 14D and 15A and 15B).

Contribution of CST Sprouting in the Cervical Spinal Cord to the Functional Recovery Induced by OPN/IGF1

The observed axon sprouting in subcortical regions such as the red nucleus and brainstem might relay the cortical signal to the denervated spinal cord. This raised the possibility that these new pathways could mediate functional recovery instead of, or along with connections resulting from sprouting in the spinal cord (Garcia-Alias et al., 2015). To assess the contribution of sprouted CST axons in the spinal cord to the observed functional recovery, the effects of ablating CSNs that send collaterally sprouted axons to the denervated side of the cervical spinal cord (C5-C7) were analyzed using a viral vector-assisted intersectional targeting strategy (Kinoshita et al., 2012; Wahl et al., 2014). Using an optimized stereotaxic injection protocol (Jin et al., 2015), pseudotyped HiRet-FLEX-DTR) was first unilaterally injected into the denervated side of the cervical spinal cord (C5-C7) at 14 weeks post injury (FIG. 16A) in a set of adult mice with AAV-OPN/IGF1 treatment as described above. 3 days later, AAV-Cre (Ablation) or AAV-PLAP (Control) was then injected into the unlesioned side cortex (FIG. 16A). 2 weeks later, Diphtheria toxin (DT) was administered intraperitoneally. This resulted in only Cre+ CSNs that sprouted midline-crossing axons into the cervical, but not lumbar, spinal cord would express DTR, which would be ablated by DT injection. The behavioral performance was unaltered by these intraspinal and cortical injections (FIGS. 16B and 16C).

Figure 16B:
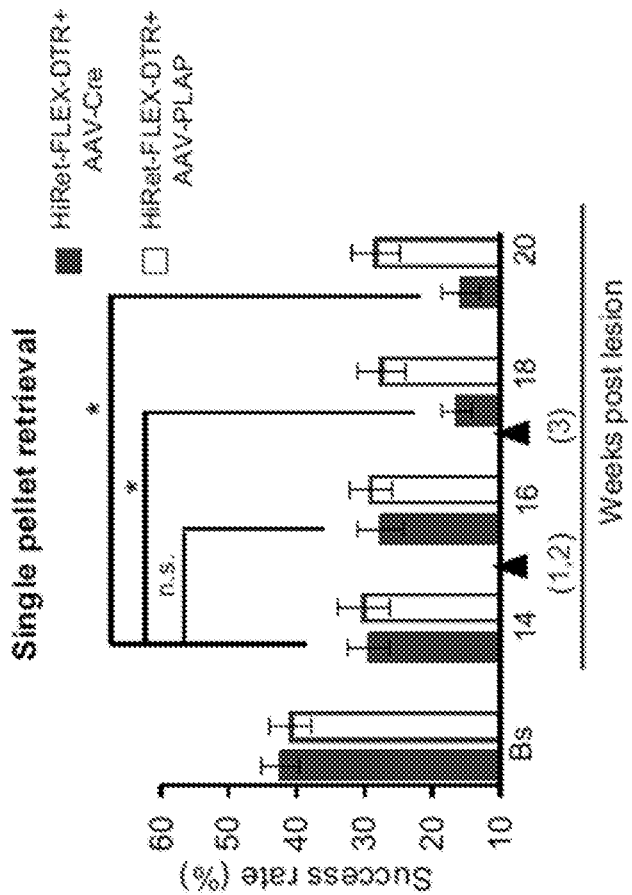
Figure 16A:
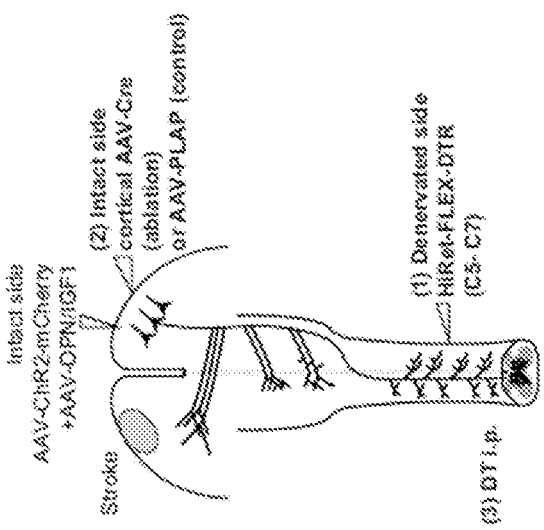
Figure 16C:
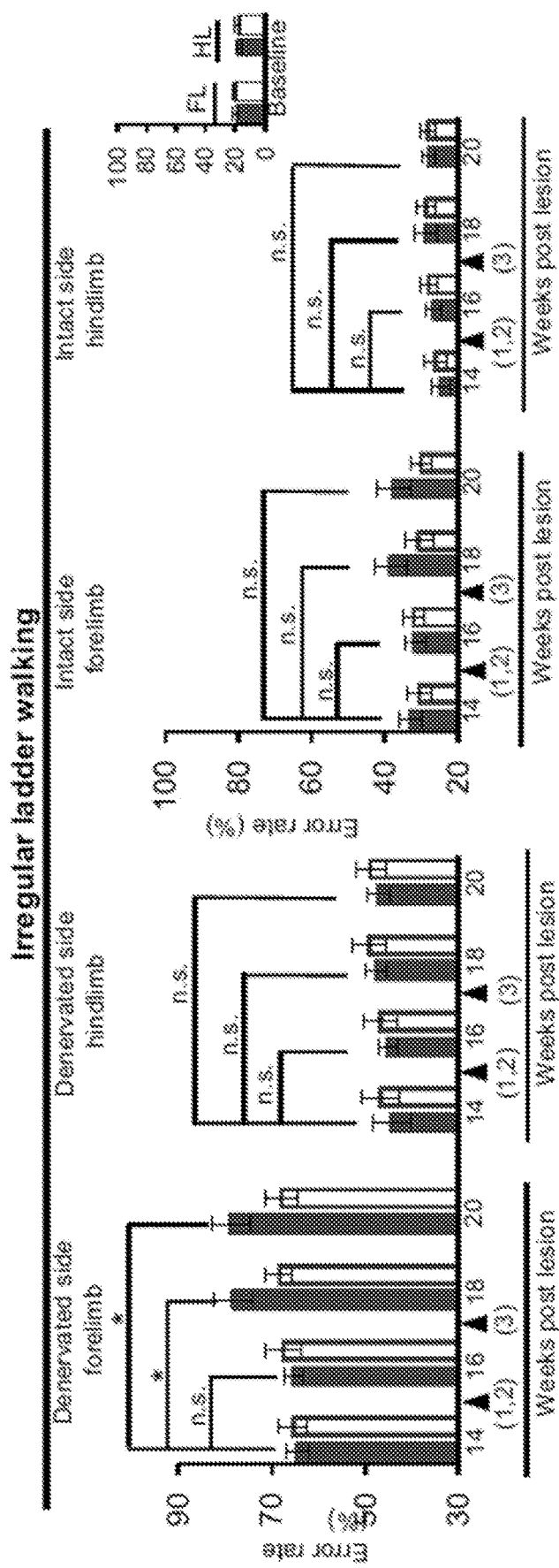
Figure 17A:
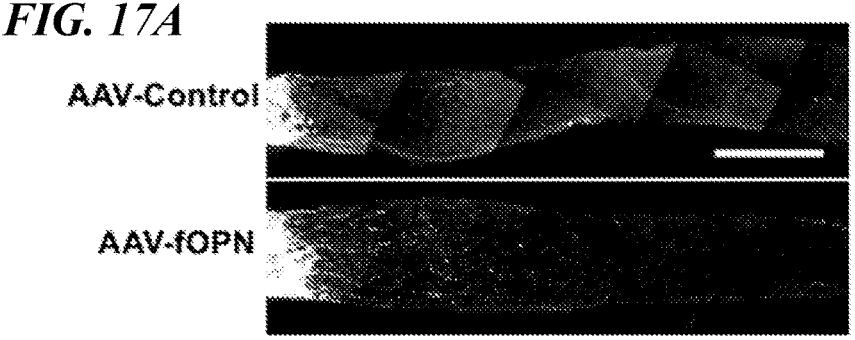
FIGS. 17A-17J present experimental results that indicate significant optic nerve axon regeneration after combined treatment of AAV expressing full length OPN (AAV-fOPN) and recombinant IGF1 (rIGF1), or combined treatment of AAV-fOPN and rBDNF. No significant regeneration was observed for any of the other treatments. Scale bars, 0.3 mm. * p<0.05. p<0.01, * p<0.001, ANOVA.
Figure 17C:
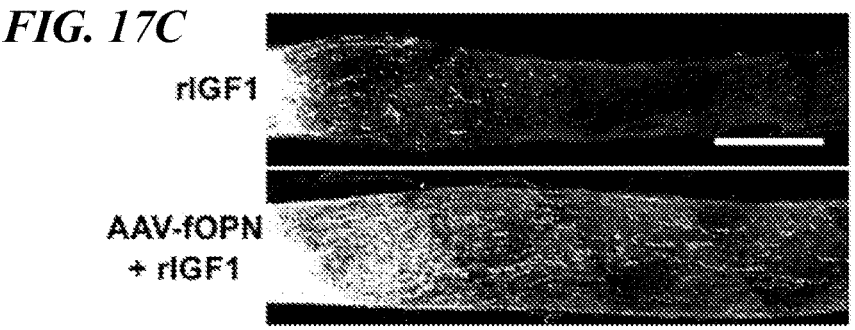
Figure 17E:
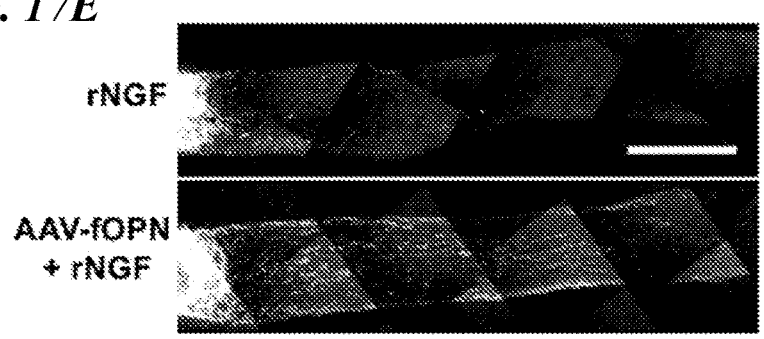
Figure 17G:
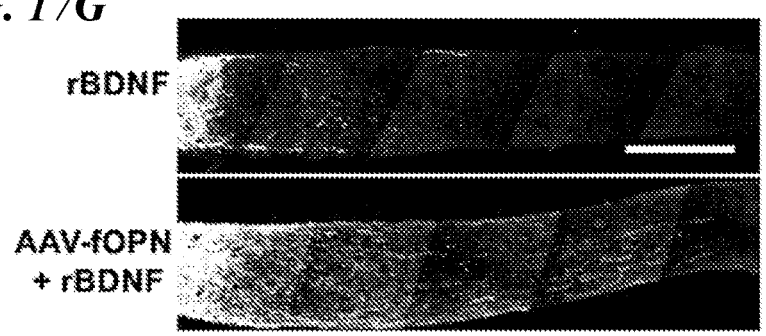
Figure 17I:
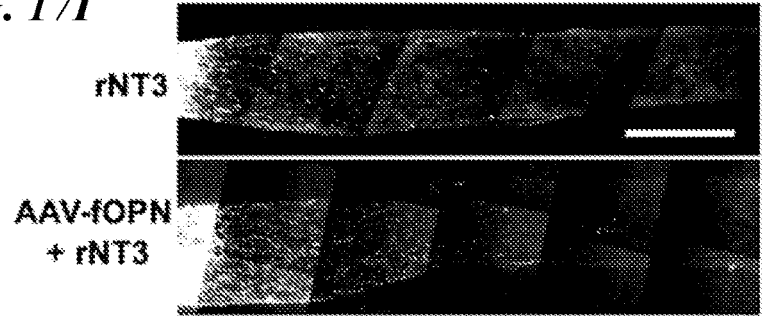
Figure 17B:
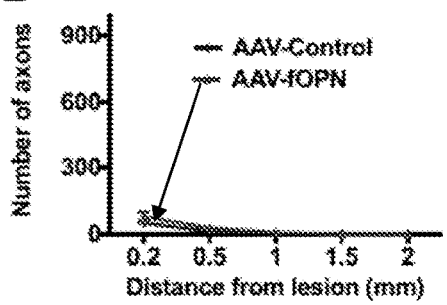
Figure 17D:
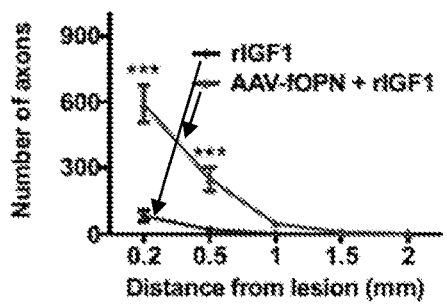
Figure 17F:
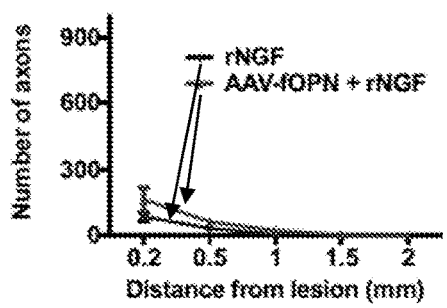
Figure 17H:
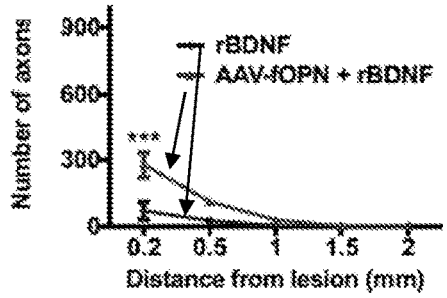
Figure 17J:
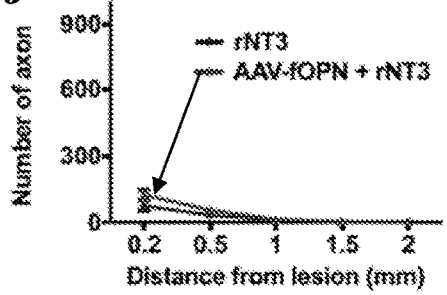

However, at two weeks after DT administration, the improved performance by OPN/IGF1 treatment on single pellet retrieval task and irregular ladder walking of the denervated forelimb significantly declined (FIGS. 16B and 16C). Such ablation-induced behavioral decline was seen only in the forelimbs, but not the hindlimbs (FIG. 16C). Consistently, the ablation of CST axons was seen in the denervated side of the cervical, but not lumbar, spinal cord (FIGS. 16D-16F), likely due to the fact that HiRet-FLEX-DTR was selectively injected to the cervical spinal cord. The performance of the intact forelimb on irregular ladder walking showed a decreasing trend, although without statistical difference (FIG. 16C). In this regard, CST axons on the intact side of the cervical spinal cord were also found to be reduced (FIGS. 16D-16F), consistent with the notion that the CST axons in the denervated side were primarily sprouted from the intact side of the spinal cord. Thus, although a contribution of sprouting axons in the subcortical regions for functional improvement cannot be ruled out, these results indicate that the sprouted axons in the spinal cord are required for the recovery of skilled motor performance after unilateral photothrombotic stroke.

DISCUSSION

Previous studies have shown that, by neutralizing inhibitory factors in the environment and elevating neuronal activity of affected neurons, several methods are able to promote regrowth of CST axons and resultant functional recovery after spinal cord injury and cortical stroke (Garcia-Alias et al., 2009; Wahl et al., 2014; Carmel et al., 2010, 2014; Li et al., 2015). In this study experimental evidence showing the efficacy of activating the intrinsic growth ability of adult CSNs to achieve functional recovery in both spinal cord injury and stroke models was obtained. Because both OPN and IGF1 are soluble proteins, they serve as the basis for a highly translatable avenue of promoting neural repair.

N-OPN Sensitizes CSNs' Responses to IGF1

Despite the fact that IGF1 could promote axon growth from cultured CSNs isolated from neonatal mice (Ozdinler and Macklis, 2006), it failed to promote CST regrowth in adult mice in vivo, consistent with previous findings (Hollins et al., 2009; Li et al., 2010). Thus, an important difference was revealed between young and adult neurons in the CNS, in terms of their responsiveness to growth factors. In this regard, previous studies indicated that despite well-established roles of neurotrophins and other growth factors in promoting neuronal survival in young and cultured neurons, these factors have limited efficacy in protecting neurons in disease models such as ALS (Thoenen and Sendtner, 2002). The results presented herein indicate that OPN could partially improve neuronal responsiveness to IGF1. Osteopontin is able to sensitize CSNs' signaling responses to IGF1, as indicated by both increased phosphorylation of IGF1 receptor and S6 kinase (FIGS. 5A-5E, 6B, and 9D), which indicates that it acts on the plasma membrane of CSNs. Previous studies revealed that OPN can interact with different types of integrins and other cell adhesion molecules such as CD44 (Kazanecki et al., 2007; Wang and Denhardt, 2008; Kahles et al., 2014). In non-neuronal cells, IGFR and integrins have been shown to be associated with lipid rafts (Salani et al., 2009). Thus, without wishing to be bound by theory, it is hypothesized that by interacting with integrins or other cell surface proteins, OPN could mobilize or cluster the IGF1 receptors so that their responsiveness to the ligand is enhanced.

CSN Dependent Behavioral Tasks

Despite ample evidence of CSNs and their CST projections functioning in skilled forelimb locomotion, CST-dependent behavioral tasks of the hindlimbs are not well characterized. Presented herein is evidence that adult mice with ablated CSNs innervating low thoracic and lumbar spinal cord showed selective defects in an irregular walking task, in which these mice have to constantly rely on cortically mediated sensorimotor integration to avoid missteps. These results indicate a role of corticospinal projections in precision walking tasks (Liddle and Phillips, 1944, Georgopoulos and Grillner, 1989; Drew et al., 1993; Carmel et al., 2010; 2014).

Furthermore, mice with T1O lateral hemisection were demonstrated to have little spontaneous sprouting of CST axons across the midline and exhibit persistent behavioral deficits in this irregular walking task, indicating a causal relationship between such anatomical and behavioral events. This is further supported by the finding that sensitized IGF1 treatment is able to promote CST regrowth and specific functional recovery in both T10 lateral hemisection and unilateral cortical stroke models. In the case of T10 lateral hemisection, OPN/IGF1 treatment elicited both regenerative growth from injured CST axons and compensatory sprouting from spared axons. However, regenerated axons grew only a few millimeters, far away from the lumbar segments, and were thus unlikely to contribute to the observed functional recovery. On the other hand, in both T10 lateral hemisection and unilateral cortical stroke models, midline-crossing axons sprouted from the intact side robustly innervated the denervated side in different spinal cord levels. The finding that restored skilled locomotion function was dependent on CSNs that sprouted midline-crossing axons into the cervical spinal cord in the unilateral cortical stroke model (FIGS. 16A-16F) reinforces the reparative effects of promoting sprouting responses of spared axons in these disease models.

Combinatorial Strategies of Maximizing Functional Recovery

Considering sub-optimal numbers of regrowing axons and their un-refined termination patterns, it is not surprising that only partial functional recovery was observed with OPN/IGF1 treatment. Instead of pharmacological treatments that increase neuronal excitability, those that improve nerve conduction were able to further improve behavioral performance. As sprouted axons are unlikely to make functional connections with their original targets in numbers approximating normal circuitry, improving axon conduction may facilitate the transmission of cortical commands carried by these detour connections in the spinal cord. Importantly, compared to clinically approved 4-AP with more serious side effect (Blight et al. 1991; Donovan et al. 2000), 4-AP-MeOH showed significantly better effects with broader safety doses, and should be considered as a candidate for further clinical investigations. In addition, rehabilitation-based methods have been shown as an additional means to facilitate functional recovery in an activity-dependent manner (Cai et al., 2006; Garcia-Alias et al., 2009; Courtine et al., 2009; Wahl et al., 2012, van den Brand et al., 2012; Rossignol et al., 2015). In summary, results described herein demonstrate a translatable strategy of achieving functional restoration that is applicable for the treatment of both spinal cord injury and stroke.

Materials and Methods

Mouse Strains. All experimental procedures were performed in compliance with animal protocols approved by the Institutional Animal Care and Use Committee at Boston Children's Hospital or National Institution of Health. C57B1/6 wild type mouse (Charles River, Strain code #027) and Emx1-Cre (Jax #5628), mouse strains were maintained on C57B1/6 genetic background. For behavioral measurement, experimental animals used were from different littermates. The body weight and sexes were randomized and assigned to different treatment groups, and no other specific randomization was used for the animal studies. Behavioral tests were videotaped and examined blindly.

Chemicals and Antibodies. For systematic administration (i.p.), Quipazine [Sigma (Q1004), 0.2 mg/kg], SKF-82197 [Tocris (1447) 0.1 mg/kg], and 8-OH-DPAT [Tocris (0529), 0.1 mg/kg), 4AP [Sigma (275875), 1 mg/kg, 3 mg/kg), 4AP-MeOH [Santa Cruz (sc-267247), (1 mg/kg)] were dissolved in saline. Tamoxifen (Sigma, 10540-29-1) was dissolved in oil. For diphtheria toxin mediated cell ablation, we purchased the diptheria toxin from Sigma (D0564). For immunostaining, the primary antibody used were chicken anti-GFP [Abcam (Cat: ab13970)], rabbit anti-RFP [Abcam (Cat: ab34771)], rabbit anti-PKCγ [Santa Cruz (sc211)], rabbit anti-GFAP [DAKO (Z0334)]; rabbit anti-5-HT [Immunostar (20080)], rabbit-anti-IGFR [Santa Cruz (sc-712)] rabbit-anti-pIGFR[3 [Cell signaling technology (3024)], rabbit-anti-pS6 [Cell signaling technology (4857)], rat anti-CD68 [Bio-Rad (MCA 1957)], and Guinea pig-anti-Vglut1 [Synaptic Systems (135304)].

Injury Models. The procedure of T10 lateral hemisection was similar to that described elsewhere (Ballermann and Fouad, 2006; Courtine et al., 2008; Takeoka et al., 2014). Briefly, a midline incision was made over the thoracic vertebrae, followed by a T10 laminectomy. The unilateral hemisection was then performed carefully using both scalpel and micro-scissors, avoiding, to the greatest extent, the damage of the spinal cord dura. The muscle layers were then sutured and the skin was secured with wound clips. All mice received post hoc histological analysis and those with spared CST axons (incomplete lateral hemisection) or with significant less CST axons on the contra-lesional side (over lateral hemisection) at the lumbar spinal cord (L3), exemplified in FIG. 9A, were excluded for behavioral analysis.

The procedure of unilateral photothrombotic stroke was similar to that described elsewhere (Watson et al., 1985; Wahl et al., 2014). Briefly, mice were fixed in a stereotactic frame, with the skull exposed. To unilaterally cover the sensoromotor cortex, the cold light source (Zeiss, CL 1500HAL, 3000K) was positioned over an opaque template with an opening (a circle with a diameter of 2.5 mm) centered at (−0.5, 2.0 mm, anterior and lateral to the bregma) on the cortex contralateral to the preferred paw in the food pellet retrieval task. Rose Bengal (10 mg/kg body weight, 5 mg/ml Rose Bengal in saline) was injected (i.p.) 10 min before the brain was illuminated through the intact skull for 15 min. Lesion volumes were calculated when mice brains were fixed at the end point of the experiments.

Virus and Protein Injection. AAV2/1-IGF1, AAV2/1-OPN, AAV2/1-PLAP, AAV2/1-ChR2-YFP, AAV2/1-ChR2-mCherry, AAV2/1-Cre, AAV-2/9-GFP and mCherry (all AAV titers were adjusted to $0.5\text{-}5\times10^{13}$ copies/ml for injection, produced by Boston Children's Hospital, viral core) or recombinant human IGF1 (Peprotech, 1 µg/1 µl) and/or osteopontin (OPN) (Peprotech, 1 µg/1 µl) were injected to the mouse sensorimotor cortex as described previously (Liu et al., 2010, Zukor et al., 2013). Vectors of HiRet-GFP, HiRet-mCherry, HiRet-FLEX-DTR (all lenti-virus titers were adjusted to $1.6\text{-}2\times1012$ copies/ml for injection) were constructed based on the HiRet-lenti backbone (Kinoshita et al., 2012).

Figure 8E:
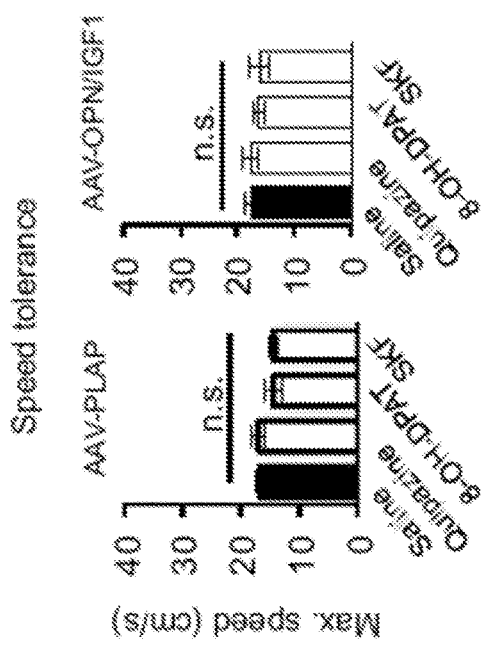
Figure 8F:
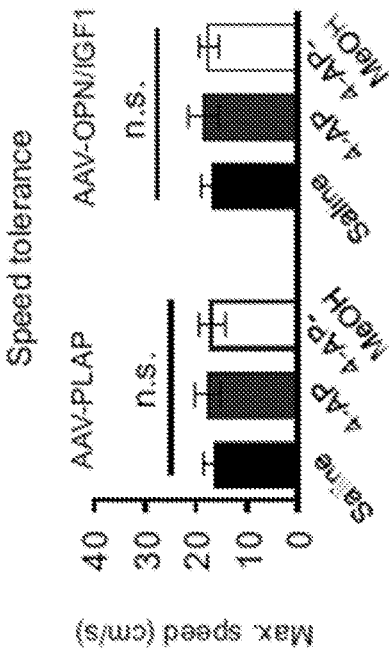

Immunohistochemistry and Imaging. The paraformaldehyde fixed tissues were cryo-protected with 30% sucrose and processed using cryostat (section thickness 40 µm for spinal cord and 60 µm for brain). Sections were treated with a blocking solution containing 10% normal goat serum with 0.5% Triton-100 for 2 hours at room temperature before staining. The primary antibodies (4° C., overnight) used are rabbit anti-GFAP [DAKO (Z0334), 1:1000]; rabbit anti-5-HT [Immunostar (20080), 1:5,000]; chicken anti-GFP [Abcam (ab13970), 1:400]; rabbit anti-RFP [Abcam (ab34771), 1:400]; rabbit anti-PKC7 [Santa Cruz (sc211), 1:100]; rabbit-anti-IGFR [Santa Cruz (sc-712), 1:200] rabbit-anti-pIGFRβ [Cell signaling technology (3024), 1:100], rabbit-anti-pS6 [Cell signaling technology (4857), 1:200], rat anti-CD68 [Bio-Rad (MCA1957), 1:400], and Guinea pig-anti-Vglut1 [Synaptic Systems (135304), 1:1000]. Secondary antibodies (room temperature, 2 h) include Alexa Fluor 488-conjugated goat anti chicken and rabbit, Alexa Fluor 594-conjugated goat anti rabbit (all from Invitrogen). Spinal cord transverse and horizontal sections and brain transverse sections were imaged with a confocal laser-scanning microscope (Zeiss 700 or Zeiss 710). To quantify and compare fluorescence intensity of IGFR, pIGFRβ and pS6 in GFP+ CSNs (FIGS. 2C-2E), CST axons in the dorsal *funiculus* (FIG. 3G) and CD68 staining (FIG. 10F) and corticofugal projections at multiple subcortical areas (FIG. 7B), and axon density of the intact side in the spinal cord (FIGS. 8E and 8F), all images used for analysis under multiple conditions were taken using the same optical parameters and avoided for saturation. Densitometry measurement was taken by using FIJI software, after being sub-thresholded to the background and normalized by area.

Specific Ablation or inhibition of Hindlimb Corticospinal Neurons. To specifically target hindlimb CSNs, 2 µl HiRet viruses (HiRet-GFP/mCherry for labeling HiRet-FLEX-DTR for ablation) were injected to the lower thoracic to lumbar spinal cord (T12-L4) guided by ultrasound (detailed method see Arlotta et al., 2005) and carried out at postnatal day 12-14 (P12-P14) in Emx1-Cre mice. Diphtheria toxin (DT, 100 µg/kg) or tamoxifen (75 mg/kg) was administered (i.p.) in adult animals. The high efficient ablation was verified by the absence of PKCγ staining in the dorsal *funiculus* of the lumbar, but not cervical, spinal cord (FIGS. 1A-1H and 3G) and also with retrograde labeling at lumbar spinal cord (FIGS. 10C and 2E).

Axon Counting and Quantification. To quantify the number of sprouting axons, a horizontal line was firstly drawn through the central canal and across the lateral rim of the gray matter. Three vertical lines (Mid, Z1, and Z2) were drawn to divide the horizontal line into three equal parts, starting from the central canal to the lateral rim. While Mid denotes midline crossing fibers, Z1 and Z2 are for sprouting fibers at different distance from the midline. Only fibers crossing the three lines were counted on each section. The results were presented after normalization with the number of counted CST fibers at the medulla level.

For quantifying total labeled CST axon, AAV-ChR2-YFP (FIG. 4D) or AAV-ChR2-mCherry (FIGS. 4C, 7E and 8E) labeled CST fibers were counted at the level of medulla oblongata 1 mm proximal to the pyramidal decussation. Axons were estimated by counting 4 rectangular areas (about 10000 µm²/area) per section on two adjacent sections.

To quantify the regenerating axons (FIG. 4D), the number of intersections of chR2-YFP-labeled fibers with a dorsal-ventral line positioned at a defined distance caudal from the lesion center was counted under a 25X objective. Fibers were counted on 3 sections with the main dorsal CST and 1-3 lateral sections with collaterals in the gray matter. The number of counted fibers was normalized by the number of labeled CST axons in the medulla and divided by the number of evaluated sections. This resulted in the number of CST fibers per labeled CST axons per section at different distances (fiber number index).

Ground walking, Swimming and Treadmill Walking. For ground walking and swimming, mice were placed in the MotoRater (TSE Systems, Zorner et al., 2010) and all kinematic analysis was performed based on data collected by the MotoRater. For treadmill walking, mice were placed on the DigiGate at various speeds. Speed tolerance was defined as the maximal speed a mouse can walk on the treadmill without falling. All trials were video recorded (Hotshot e64, 100 fps) for the measurement of the paw dragging distance on the treadmill.

Irregular Ladder Walking. In this assay, mice in different groups were tested to walk on a horizontal ladder with irregular spacing between rungs, following the procedure described previously (Metz and Whishaw, 2002; Carmel et al., 2010, 2014; Jin et al., 2015). Briefly, the ladder was elevated 30 cm above the ground. Animals were trained to cross the ladder until their performance achieved the plateau (with an average error rate about 20%). To prevent animals from learning the pattern, the irregular pattern was changed from trial to trial. All trials were video recorded (Hotshot e64, 100 fps) and paw placement was analyzed twice by blinded observers. Steps with precise placement of the center of the palm on the rung (for both forelimbs and hindlimbs) and digits closed (for forelimbs) were defined as correct steps (hit). All other steps were recorded as errors, which included two types: 1) Miss: when crossing the ladder, the forelimb/hindlimb either completely miss the rung or contact the rung with the wrist/heel instead of the paw; 2) Slip: when crossing the ladder, the mice use a few digits instead of the paw to place on the rungs, causing the subsequent slip on the rungs. The results were expressed as both percentage of total errors and percentage of different placement categories (hit, miss and slip).

Single pellet Retrieval. The single-pellet reaching task was carried out following previously established procedures with slight modification (Farr and Whishaw, 2002). The training chamber was built from clear Plexiglas (1 mm thickness, dimensions 20 cm×15 cm×8.5 cm), with a vertical slit (0.5 cm wide; 13 cm high) located on the front wall of the box. An exterior shelf with 1.5 cm height was affixed to the wall in front of the slits to hold a sugar pellet (dustless precision pellet, 20 mg, bioserv). After one day of habituation to the chamber with sugar pellet inside the chamber, mice were food-restricted for one night before training and were maintained above 90% of free feeding weight throughout the training session. Mice were digitally videotaped at 60 frames/sec while reaching for a maximum of 40 pellets within 20 min. The success rate was calculated as: number of successful retrievals/total attempts per trail *100. The animals without intention to retrieve the sugar pellet or consistently using the tongue instead of the forelimb to retrieve the sugar pellet were excluded from receiving the unilateral photothrombotic stroke.

Pharmacological Treatment. Ten to fifteen minutes (van den Brand et al., 2012) prior to behavioral tests (irregular ladder walking, grounding walking or treadmill walking, all of which were performed individually), mice received systematic administration (i.p.) of neural modulators [quipazine (0.2 mg/kg), SKF-82197 (0.1 mg/kg), or 8-OH-DPAT (0.1 mg/kg)]. A pilot experiment was performed and determined that 4AP (1 mg/kg, 3 mg/kg) and 4AP-MeOH (1 mg/kg) achieved their maximal effects within 1-3 hours post systematic administration (i.p.). All behavioral tests were then accomplished between 1-3 hours post administration.

Selective Ablation of CSNs with Sprouted Axons to the Denervated Side of the Spinal Cord. Mice received unilateral photothrombotic stroke at P60, OPN/IGF1 treatment at P63 respectively. Fourteen weeks after injury, a laminectomy was performed at cervical spinal cord. The viruses ($1 \times 10^{12}$ copies/ml) generated by a HiRet-carrying the FLEX-DTR were stereotaxically injected into the denervated side of the cervical (C5-C7) spinal cord of the OPN/IGF1 treated mice with procedures established in Jin et al., 2015. AAV2/1-Cre (ablation) or AAV2/1-PLAP (control) ($1 \times 1013$ copies/ml) was then injected into the unlesioned sensorimotor cortex at 3 days post HiRet virus injection. After 2 weeks, animals were tested for the irregularly spaced horizontal ladder walking and/or single pellet food retrieval task to reassess their performance of the skilled limb movement. Diphtheria toxin was then administered (100 µg/kg, i.p.). Animals were tested for the horizontal ladder walking and/or single pellet food retrieval task again at 2 and 4 weeks after diphtheria toxin administration.

Quantification and statistical analysis. The normality and variance similarity were measured by STATA (version 12, College station, TX, USA) before any parametric tests were applied. Two-tailed Student's t-test was used for the single comparison between two groups. The rest of the data were analyzed using one-way or two-way ANOVA depending on the appropriate design. Post hoc comparisons were carried out only when a main effect showed statistical significance. P-value of multiple comparisons was adjusted by using Bonferroni's correction. Error bars in all figures represent mean±S.E.M. The mice with different litters, body weights and sexes were randomized and assigned to different treatment groups, and no other specific randomization was used for the animal studies.

REFERENCES FOR EXAMPLE 1

Alilain, W. J., Horn, K. P., Hu, H., Dick, T. E., and Silver, J. (2011). Functional regeneration of respiratory pathways after spinal cord injury. Nature 475, 196-200.

Arlotta, P., Molyneaux, B. J., Chen, J., Inoue, J., Kominami, R., and Macklis, J. D. (2005). Neuronal subtype-specific genes that control corticospinal motor neuron development in vivo. Neuron 45, 207-221.

Ayling, O. G., Harrison, T. C., Boyd, J. D., Goroshkov, A., and Murphy, T. H. (2009). Automated light-based mapping of motor cortex by photoactivation of channelrhodopsin-2 transgenic mice. Nat. Methods 6, 219-224.

Ballermann, M., and Fouad, K. (2006). Spontaneous locomotor recovery in spinal cord injured rats is accompanied by anatomical plasticity of reticulospinal fibers. Eur. J. Neurosci. 23, 1988-1996.

Bareyre, F. M., Kerschensteiner, M., Misgeld, T., and Sanes, J. R. (2005). Transgenic labeling of the corticospinal tract for monitoring axonal responses to spinal cord injury. Nat Med. 11, 1355-1360.

Bei, F., Lee, H. H., Liu, X., Gunner, G., Jin, H., Ma, L., Wang, C., Hou, L., Hensch, T. K., Frank, E., et al. (2016). Restoration of visual function by enhancing conduction in regenerated Axons. Cell 164, 219-232.

Blackmore, M. G., Wang, Z., Lerch, J. K., Motti, D., Zhang, Y. P., Shields, C. B., Lee, J. K., Goldberg, J. L., Lemmon, V. P., and Bixby, J. L. (2012). Krüppel-like Factor 7 engineered for transcriptional activation promotes axon regeneration in the adult corticospinal tract. Proc. Natl. Acad. Sci. USA. 109, 7517-7522.

Blight, A. R., Toombs, J. P., Bauer, M. S., and Widmer, W. R. (1991). The effects of 4-aminopyridine on neurological deficits in chronic cases of traumatic spinal cord injury in dogs: a phase I clinical trial. J. Neurotrauma 8, 103-119.

Bostock, H., Sears, T. A., and Sherratt, R. M. (1981). The effects of 4-aminopyridine and tetraethylammonium ions on normal and demyelinated mammalian nerve fibers. J. Physiol. 313, 301-315.

Bradke, F., Fawcett, J. W., and Spira, M. E. (2012). Assembly of a new growth cone after axotomy: the precursor to axon regeneration. Nat. Rev. Neurosci. 13,183-193.

Cai, L. L., Courtine, G., Fong, A. J., Burdick, J. W., Roy, R. R., and Edgerton, V. R. (2006). Plasticity of functional connectivity in the adult spinal cord. Philos. Trans. R. Soc. Lond. B Biol. Sci. 361,1635-1646.

Carmel, J. B., Berrol, L. J., Brus-Ramer, M., and Martin, J. H. (2010). Chronic electrical stimulation of the intact corticospinal system after unilateral injury restores skilled locomotor control and promotes spinal axon outgrowth. J. Neurosci. 30, 10918-10926. Carmel, J. B., Kimura, H., and Martin, J. H. (2014). Electrical stimulation of motor cortex in the uninjured hemisphere after chronic unilateral injury promotes recovery of skilled locomotion through ipsilateral control. J. Neurosci. 34, 462-466.

Carmichael, S. T., Kathirvelu, B., Schweppe, C. A., and Nie, E. H. (2017). Molecular, cellular and functional events in axonal sprouting after stroke. Exp. Neurol. 287, 384-394.

Chen, M., and Zheng, B. (2014). Axon plasticity in the mammalian central nervous system after injury. Trends Neurosci. 37, 583-593.

Courtine, G., Gerasimenko, Y., van den Brand, R., Yew, A., Musienko, P., Zhong, H., Song, B., Ao, Y., Ichiyama, R. M., Lavrov, I., et al. (2009). Transformation of nonfunctional spinal circuits into functional states after the loss of brain input. Nat. Neurosci. 12, 1333-1342.

Courtine, G., Song, B., Roy, R. R., Zhong, H., Herrmann, J. E., Ao, Y., Qi, J., Edgerton, V. R., and Sofroniew, M. V. (2008). Recovery of supraspinal control of stepping via indirect propriospinal relay connections after spinal cord injury. Nat Med. 14, 69-74. Danilov, C. A., and Steward, O. (2015). Conditional genetic deletion of PTEN after a spinal cord injury enhances regenerative growth of CST axons and motor function recovery in mice. Exp. Neurol. 266, 147-160.

Donovan, W. H., Halter, J. A., Graves, D. E., Blight, A. R., Calvillo, O., McCann, M. T., Sherwood, A. M., Castillo, T., Parsons, K. C., and Strayer, J. R. (2000). Intravenous infusion of 4-AP in chronic spinal cord injured subjects. Spinal cord 38, 7-15.

Drew, T. (1993). Motor cortical activity during voluntary gait modifications in the cat. I. Cells related to the forelimbs. J. Neurophysiol. 70, 179-199.

Du, K., Zheng, S., Zhang, Q., Li, S., Gao, X., Wang, J., Jiang, L., and Liu, K. (2015). Pten deletion promotes regrowth of corticospinal tract axons 1 year after spinal cord injury. J. Neurosci. 35, 9754-9763.

Duan X. Qiao, M., Bei, F., Kim, I. J., He, Z., and Sanes, J. R. (2015). Subtype-specific regeneration of retinal ganglion cells following axotomy: effects of osteopontin and mTOR signaling. Neuron 85, 1244-1256.

Farr, T. D., and Whishaw, I. Q. (2002). Quantitative and qualitative impairments in skilled reaching in the mouse (*Mus musculus*) after a focal motor cortex stroke. Stroke 33,1869-1875.

Fong, A. J., Cai, L. L., Otoshi, C. K., Reinkensmeyer, D. J., Burdick, J. W., Roy, R. R., and Edgerton, V. R. (2005). Spinal cord-transected mice learn to step in response to quipazine treatment and robotic training. J Neurosci. 25, 11738-11747.

Fouad, K., Pedersen, V., Schwab, M. E., and Brösamle, C. (2001). Cervical sprouting of corticospinal fibers after thoracic spinal cord injury accompanies shifts in evoked motor responses. Curr. Biol. 11, 1766-1770.

Garcia-Alias, G., Barkhuysen, S., Buckle, M., and Fawcett, J. W. (2009). Chondroitinase ABC treatment opens a window of opportunity for task-specific rehabilitation. Nat. Neurosci. 12, 1145-1151.

Garcia-Alias, G., Truong, K., Shah, P. K., Roy, R. R., and Edgerton, V. R. (2015). Plasticity of subcortical pathways promote recovery of skilled hand function in rats after corticospinal and rubrospinal tract injuries. Exp. Neurol. 266, 112-119.

Geoffroy, C. G., Lorenzana, A. O., Kwan, J. P., Lin, K., Ghassemi, O., Ma, A., Xu, N., Creger, D., Liu, K., He, Z., et al. (2015). Effects of PTEN and Nogo codeletion on corticospinal axon sprouting and regeneration in mice. J.

Neurosci. 35, 6413-6428. Georgopoulos, A. P. and Grillner, S. (1989). Visuomotor coordination in reaching and locomotion. Science 245, 1209-1210.

Giehl, K. M., and Tetzlaff, W. (1996). BDNF and NT-3, but not NGF, prevent axotomy-induced death of rat corticospinal neurons in vivo. Eur. J. Neurosci. 6,1167-1175.

He, Z., and Jin, Y. (2016). Intrinsic control of axon regeneration. Neuron 90, 437-451. Hernández-Sánchez, C., Blakesley, V., Kalebic, T., Helman, L., and LeRoith, D. (1995). The role of the tyrosine kinase domain of the insulin-like growth factor-1 receptor in intracellular signaling, cellular proliferation, and tumorigenesis. J. Biol. Chem. 270, 29176-29181.

Hollis, E. R. 2nd, Lu, P., Blesch, A., and Tuszynski, M. H. (2009). IGF-I gene delivery promotes corticospinal neuronal survival but not regeneration after adult CNS injury. Exp. Neurol. 215, 53-59.

Jin, D., Liu, Y., Sun, F., Wang, X., Liu, X., and He, Z. (2015). Restoration of skilled locomotion by sprouting corticospinal axons induced by co-deletion of PTEN and SOCS3. Nat Commun. 6, 8074.

Kahles, F., Findeisen, H. M., and Bruemmer, D. (2014). Osteopontin: A novel regulator at the cross roads of inflammation, obesity and diabetes. Mol. Metab. 3, 384-393.

Kazanecki, C. C., Uzwiak, D. J., and Denhardt, D. T. (2007). Control of osteopontin signaling and function by post-translational phosphorylation and protein folding. J. Cell Biochem. 102, 912-924.

Kinoshita, M., Matsui, R., Kato, S., Hasegawa, T., Kasahara, H., Isa, K., Watakabe, A., Yamamori. T., Nishimura, Y., Alstermark, B., et al. (2012). Genetic dissection of the circuit for hand dexterity in primates. Nature 487, 235-238.

Lang, C., Bradley, P. M., Jacobi, A., Kerschensteiner, M., and Bareyre, F. M. (2013). STAT3 promotes corticospinal remodelling and functional recovery after spinal cord injury. EMBO Rep. 14, 931-937.

Lewandowski, G., and Steward, O. (2014). AAVshRNA-mediated suppression of PTEN in adult rats in combination with salmon fibrin administration enables regenerative growth of corticospinal axons and enhances recovery of voluntary motor function after cervical spinal cord injury. J. Neurosci. 34, 9951-9962.

Li, S., Overman, J. J., Katsman, D., Kozlov, S. V., Donnelly, C. J., Twiss, J. L., Giger, R. J., Coppola, G., Geschwind, D. H, and Carmichael, S. T. (2010). An age-related sprouting transcriptome provides molecular control of axonal sprouting after stroke. Nat. Neurosci. 13, 1496-1504.

Li, S., Nie, E. H., Yin, Y., Benowitz, L. I., Tung, S., Vinters, H. V., Bahjat, F. R., Stenzel-Poore, M. P., Kawaguchi, R., Coppola, G., et al. (2015). GDF10 is a signal for axonal sprouting and functional recovery after stroke. Nat. Neurosci. 18, 1737-1745.

Liddell, E. G. T., and Phillips, C. G. (1944). Pyramidal section in cat. Brain 67, 1-9.

Liu, K., Lu, Y., Lee, J. K., Samara, R., Willenberg, R., Sears-Kraxberger, I., Tedeschi, A., Park, K. K., Jin, D., Cai, B., et al. (2010). PTEN deletion enhances the regenerative ability of adult corticospinal neurons. Nat Neurosci 13, 1075-1081.

Lu, P., Blesch, A., and Tuszynski, M. H. (2001). Neurotrophism without neurotropism: BDNF promotes survival but not growth of lesioned corticospinal neurons. J. Comp. Neurol. 436,456-470.

Maier, I. C., Baumann, K., Thallmair, M., Weinmann, O., Scholl, J., and Schwab, M. E. (2008). Constraint-induced movement therapy in the adult rat after unilateral corticospinal tract injury. J. Neurosci. 28, 9386-9403.

Maier, I. C., and Schwab, M. E. (2006). Sprouting, regeneration and circuit formation in the injured spinal cord: factors and activity. Philos. Trans. R. Soc. Lond. B Biol. Sci. 361, 1611-1634.

Metz, G. A., Dietz, V., Schwab, M. E., and van de Meent, H. (1998). The effects of unilateral pyramidal tract section on hindlimb motor performance in the rat. Behav. Brain Res. 96, 37-46.

Metz, G. A., and Whishaw, I. Q. (2002). Cortical and subcortical lesions impair skilled walking in the ladder rung walking test: a new task to evaluate fore- and hindlimb stepping, placing, and co-ordination. J. Neurosci. Methods 115, 169-179.

Muir, G. D., and Whishaw, I. Q. (1999). Complete locomotor recovery following corticospinal tract lesions: measurement of ground reaction forces during overground locomotion in rats. Behav. Brain Res. 103, 45-53.

Murray, K. C., Nakae, A., Stephens, M. J., Rank, M., D'Amico, J., Harvey, P. J., Li, X., Harris, R. L., Ballou, E. W., Anelli, R., et al. (2010). Recovery of motoneuron and locomotor function after spinal cord injury depends on constitutive activity in 5-HT2C receptors. Nat. Med. 16, 694-700.

Musienko, P., van den Brand, R., Märzendorfer, O., Roy, R. R., Gerasimenko, Y., Edgerton, V. R., and Courtine, G. (2011). Controlling specific locomotor behaviors through multidimensional monoaminergic modulation of spinal circuitries. J. Neurosci. 31, 9264-9278.

O'Leary, D. D. (1992). Development of connectional diversity and specificity in the mammalian brain by the pruning of collateral projections. Curr. Opin. Neurobiol. 2, 70-77.

O'Leary, D. D., and Koester, S. E. (1993). Development of projection neuron types, axon pathways, and patterned connections of the mammalian cortex. Neuron 10, 991-1006. Ozdinler, P. H., and Macklis, J. D. (2006). IGF-I specifically enhances axon outgrowth of corticospinal motor neurons. Nat. Neurosci. 11, 1371-1381.

Pollak, M. (2008). Insulin and insulin-like growth factor signalling in neoplasia. Nat. Rev. Cancer 8, 915-928.

Raineteau, O., and Schwab, M. E. (2001). Plasticity of motor systems after incomplete spinal cord injury. Nat. Rev. Neurosci. 2, 263-273.

Ratan, R. R., and Noble, M. (2009). Novel multi-modal strategies to promote brain and spinal cord injury recovery. Stroke 40, S130-132.

Rossignol, S., Martinez, M., Escalona, M., Kundu, A., Delivet-Mongrain, H., Alluin, O., and Gossard, J. P. (2015). The "beneficial" effects of locomotor training after various types of spinal lesions in cats and rats. Prog. Brain Res. 218, 173-198.

Ruschel, J., Hellal, F., Flynn, K. C., Dupraz, S., Elliott, D. A., Tedeschi, A., Bates, M., Sliwinski, C., Brook, G., Dobrindt, K., et al. (2015). Axonal regeneration. Systemic administration of epothilone B promotes axon regeneration after spinal cord injury. Science 348, 347-352.

Salani, B., Briatore, L., Contini, P., Passalacqua, M., Melloni, E., Paggi, A., Cordera, R., and Maggi, D. (2009). IGF-I induced rapid recruitment of integrin beta1 to lipid rafts is Caveolin-1 dependent. Biochem. Biophys. Res. Commun. 380,489-492.

Siddle, K. (2012). Molecular basis of signaling specificity of insulin and IGF receptors: neglected corners and recent advances. Front Endocrinol. (Lausanne). 3, 34.

Sun, W., Smith, D., Fu, Y., Cheng, J. X., Bryn, S., Borgens, R., and Shi, R. (2010). Novel potassium channel blocker, 4-AP-3-MeOH, inhibits fast potassium channels and restores axonal conduction in injured guinea pig spinal cord white matter. J. Neurophysiol. 103, 469-478.

Takeoka, A., Vollenweider, I., Courtine, G., and Arber, S. (2014). Muscle spindle feedback directs locomotor recovery and circuit reorganization after spinal cord injury. Cell 159, 1626-1639.

Tennant. K. A., Adkins, D. L., Donlan, NA., Asay, A. L., Thomas, N., Kleim, J. A., and Jones, T. A. (2011). The organization of the forelimb representation of the C57BL/6 mouse motor cortex as defined by intracortical microstimulation and cytoarchitecture. Cereb. Cortex 21, 865-876.

Tetzlaff, W., Kobayashi, N. R., Giehl, K. M., Tsui, B. J., Cassar, S. L., and Bedard, A. M. (1994). Response of rubrospinal and corticospinal neurons to injury and neurotrophins. Prog. Brain Res. 103, 271-286.

Thoenen, H., and Sendtner, M. (2002). Neurotrophins: from enthusiastic expectations through sobering experiences to rational therapeutic approaches. Nat. Neurosci. 5, Suppl: 1046-1050.

Tuszynski, M. H. and Steward, O. (2012). Concepts and methods for the study of axonal regeneration in the CNS. Neuron 74, 777-791.

van den Brand, R., Heutschi, J., Barraud, Q., DiGiovanna, J., Bartholdi, K., Huerlimann, M., Friedli, L., Vollenweider, I., Moraud, E. M., Duis, S., et al. (2012). Restoring voluntary control of locomotion after paralyzing spinal cord injury. Science 336, 1182-1185.

Wahl, A. S., Omlor, W., Rubio, J. C., Chen, J. L., Zheng, H., Schröter, A., Gullo, M., Weinmann, O., Kobayashi, K., Helmchen, F., et al. (2014). Neuronal repair. Asynchronous therapy restores motor control by rewiring of the rat corticospinal tract after stroke. Science 344, 1250-1255.

Wang, K. X., and Denhardt, D. T. (2008). Osteopontin: role in immune regulation and stress responses. Cytokine Growth Factor Rev. 19, 333-345.

Wang, Z., Reynolds, A., Kirry, A., Nienhaus, C., and Blackmore, M. G. (2015). Overexpression of Sox11 promotes corticospinal tract regeneration after spinal injury while interfering with functional recovery. J. Neurosci. 35, 3139-3145.

Watson, B. D., Dietrich, W. D., Busto, R., Wachtel, M. S., and Ginsberg, M. D. (1985). Induction of reproducible brain infarction by photochemically initiated thrombosis. Ann. Neurol. 17,497-504.

Weidner, N., Ner, A., Salimi, N., and Tuszynski, M. H. (2001). Spontaneous corticospinal axonal plasticity and functional recovery after adult central nervous system injury. Proc. Natl. Acad. Sci. USA. 98, 3513-3518.

Zömer, B., Filli, L., Starkey, M. L., Gonzenbach, R, Kasper, H., Röthlisberger, M., Bolliger, M., and Schwab, M. E. (2010). Profiling locomotor recovery: comprehensive quantification of impairments after CNS damage in rodents. Nat. Methods 7, 701-708. Zukor, K., Belin, S., Wang, C., Keelan, N., Wang, X., and He, Z. (2013). Short hairpin RNA against PTEN enhances regenerative growth of corticospinal tract axons after spinal cord injury. J. Neurosci. 33, 15350-15361.

Example 2

The effects of various forms of active OPN were assessed for their capacity to promote optic nerve axon regeneration in an induced injury model. To express the various forms of active OPN AAVs expressing all forms of mouse OPN were injected intravitreally in anesthetized mice. To induce the injury model the optic nerves were crushed using a pair of forceps two weeks after intravitreal injection. Recombinant proteins (CNTF, IGF1, BDNF) were injected at 0 and 7 days after the crush (1 ul each, 1 ug/ul). Fluorescent cholera toxin beta subunit (CTB-555) was injected intravitreally 12 days after crush to trace the axons before the tissues were fixed 14 days after crush, sectioned and imaged.

Figure 18:
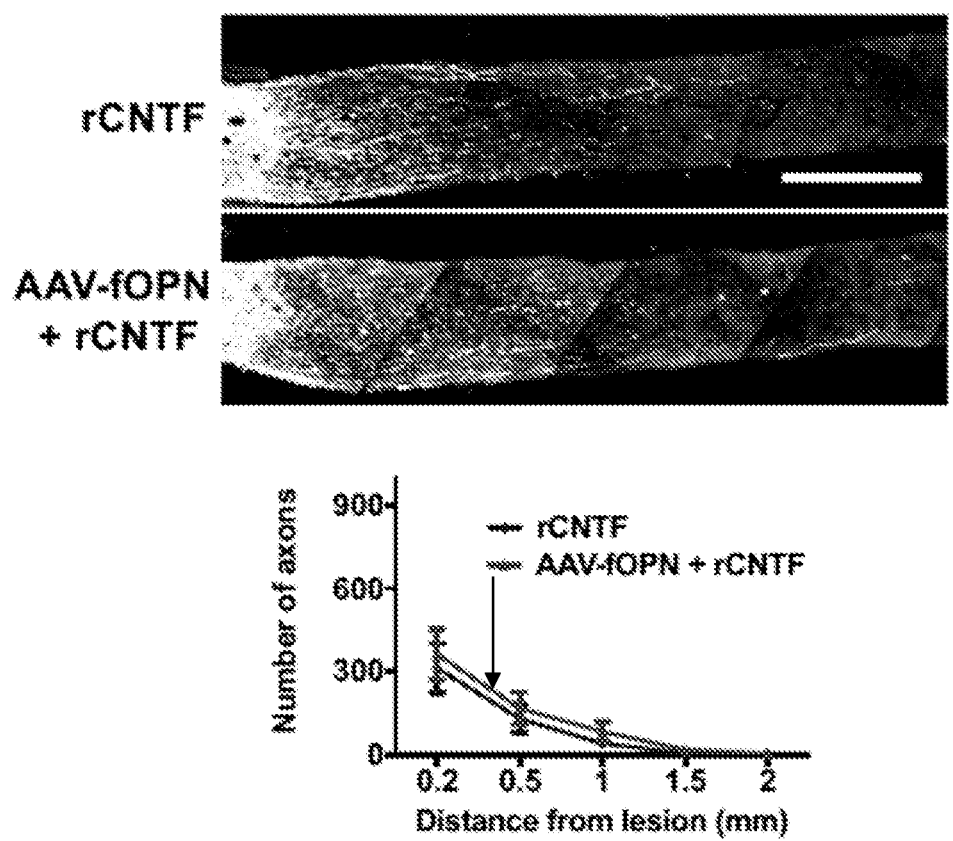
FIG. 18 presents experimental results that indicate no added effect of OPN to CNTF in promoting optic nerve axon regeneration. Scale bars, 0.3 mm. * p<0.05, p<0.01, * p<0.001, ANOVA.
Figure 20:
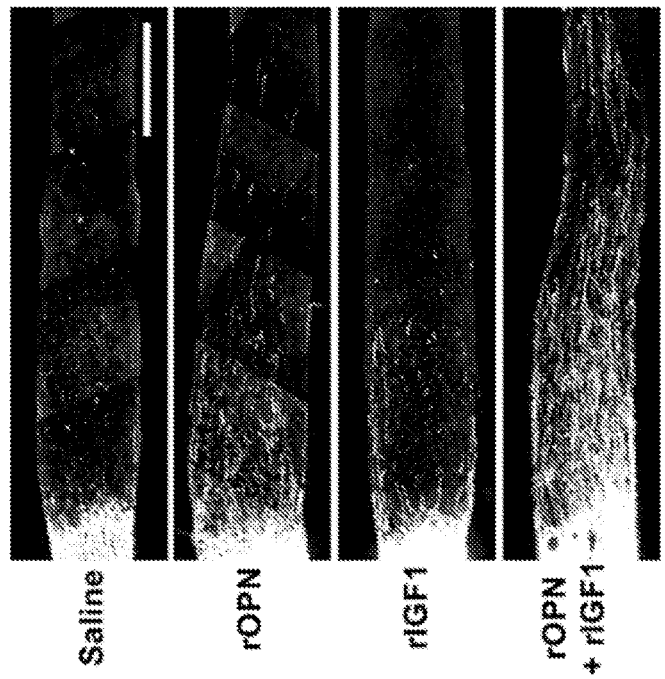
FIG. 20 presents experimental results that indicate intravitreal application of recombinant OPN protein is also pro-regenerative when combined with IGF1. Scale bars, 0.3 mm. * p<0.05, p<0.01. * p<0.001. ANOVA.
Figure 20:
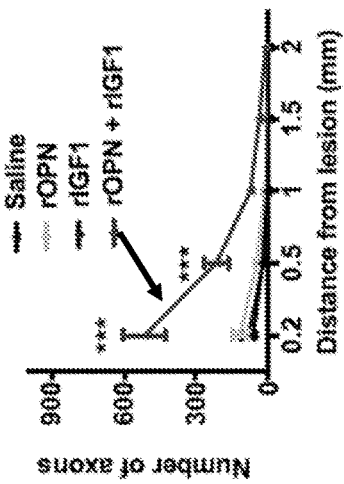
Figure 19:
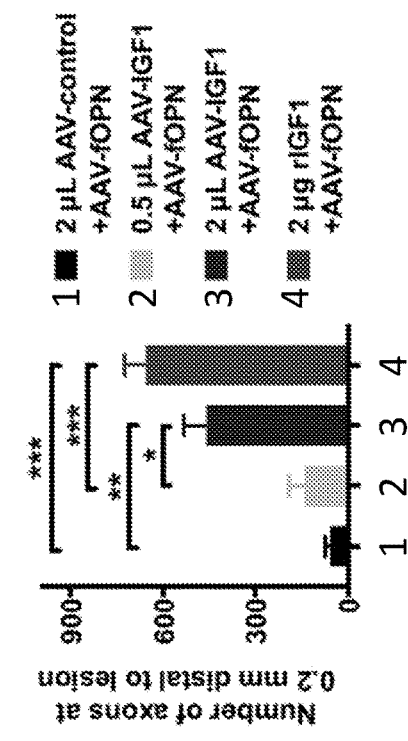
FIG. 19 presents experimental results that indicate dose-dependence of AAV-IGF1 in its pro-regenerative effect with OPN. Scale bars, 0.3 mm. * p<0.05, p<0.01. * p<0.00). ANOVA.

Significant optic nerve regeneration was observed following intravitreal injection of full length OPN (AAV-fOPN) combined with recombinant IGF1 (rIGF1), or AAV-fOPN combined with recombinant BDNF (rBDNF) (FIGS. 17A-17D, 17G, and 17H). In contrast, the addition of recombinant CNTF has no effect on optic nerve regeneration (FIG. 18). The regenerative effect of rIGF1 was dosage dependent; a higher level of rIGF1 resulted in a greater capacity for the optic nerve to regenerate. Moreover, recombinant OPN (rOPN) displayed pro-regenerative effects on the optic nerve in the induced injury model (FIG. 20).

Figure 21:
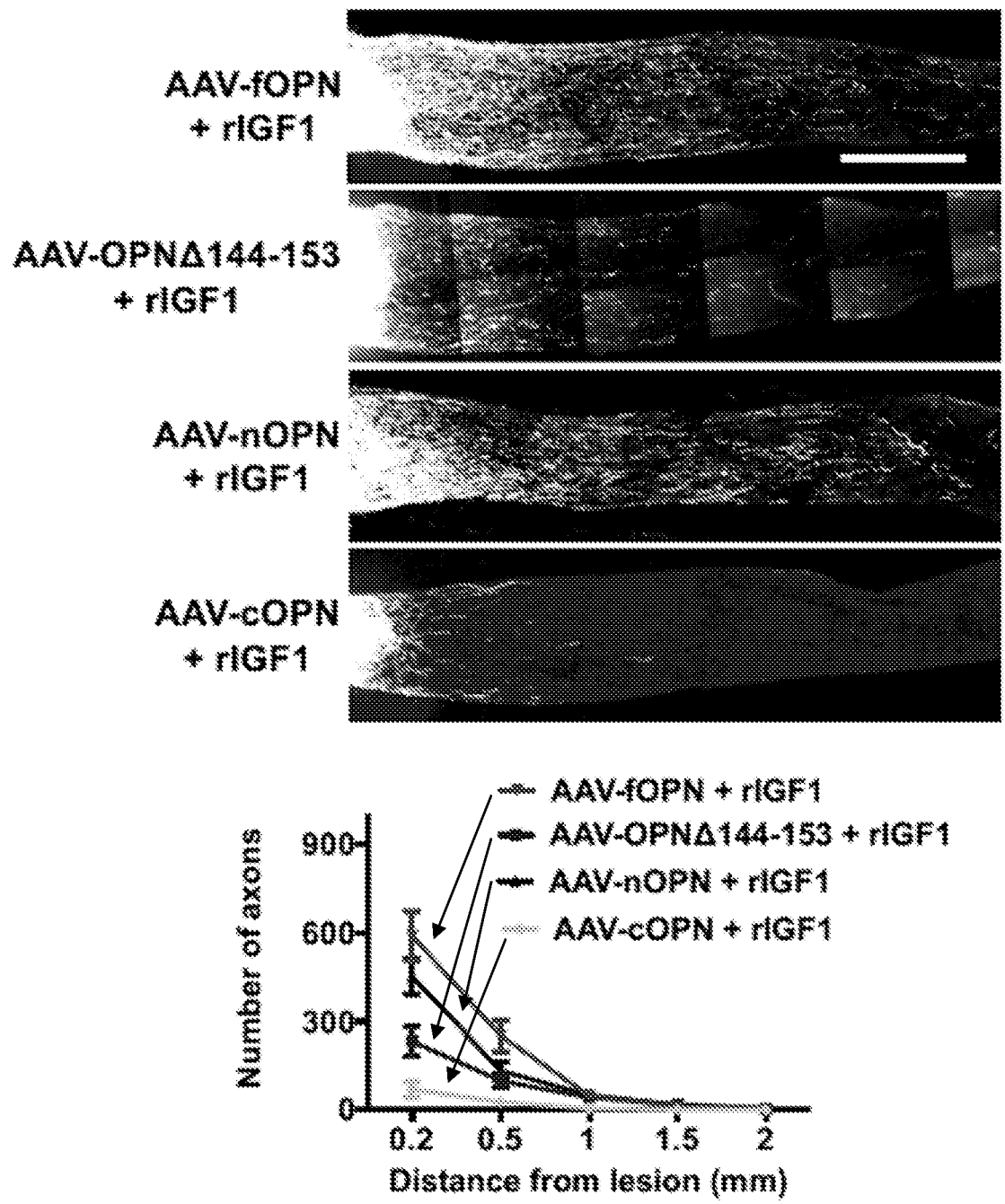
FIG. 21 presents experimental results that indicate N-terminal fragment of OPN (amino acids 1-204) is pro-regenerative while the C-terminal fragment is not. Deleting amino acid 144-153 in OPN significantly reduces its regenerative ability. Scale bars, 0.3 mm. * p<0.05, p<0.01, * p<0.001, ANOVA.

To determine the region of OPN that contains the regenerative capacity, a construct was generated that had the C-terminus of OPN deleted, leaving the N-terminal fragment 1-204 a.a. expressed (nOPN). In addition, an OPN construct was generated that deleted amino acids 144-153 (OPN Δ144-154). Further, a construct containing the C-terminal fragment of OPN (amino acids 205-294) was generated. The capacity to regenerate the optic nerve of these constructs were compared to full length OPN (fOPN) in the induced injury model. Regeneration was seen with fOPN and with the N-terminal 1-204 fragment, but was not seen with administration of the C-terminal fragment or the OPN Δ144-154(FIG. 21). This indicates that the N-terminal fragment of OPN (amino acids 1-204) is pro-regenerative while the C-terminal fragment and constructs of OPN lacking 144-154 are not. Deleting amino acid 144-153 in OPN eliminates its regenerative ability in this assay.

The invention claimed is:

1. A method of promoting corticospinal neuronal outgrowth in a subject having a neuronal lesion, the method comprising administering to the subject an effective amount of a pro-regenerative human osteopontin (OPN) fragment consisting of amino acids 1-219 of SEQ ID NO: 4 in combination with an effective amount of one or both of insulin-like growth factor 1 (IGF1) and brain-derived neurotrophic factor (BDNF), to thereby contact the neuronal lesion and induce corticospinal neuronal outgrowth in the subject, wherein the neuronal lesion is a result of a spinal cord injury, traumatic brain injury or stroke.

2. The method of claim 1 further comprising administering to the subject an effective amount of a voltage gated potassium channel blocker.

3. The method of claim 2, wherein the voltage gated potassium channel blocker is 4-aminopyridine (4-AP) or 4-aminopyridine-3-methanol (4-AP-MeOH).

4. The method of claim 1, wherein the subject is an adult.

5. The method of claim 1, wherein administering results in slow release of the pro-regenerative OPN fragment.

6. The method of claim 1, wherein administering begins within 24 hours of the time of lesion development.

7. The method of claim 1, wherein administering is periodic.

8. The method of claim 1 wherein administering is over a period of at least 8 weeks, or over a period of at least 12 weeks.

9. The method of claim 1, wherein administering is localized.

10. The method of claim 1, wherein administering is directly to the injury site.

11. The method of claim 1, wherein administering is systemic.

* * * * *

SEQUENCE LISTING

```
<160> NUMBER OF SEQ ID NOS: 10

<210> SEQ ID NO 1
<211> LENGTH: 294
<212> TYPE: PRT
<213> ORGANISM: Mus musculus

<400> SEQUENCE: 1

Met Arg Leu Ala Val Ile Cys Phe Cys Leu Phe Gly Ile Ala Ser Ser
1               5                   10                  15
```

```
Leu Pro Val Lys Val Thr Asp Ser Gly Ser Ser Glu Glu Lys Leu Tyr
            20                  25                  30

Ser Leu His Pro Asp Pro Ile Ala Thr Trp Leu Val Pro Asp Pro Ser
        35                  40                  45

Gln Lys Gln Asn Leu Leu Ala Pro Gln Asn Ala Val Ser Ser Glu Glu
    50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Gly Asp
                85                  90                  95

His Ala Glu Ser Glu Asp Ser Val Asp Ser Asp Glu Ser Asp Glu Ser
            100                 105                 110

His His Ser Asp Glu Ser Asp Glu Thr Val Thr Ala Ser Thr Gln Ala
        115                 120                 125

Asp Thr Phe Thr Pro Ile Val Pro Thr Val Asp Val Pro Asn Gly Arg
    130                 135                 140

Gly Asp Ser Leu Ala Tyr Gly Leu Arg Ser Lys Ser Arg Ser Phe Gln
145                 150                 155                 160

Val Ser Asp Glu Gln Tyr Pro Asp Ala Thr Asp Glu Asp Leu Thr Ser
            165                 170                 175

His Met Lys Ser Gly Glu Ser Lys Glu Ser Leu Asp Val Ile Pro Val
        180                 185                 190

Ala Gln Leu Leu Ser Met Pro Ser Asp Gln Asp Asn Asn Gly Lys Gly
    195                 200                 205

Ser His Glu Ser Ser Gln Leu Asp Glu Pro Ser Leu Glu Thr His Arg
210                 215                 220

Leu Glu His Ser Lys Glu Ser Gln Glu Ser Ala Asp Gln Ser Asp Val
225                 230                 235                 240

Ile Asp Ser Gln Ala Ser Ser Lys Ala Ser Leu Glu His Gln Ser His
            245                 250                 255

Lys Phe His Ser His Lys Asp Lys Leu Val Leu Asp Pro Lys Ser Lys
        260                 265                 270

Glu Asp Asp Arg Tyr Leu Lys Phe Arg Ile Ser His Glu Leu Glu Ser
    275                 280                 285

Ser Ser Ser Glu Val Asn
    290

<210> SEQ ID NO 2
<211> LENGTH: 314
<212> TYPE: PRT
<213> ORGANISM: Homo sapiens

<400> SEQUENCE: 2

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
            85                  90                  95
```

Val Asp Ser Gln Asp Ser Ile Asp Ser Asn Asp Ser Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 3
<211> LENGTH: 204
<212> TYPE: PRT
<213> ORGANISM: Mus musculus

<400> SEQUENCE: 3

Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
            20                  25                  30

Ser Leu His Pro Asp Pro Ile Ala Thr Trp Leu Val Pro Asp Pro Ser
        35                  40                  45

Gln Lys Gln Asn Leu Leu Ala Pro Gln Asn Ala Val Ser Ser Glu Glu
    50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Gly Asp
                85                  90                  95

His Ala Glu Ser Glu Asp Ser Val Asp Ser Asp Glu Ser Asp Glu Ser
            100                 105                 110

His His Ser Asp Glu Ser Asp Glu Thr Val Thr Ala Ser Thr Gln Ala
        115                 120                 125

Asp Thr Phe Thr Pro Ile Val Pro Thr Val Asp Val Pro Asn Gly Arg
    130                 135                 140

Gly Asp Ser Leu Ala Tyr Gly Leu Arg Ser Lys Ser Arg Ser Phe Gln

```
         145                 150                 155                 160
Val Ser Asp Glu Gln Tyr Pro Asp Ala Thr Asp Glu Asp Leu Thr Ser
                    165                 170                 175

His Met Lys Ser Gly Glu Ser Lys Glu Ser Leu Asp Val Ile Pro Val
            180                 185                 190

Ala Gln Leu Leu Ser Met Pro Ser Asp Gln Asp Asn
        195                 200

<210> SEQ ID NO 4
<211> LENGTH: 219
<212> TYPE: PRT
<213> ORGANISM: Homo sapiens

<400> SEQUENCE: 4

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser
    210                 215

<210> SEQ ID NO 5
<211> LENGTH: 188
<212> TYPE: PRT
<213> ORGANISM: Mus musculus

<400> SEQUENCE: 5

Leu Pro Val Lys Val Thr Asp Ser Gly Ser Ser Glu Glu Lys Leu Tyr
1               5                   10                  15

Ser Leu His Pro Asp Pro Ile Ala Thr Trp Leu Val Pro Asp Pro Ser
            20                  25                  30

Gln Lys Gln Asn Leu Leu Ala Pro Gln Asn Ala Val Ser Ser Glu Glu
        35                  40                  45

Lys Asp Asp Phe Lys Gln Glu Thr Leu Pro Ser Asn Ser Asn Glu Ser
```

50                  55                  60

His Asp His Met Asp Asp Asp Asp Asp Asp Asp Gly Asp
 65                  70                  75                  80

His Ala Glu Ser Glu Asp Ser Val Asp Ser Asp Glu Ser
                 85                  90                  95

His His Ser Asp Glu Ser Asp Glu Thr Val Thr Ala Ser Thr Gln Ala
                    100                 105                 110

Asp Thr Phe Thr Pro Ile Val Pro Thr Val Asp Val Pro Asn Gly Arg
            115                 120                 125

Gly Asp Ser Leu Ala Tyr Gly Leu Arg Ser Lys Ser Arg Ser Phe Gln
    130                 135                 140

Val Ser Asp Glu Gln Tyr Pro Asp Ala Thr Asp Glu Asp Leu Thr Ser
145                 150                 155                 160

His Met Lys Ser Gly Glu Ser Lys Glu Ser Leu Asp Val Ile Pro Val
                165                 170                 175

Ala Gln Leu Leu Ser Met Pro Ser Asp Gln Asp Asn
            180                 185

<210> SEQ ID NO 6
<211> LENGTH: 203
<212> TYPE: PRT
<213> ORGANISM: Homo sapiens

<400> SEQUENCE: 6

Ile Pro Val Lys Gln Ala Asp Ser Gly Ser Ser Glu Glu Lys Gln Leu
 1               5                  10                  15

Tyr Asn Lys Tyr Pro Asp Ala Val Ala Thr Trp Leu Asn Pro Asp Pro
                20                  25                  30

Ser Gln Lys Gln Asn Leu Leu Ala Pro Gln Asn Ala Val Ser Ser Glu
            35                  40                  45

Glu Thr Asn Asp Phe Lys Gln Glu Thr Leu Pro Ser Lys Ser Asn Glu
        50                  55                  60

Ser His Asp His Met Asp Asp Met Asp Asp Glu Asp Asp Asp Asp His
 65                  70                  75                  80

Val Asp Ser Gln Asp Ser Ile Asp Ser Asn Asp Ser Asp Asp Val Asp
                 85                  90                  95

Asp Thr Asp Asp Ser His Gln Ser Asp Glu Ser His His Ser Asp Glu
                    100                 105                 110

Ser Asp Glu Leu Val Thr Asp Phe Pro Thr Asp Leu Pro Ala Thr Glu
            115                 120                 125

Val Phe Thr Pro Val Val Pro Thr Val Asp Thr Tyr Asp Gly Arg Gly
    130                 135                 140

Asp Ser Val Val Tyr Gly Leu Arg Ser Lys Ser Lys Lys Phe Arg Arg
145                 150                 155                 160

Pro Asp Ile Gln Tyr Pro Asp Ala Thr Asp Glu Asp Ile Thr Ser His
                165                 170                 175

Met Glu Ser Glu Glu Leu Asn Gly Ala Tyr Lys Ala Ile Pro Val Ala
                180                 185                 190

Gln Asp Leu Asn Ala Pro Ser Asp Trp Asp Ser
            195                 200

<210> SEQ ID NO 7
<211> LENGTH: 925
<212> TYPE: DNA
<213> ORGANISM: Homo sapiens

<400> SEQUENCE: 7

```
atgagaattg cagtgatttg cttttgcctc ctaggcatca cctgtgccat accagttaaa    60
caggctgatt ctggaagttc tgaggaaaag cagctttaca caaatacccc agatgctgtg   120
gccacatggc taaaccctga cccatctcag aagcagaatc tcctagcccc acagaatgct   180
gtgtcctctg aagaaaccaa tgactttaaa caagagaccc ttccaagtaa gtccaacgaa   240
agccatgacc acatggatga tatggatgat gaagatgatg atgaccatgt ggacagccag   300
gactccattg actcgaacga ctctgatgat gtagatgaca ctgatgattc tcaccagtct   360
gatgagtctc accattctga tgaatctgat gaactggtca ctgattttcc cacggacctg   420
ccagcaaccg aagttttgtc cccacagtag acacatatga tggccgaggt gatagtgtgg   480
tttatggact gaggtcaaaa tctaagaagt ttcgcagacc tgacatccag taccctgatg   540
ctacagacga ggacatcacc tcacacatgg aaagcgagga gttgaatggt gcatacaagg   600
ccatccccgt tgcccaggac ctgaacgcgc cttctgattg ggacagccgt gggaaggaca   660
gttatagctg gatgaccaga gtgctgaaac ccacagccac aagcagtcca gattatataa   720
gcggaaagcc aatgatgaga gcaatgagca ttccgatgtg attgatagtc aggaactttc   780
caaagtcagc cgtgaattcc acagccatga atttcacagc catgaagata tgctggttgt   840
agaccccaaa agtaaggaag aagataaaca cctgaaattt cgtatttctc atgaattaga   900
tagtgcatct tctgaggtca attaa                                          925
```

<210> SEQ ID NO 8
<211> LENGTH: 885
<212> TYPE: DNA
<213> ORGANISM: Mus musculus

<400> SEQUENCE: 8

```
atgagattgg cagtgatttg cttttgcctg tttggcattg cctcctccct cccggtgaaa    60
gtgactgatt ctggcagctc agaggagaag ctttacagcc tgcacccaga tcctatagcc   120
acatggctgg tgcctgaccc atctcagaag cagaatctcc ttgcgccaca gaatgctgtg   180
tcctctgaag aaaaggatga ctttaagcaa gaaactcttc caagcaattc caatgaaagc   240
catgaccaca tggacgacga tgatgacgat gatgatgacg atggagacca tgcagagagc   300
gaggattctg tggactcgga tgaatctgac gaatctcacc attcggatga gtctgatgag   360
accgtcactg ctagtacaca agcagacact ttcactccaa tcgtccctac agtcgatgtc   420
cccaacggcc gaggtgatag cttggcttat ggactgaggt caaagtctag gagtttccag   480
gtttctgatg aacagtatcc tgatgccaca gatgaggacc tcacctctca catgaagagc   540
ggtgagtcta aggagtccct cgatgtcatc cctgttgccc agcttctgag catgccctct   600
gatcaggaca acaacggaaa gggcagccat gagtcaagtc agctggatga ccaagtctg    660
gaaacacaca gacttgagca ttccaaagag agccaggaga gtgccgatca gtcggatgtg   720
atcgatagtc aagcaagttc caaagccagc ctggaacatc agagccacaa gtttcacagc   780
cacaaggaca agctagtcct agaccctaag agtaaggaag atgataggta tctgaaattc   840
cgaatttctc atgaattaga gagttcatct tctgaggtca actaa                    885
```

<210> SEQ ID NO 9
<211> LENGTH: 294
<212> TYPE: PRT
<213> ORGANISM: Mus musculus

<400> SEQUENCE: 9

```
Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
            20                  25                  30

Ser Leu His Pro Asp Pro Ile Ala Thr Trp Leu Val Pro Asp Pro Ser
        35                  40                  45

Gln Lys Gln Asn Leu Leu Ala Pro Gln Asn Ala Val Ser Ser Glu Glu
    50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Asp Gly Asp
                85                  90                  95

His Ala Glu Ser Glu Asp Ser Val Asp Ser Asp Glu Ser Asp Glu Ser
            100                 105                 110

His His Ser Asp Glu Ser Asp Glu Thr Val Thr Ala Ser Thr Gln Ala
        115                 120                 125

Asp Thr Phe Thr Pro Ile Val Pro Thr Val Asp Val Pro Asn Gly Arg
    130                 135                 140

Gly Asp Ser Leu Ala Tyr Gly Leu Arg Ser Lys Ser Arg Ser Phe Gln
145                 150                 155                 160

Val Ser Asp Glu Gln Tyr Pro Asp Ala Thr Asp Glu Asp Leu Thr Ser
                165                 170                 175

His Met Lys Ser Gly Glu Ser Lys Glu Ser Leu Asp Val Ile Pro Val
            180                 185                 190

Ala Gln Leu Leu Ser Met Pro Ser Asp Gln Asp Asn Asn Gly Lys Gly
        195                 200                 205

Ser His Glu Ser Ser Gln Leu Asp Glu Pro Ser Leu Glu Thr His Arg
    210                 215                 220

Leu Glu His Ser Lys Glu Ser Gln Glu Ser Ala Asp Gln Ser Asp Val
225                 230                 235                 240

Ile Asp Ser Gln Ala Ser Ser Lys Ala Ser Leu Glu His Gln Ser His
                245                 250                 255

Lys Phe His Ser His Lys Asp Lys Leu Val Leu Asp Pro Lys Ser Lys
            260                 265                 270

Glu Asp Asp Arg Tyr Leu Lys Phe Arg Ile Ser His Glu Leu Glu Ser
        275                 280                 285

Ser Ser Ser Glu Val Asn
    290

<210> SEQ ID NO 10
<211> LENGTH: 314
<212> TYPE: PRT
<213> ORGANISM: Homo sapiens

<400> SEQUENCE: 10

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
```

-continued

```
              65                  70                  75                  80
Ser His Asp His Met Asp Asp Met Asp Glu Asp Asp Asp His
                 85                  90                  95
Val Asp Ser Gln Asp Ser Ile Asp Ser Asn Asp Ser Asp Asp Val Asp
                 100                 105                 110
Asp Thr Asp Asp Ser His Gln Ser Asp Glu Ser His His Ser Asp Glu
                 115                 120                 125
Ser Asp Glu Leu Val Thr Asp Phe Pro Thr Asp Leu Pro Ala Thr Glu
             130                 135                 140
Val Phe Thr Pro Val Val Pro Thr Val Asp Thr Tyr Asp Gly Arg Gly
145                 150                 155                 160
Asp Ser Val Val Tyr Gly Leu Arg Ser Lys Ser Lys Lys Phe Arg Arg
                 165                 170                 175
Pro Asp Ile Gln Tyr Pro Asp Ala Thr Asp Glu Asp Ile Thr Ser His
                 180                 185                 190
Met Glu Ser Glu Glu Leu Asn Gly Ala Tyr Lys Ala Ile Pro Val Ala
                 195                 200                 205
Gln Asp Leu Asn Ala Pro Ser Asp Trp Asp Ser Arg Gly Lys Asp Ser
         210                 215                 220
Tyr Glu Thr Ser Gln Leu Asp Asp Gln Ser Ala Glu Thr His Ser His
225                 230                 235                 240
Lys Gln Ser Arg Leu Tyr Lys Arg Lys Ala Asn Asp Glu Ser Asn Glu
                 245                 250                 255
His Ser Asp Val Ile Asp Ser Gln Glu Leu Ser Lys Val Ser Arg Glu
                 260                 265                 270
Phe His Ser His Glu Phe His Ser His Glu Asp Met Leu Val Val Asp
         275                 280                 285
Pro Lys Ser Lys Glu Glu Asp Lys His Leu Lys Phe Arg Ile Ser His
         290                 295                 300
Glu Leu Asp Ser Ala Ser Ser Glu Val Asn
305                 310
```